(12) United States Patent
Skaff et al.

(10) Patent No.: US 9,989,463 B2
(45) Date of Patent: Jun. 5, 2018

(54) MATERIAL CLASSIFICATION

(71) Applicant: CANON KABUSHIKI KAISHA, Tokyo (JP)

(72) Inventors: Sandra Skaff, Mountain View, CA (US); Chao Liu, Irvine, CA (US)

(73) Assignee: CANON KABUSHIKI KAISHA, Tokyo (JP)

( * ) Notice: Subject to any disclaimer, the term of this patent is extended or adjusted under 35 U.S.C. 154(b) by 521 days.

(21) Appl. No.: 14/635,848

(22) Filed: Mar. 2, 2015

(65) Prior Publication Data
US 2015/0219557 A1  Aug. 6, 2015

Related U.S. Application Data

(63) Continuation of application No. 14/541,561, filed on Nov. 14, 2014, now abandoned, which is a continuation-in-part of application No. 14/092,492, filed on Nov. 27, 2013, now abandoned, and a continuation-in-part of application No. 14/309,771, filed on Jun. 19, 2014, now Pat. No. 9,606,056, and
(Continued)

(51) Int. Cl.
G01N 21/55 (2014.01)
G01N 21/25 (2006.01)
B07C 5/342 (2006.01)
G01N 21/84 (2006.01)

(52) U.S. Cl.
CPC ............. *G01N 21/55* (2013.01); *B07C 5/342* (2013.01); *G01N 21/255* (2013.01); *G01N 2021/845* (2013.01); *G01N 2201/0627* (2013.01); *G01N 2201/12* (2013.01)

(58) Field of Classification Search
CPC ................. G01N 21/55; G01N 21/255; G01N 2201/0627; G01N 2021/845; G01N 2201/12; B07C 5/342
See application file for complete search history.

(56) References Cited

U.S. PATENT DOCUMENTS

| 4,311,393 A | 1/1982 | Bartke |
| 5,348,002 A | 9/1994 | Caro |
| 5,424,543 A | 6/1995 | Dombrowski et al. |

(Continued)

FOREIGN PATENT DOCUMENTS

WO  2011/014282 A2  2/2011

OTHER PUBLICATIONS

Wang, et al., "Material classification using BRDF slices", IEEE Conference on computer Vision and Pattern Recognition, pp. 1-7, CVPR, 2009.
(Continued)

*Primary Examiner* — Kyoung Lee
(74) *Attorney, Agent, or Firm* — Fitzpatrick, Cella, Harper & Scinto

(57) ABSTRACT

Material classification of an object is provided. Parameters for classification are accessed. The parameters include a selection to select a subset of angles for classification, a selection to select a subset of spectral bands for classification, a selection to capture texture features, and a selection to compute image-level features. The object is illuminated and a feature vector is computed based on the parameters. The material from which the object is fabricated is classified using the feature vector.

16 Claims, 30 Drawing Sheets

Related U.S. Application Data a continuation-in-part of application No. 14/312,614, filed on Jun. 23, 2014, now abandoned.

(60) Provisional application No. 61/842,338, filed on Jul. 2, 2013, provisional application No. 61/913,074, filed on Dec. 6, 2013.

(56) References Cited

U.S. PATENT DOCUMENTS

| | | | |
|---|---|---|---|
| 6,987,568 | B2 | 1/2006 | Dana |
| 7,075,534 | B2 | 7/2006 | Cole et al. |
| 7,924,315 | B2 | 4/2011 | Kanamori et al. |
| 7,929,142 | B2 * | 4/2011 | Ben-Ezra ............. G01N 21/474 356/445 |
| 7,940,396 | B2 | 5/2011 | Nisper et al. |
| 8,189,189 | B1 | 5/2012 | Herendeen et al. |
| 8,300,234 | B2 | 10/2012 | Debevec et al. |
| 8,405,832 | B2 | 3/2013 | Schmaelzle et al. |
| 8,515,716 | B2 | 8/2013 | Ingram et al. |
| 2011/0261355 | A1 | 10/2011 | Hannel et al. |
| 2012/0035884 | A1 | 2/2012 | Ingram et al. |
| 2012/0035900 | A1 | 2/2012 | Ingram et al. |
| 2014/0010443 | A1 | 1/2014 | Imai |
| 2015/0012226 | A1 | 1/2015 | Skaff |

OTHER PUBLICATIONS

Gu, et al., "Discriminative Illumination: Per-Pixel Classification of Raw Materials based on Optimal Projections of Spectral BRDF", IEEE Conference on Computer Vision and Pattern Recognition, pp. 1-8, CVPR 2012.

Gu, et al., "Classifying Raw Materials With Discriminative Illumination", Project Home Page, Rochester Institute of Technology, http"//www/cis.rit.edu/jwgu/research/fisherlight/, pp. 1-3, visited Jun. 19, 2013.

Varma, et al., "A Statistical Approach to Material Classification Using Image Patch Exemplars", IEEE PAMI, pp. 1-16, 2009.

Liu, et al., "Exploring Features in a Bayesian Framework for Material Recognition", IEEE CVPR, pp. 1-8, 2010.

Hu, et al., "Toward Robust Material Recognition for Everyday Objects", BMVC, pp. 1-11, 2011.

Jehle, et al., "Learning of Optimal Illumination for Material Classification", Heidelberg Collaboratory for Image Processing (HCI), University of Heidelberg, pp. 1-10, 2010.

U.S. Appl. No. 61/736,130, filed Dec. 12, 2010 by Francisco Imai, entitled "Systems and Methods for Material Classification Based on Decomposition of Spectra into Sensor Capturing and Residual Components".

RIT dataset of Spectral BRDF's of material samples (http://compimg1.cis.rit.edu/data/metal/) (2012).

Fuchs, et al., "Adaptive sampling of reflectance fields", ACM Transactions on Graphics (TOG), vol. 26, No. 2, article No. 10 (2007).

Gu, et al., "Supplementary Materials", Rochester Institute of Technology, <http://www.cis.rit.edu/jwgu/research/fisherlight/supplementary.pdf>, downloaded Jun. 19, 2013.

Lensch, et al., "Planned sampling of spatially varying BRDF's", Computer Graphics Forum, vol. 22, No. 3, pp. 473-482. Blackwell Publishing, Inc., 2003.

Matusik, et al., "Efficient isotropic BRDF measurement", Proceedings of the 14th Eurographics workshop on Rendering, pp. 241-247, Eurographics Association, 2003.

Imai, et al., "Comparison of Spectrally Narrow-Band Capture Versus Wide-Band with Priori Sample Analysis for Spectral Reflectance Estimation", 2000, IS&T.

Hahlweg, et al., "Classification of Optical Surface Properties and Material Recognition Using Multi-Spectral BRDF Data Measured With Semi-Hemispherical Spectro-Radiometer in VIS and NIR", SPIE 5965-16, 2005.

* cited by examiner

MATERIAL CLASSIFICATION

CROSS REFERENCE TO RELATED APPLICATIONS

The present application is a continuation and claims the priority benefit of co-pending U.S. patent application Ser. No. 14/541,561, filed Nov. 14, 2014, which is a continuation-in-part of U.S. application Ser. No. 14/092,492, filed Nov. 27, 2013, which in turn claims the priority benefit of U.S. Provisional Application No. 61/842,338, filed Jul. 2, 2013; U.S. application Ser. No. 14/309,771, filed Jun. 19, 2014, which in turn claims the priority benefit of U.S. Provisional Application No. 61/913,074, filed Dec. 6, 2013; and U.S. application Ser. No. 14/312,614, filed Jun. 23, 2014. The contents of all of the above applications are incorporated by reference herein.

FIELD

The present disclosure relates to material classification in which an object fabricated from an unknown material is illuminated with light, and light reflected therefrom is measured in an effort to identify the unknown material.

BACKGROUND

In the field of material classification, it has been considered to classify material through the use of so-called bidirectional reflectance distribution function (BRDF). In this approach, the object is illuminated from multiple different angles by multiple different light sources arranged in a hemispherical dome around the object, and reflected light from each light source is measured so as to form the BRDF, whereafter feature vectors are derived and the unknown material from which the object is fabricated is classified.

It has also been considered to include the notion of spectral BRDF, in which each light source is formed from six (6) differently-colored LEDs, so as to permit spectral tuning of each light source, thereby to differentiate between different materials with increased accuracy.

CITATIONS

1. Wang, O.; Gunawardane, P.; Scher, S. and Davis, J., "Material classification using BRDF slices", CVPR, 2009.
2. Gu, J. and Liu, C., "Discriminative Illumination: Per-Pixel Classification of Raw Materials based on Optimal Projections of Spectral BRDF", CVPR, 2012.
3. Gu, J., et al., "Classifying Raw Materials With Discriminative Illumination", Project Home Page, Rochester Institute of Technology, <http://www.cis.rit.edu/jwgu/research/fisherlight/>, visited Jun. 19, 2013.
4. Varma, M. and Zisserman, A., "A statistical approach to material classification using image patch exemplars", IEEE PAMI, 2009.
5. Liu, C.; Sharan, L.; Adelson, E. H. and Rosenholtz, R., "Exploring features in a Bayesian framework for material recognition", IEEE CVPR, 2010.
6. Hu, D. J.; Bo, L. and Ren, X., "Toward robust material recognition of everyday objects", BMVC, 2011.
7. Jehle, M.; Sommer, C. and Jhne, B., "Learning of optimal illumination for material classification", Pattern Recognition, 2010.

Citation [1] to Wang describes material classification using BRDFs (Bidirectional Reflectance Distribution Functions), and citation [2] to Gu describes spectral BRDFs. Additionally, in connection with citation [3] to Gu, a dataset of spectral BRDFs of material samples has been published in 2012 by RIT (see <http://compimg1.cis.rit.edu/data/metal/>). The dataset contains 100 material samples of 10 main categories. The setup for image capture constitutes a dome of 25 clusters, with 6 LEDs in each cluster. The method proposed by Gu in [2] computes the set of LEDs with their relative power needed to take the images of the materials in two shots for use in the classification algorithm.

SUMMARY

One difficulty with the foregoing approach is the nature and number of the light sources. The hemispherical dome proposed by Gu in [2] is provided with twenty-five (25) clusters of light sources, with six differently-colored (6) LEDs in each cluster, for a total of one hundred and fifty (150) LEDs, each with controllable intensity. This results in a geometric and dimensional expansion of the illumination configurations with which the object is illuminated, together with a corresponding geometric and dimensional expansion of the measurements of data for each configuration of illumination, and a corresponding geometric and dimensional expansion of the analysis thereof.

In more detail, according to the approach described by Gu in citation [2], with respect to spectral BRDF-based features and coded illumination to classify materials, the imaging framework consists of an LED-based multispectral dome in which a hemispherical geodesic dome is provided with twenty-five (25) LED clusters. Each LED cluster has 6 color LEDs over the visible wavelength range, the colors of which are blue, green, yellow, red, white, and orange. The white LED is placed in the center of the cluster. Therefore there are 150 (25×6) LEDs in total. The approach proposed in [2] computes the power of illumination for each of the LEDs in the dome such that the images for each material would be captured in two shots. Therefore, using this approach for material classification, the entire dome and its arrangement of LEDs into 25 clusters are both required.

Embodiments described herein illustrate techniques whereby the number of clustered light sources can be reduced from a superset of many light sources down to a subset of far fewer light sources, without any significant loss in accuracy for material classification. For example, according to embodiments herein, the number of clustered light sources can be reduced from a superset of around twenty-five (25) light sources down to (for example) a subset of two or three light sources, without any significant loss in accuracy for material classification. In general, the technique involves the use of labeled training data for selection of the best two or three angular locations for incident angles of multispectral light sources which illuminate objects, together with selection of a suitable feature vector for capturing the reflection measurements with efficient dimensionality. Thereafter, armed with the two or three best locations for incident angles of illumination, together with the selected feature vector, a classification algorithm is trained, and objects of unknown materials are subjected to measurement and classification.

More specifically, given a database of labeled training data, captured under a relatively large number of light sources from different incident angles, a feature vector representation is calculated for the training data, and mathematical clustering (such as K-means clustering) is performed so as to identify two or three mathematically significant clusters of data for a corresponding two or three illumination angles. Based on these mathematical clusters, whose locations might not correspond to the physical locations of actual light sources, the angle of incident illumination and spectral content of the two or three best physical light sources are selected.

Thereafter, given the data from the selected physical light sources, and the selected feature vectors, a classification engine is trained using the training data. One classification engine might include an SVM (support vector machine) algorithm.

The results are thereafter applied to objects of unknown materials. In particular, an object of an unknown material is illuminated with the two or three optimally-selected light sources, and a feature vector is calculated from measurements obtained thereby. The feature vector is input into the trained classification algorithm, so as to obtain a classification estimate of the unknown material from which the object is fabricated.

Thus, one aspect of the description herein concerns material classification in which an object fabricated from an unknown material is positioned at a classification station which includes plural light sources each positioned at a predesignated incidence angle with respect to the object, and which further includes one or more image capture devices such as a digital camera each positioned at a predesignated exitant angle with respect to the object. At the classification station, the object is illuminated with light from the light sources, and an image of the light reflected from each illumination is captured by the capture device, so as to capture plural images each respectively corresponding to an illumination. The images are processed to extract BRDF slices and other feature vectors, and the feature vectors are inputted into a trained classification engine so as to classify the unknown material from which the illuminated object is fabricated.

The predesignated incident angles for the illumination from the light sources, and/or the spectral content of the light sources, are determined as described herein in connection with further embodiments. In one aspect, a labeled training sample is used for selection of the best few angular locations, such as the best two or three angular locations, for incident angles of multispectral light sources which illuminate objects. More specifically, given a database of labeled training data, captured under a relatively large number of light sources from different incident angles, a feature vector algorithm is applied to the captured image data for the training sample, so as to extract a feature vector, and mathematical clustering (such as K-means clustering) is performed so as to identify two or three mathematically significant clusters of data for a corresponding two or three illumination angles, and/or to identify two or three mathematically significant clusters of data for a corresponding two or three spectral wavelengths. Based on these mathematical clusters, whose locations and wavelengths might not correspond to the physical locations and wavelengths of actual light sources, the angle of incidence and/or spectral content of the two or three best physical light sources are selected.

Thereafter, given the data from the selected physical light sources, and the selected feature vectors, a classification engine is trained using the training data. One classification engine might include an SVM (support vector machine) algorithm.

These are provided as the predesignated incidence angles for the light sources, and/or the spectral content of the light sources, when classifying the material type of objects of unknown materials. In addition, when classifying object of unknown material, the same feature vector algorithm is applied to extract BRDFs and other feature vectors, and the trained classification engine is used.

Thus, in general, the disclosure herein is directed to material classification using illumination by spectral light from multiple different incident angles, coupled with measurement of light reflected from the illuminated object of unknown material, wherein the incident angle and/or spectral content of each illumination source is selected based on a mathematical clustering analysis of training data, so as to select a subset of only a few light sources from a superset of many light sources.

Further aspects described herein involve selection of incident illumination angles using spectral BRDF slices for material classification. Given a database of labeled training material samples captured under a relatively large number of incident illumination directions: (a) low-level feature vector representations are computed of these materials; (b) clustering, such as K-means clustering, is performed on the low-level features along the angle dimension to find the optimal directions of illumination; and (c) directions are selected for the optimal light source (such as LED) directions of the imaging setup which are closest to the directions provided by the estimated clusters, using an appropriate distance metric.

Thereafter, given the optimal light source directions as selected above, and the corresponding images obtained using them, the feature vector representations of the material samples are taken to be the low-level features computed using these images. Then: (a) a classification engine is trained, such as SVM, on the set of features of the training samples; (b) the trained classification engine is used along with an imaging setup including the optimal light source directions in a factory setting to obtain images of and to classify new material samples as observed.

The low-level feature vectors may be computed as the means of the intensities of the spectral BRDF slice images. The feature vectors may be obtained by application of a feature vector algorithm that computes the histogram over the clusters using all the spectral BRDF slices of a training sample. The distance metric can be the Euclidean distance, L1 or other appropriate metrics.

The training images in the labeled training sample may be labeled by material by calculating a probability function based on determining a correlation between a sample signature and a set of pre-labeled signatures in a database. In this regard, reference is made to U.S. Application No. 61/736,130, filed Dec. 12, 2012 by Francisco Imai, "Systems And Methods For Material Classification Based On Decomposition Of Spectra Into Sensor Capturing And Residual Components", the contents of which are incorporated by reference herein, as if set forth in full.

The number of optimal incident illumination angles may be selected automatically using a mathematical clustering algorithm such as convex clustering. The clusters may then be computed using K-means, Gaussian Mixture Models, or other appropriate algorithms. Material classifications may include material sub-categories.

The classification engine may be configured to make a decision for cases with a pre-determined level of confidence in the prediction. When a decision is not made, the sample can be sent to a human for labeling.

In addition, although some embodiments may be based on a one-time training of the classification engine, in other embodiments, the classification engine may be trained more than once, or may be updated at intervals, such as by training on-line with new material samples. In this regard, and particularly with respect to objects not classified with confidence by the engine, and for which a manual classification was needed, the training for the classification engine can be updated using the manually-classified result.

Aspects described herein include selection of incident illumination angles for illumination of an object by respective light sources, wherein the incident illumination angle of each light source is selected based on a mathematical clustering analysis of labeled training data captured under a superset of a second number of light sources from different incident angles, so as to select a subset of incident illumination angles by a first number of light sources from the superset of the second number of light sources, the first number being smaller than the second number. There may include calculating a feature vector representation for training data in a database of labeled training data captured under the superset of the second number of light sources from different incident angles; performing mathematical clustering on the feature vector representations so as to identify a subset of mathematically significant clusters of data for a corresponding first number of incident illumination angles; and selecting incident illumination angles for the light sources based on the mathematical clusters.

According to such aspects, directions for the incident illumination angles for the light sources may be selected using a distance metric selected from a group consisting essentially of a Euclidean distance metric and an L1 distance metric. The mathematical clustering may include clustering by a clustering algorithm selected from a group consisting essentially of K-means clustering and Gaussian Mixture Models clustering. BRDF (bidirectional reflectance distribution function) slices may be used. The feature vectors may comprise means of intensities of the BRDF slices; or histograms over features of the spectral BRDF slices of a training sample; or may be obtained by application of a feature vector algorithm that computes the histogram over the clusters using all the spectral BRDF slices of a training sample.

Further according to such aspects, the training data may be captured from a superset of a relatively large number of exitant angle, and there may include selecting a subset of a relatively small number of mathematically significant clusters of data for a corresponding small number of exitant angles by using mathematical clustering.

Further according to such aspects, the number of mathematically significant clusters may be selected automatically using a mathematical clustering algorithm which may include convex clustering. Each light source in the database of labeled training data may comprise a multi-spectral light source, and there may include selecting a subset of a relatively small number of mathematically significant clusters of illumination spectra for subset of incident illumination angles by using mathematical clustering.

Further according to such aspects, the database of labeled training data may comprise a database of labeled training material samples captured in an imaging configuration under a relatively large number of incident illumination directions. The feature vector may be calculated by computing low-level feature vector representations of such materials; and the mathematical clustering may be performed on the low-level features along an angle dimension to find optimal directions of illumination. Selecting incident angles may comprise selecting directions for the optimal light source of the imaging configuration which are closest to directions provided by the mathematical clusters. Directions for the optimal light sources may be selected using a distance metric selected from a group consisting essentially of a Euclidean distance metric and an L1 distance metric. The low-level feature vectors may be computed as the means of the intensities of spectral BRDF slices.

Further according to such aspects, the illuminated object is fabricated from an unknown material and is illuminated by the light sources for material classification, and there may comprise training a classification engine for material classification, wherein the classification engine is trained using feature vectors calculated from training data corresponding to light sources for the selected incident angles. The classification engine may include an SVM (support vector machine) algorithm. Material classification may include material sub-categories. The classification engine may be configured to make a decision for cases with a pre-determined level of confidence. In response to failure of the classification engine to make a decision, the object may be subjected to manual labeling. The classification engine may be trained multiple times for updating of its training by new material samples. The classification engine may be configured to make a decision for cases with a pre-determined level of confidence, and in response to failure of the classification engine to make a decision with confidence by the engine, the object may be subjected to manual labeling, and the training for the classification engine may be updated using the manually-classified result. There may further comprise capturing reflected light information from an object of unknown material illuminated in an imaging configuration that includes the selected optimal light source directions; and applying the trained classification engine to the captured light information to classify the material of the illuminated object.

Aspects described herein also include material classification of an object fabricated from an unknown material, comprising illuminating an object by spectral light from multiple different incident angles using multiple light sources; measuring light reflected from the illuminated object; and classifying the material from which the object is fabricated using the measured reflected light. The incident illumination angle of each light source is selected based on a mathematical clustering analysis of labeled training data captured under a superset of light sources from different incident angles, so as to select a subset of incident illumination angles by first number of light sources from a superset of second number of light sources, the first number being smaller than the second number.

According to such aspects, classification may comprise applying a trained classification engine to the captured light information to classify the material of the illuminated object. The classification engine may be trained using feature vectors calculated from training data corresponding to light sources for the selected incident angles. The classification engine may be trained multiple times for updating of its training by new material samples. The classification engine may be configured to make a decision for cases with a pre-determined level of confidence, and in response to failure of the classification engine to make a decision with confidence by the engine, the object may be subjected to manual labeling, and the training for the classification engine may be updated using the manually-classified result.

Aspects described herein also include material classification of an object fabricated from an unknown material, comprising illuminating an object positioned at a classification station by plural light sources each positioned at a predesignated incidence angle with respect to the object; capturing plural images of light reflected from the illuminated object, each of the plural images corresponding respectively to illumination by a respective one of the plural light sources; extracting a respective plurality of feature vectors from the plural captured images by using a feature vector algorithm; and processing the plurality of feature vectors using a trained classification engine so as to classify the unknown material of the object. The predesignated incident angles are determined by calculating a feature vector representation for training data in a database of labeled training data captured under a superset of a second number of light sources light sources from different incident angles, so as to select a subset of incident illumination angles by a first number of light sources from the superset of the second number of light sources, the first number being smaller than the second number, wherein the feature vector is calculated using the feature vector algorithm; performing mathematical clustering on the feature vector representations so as to identify a subset of mathematically significant clusters of data for a corresponding the first number of incident illumination angles; and selecting incident illumination angles for the light sources based on the mathematical clusters. The classification engine is trained by using feature vectors calculated from training data corresponding to light sources for the selected incident angles.

According to such aspects BRDF (bidirectional reflectance distribution function) slices may be used. The feature vectors may comprise means of intensities of the BRDF slices. The feature vectors may comprise histograms over features of the spectral BRDF slices of a training sample. The feature vectors may be obtained by application of a feature vector algorithm that computes the histogram over the clusters using all the spectral BRDF slices of a training sample.

Further according to such aspects, material classification may include material sub-categories. The classification engine may be configured to make a decision for cases with a pre-determined level of confidence. In response to failure of the classification engine to make a decision, the object may be subjected to manual labeling. The classification engine may be trained multiple times for updating of its training by new material samples. The classification engine may be configured to make a decision for cases with a pre-determined level of confidence, and in response to failure of the classification engine to make a decision with confidence by the engine, the object may be subjected to manual labeling, and the training for the classification engine may be updated using the manually-classified result.

Further according to such aspects, each light source in the database of labeled training data may comprise a multispectral light source, and there may further comprise selecting a subset of a relatively small number of mathematically significant clusters of illumination spectra for each of incident illumination angle in the subset of incident illumination angles by using mathematical clustering; training the classification engine using feature vectors calculated from training data corresponding to light sources for the selected illumination spectra; and illuminating the object with the selected illumination spectra.

Meanwhile, there has apparently been only one approach in the literature which uses spectral BRDF-based features and coded illumination to classify materials. See Gu at [2]. The imaging framework consists of an LED-based multispectral dome and the hemispherical geodesic dome has 25 LED clusters. Each LED cluster has 6 color LEDs over the visible wavelength range, the colors of which are blue, green, yellow, red, white, and orange. The same LEDs are used to image all material samples, and they are limited in number to 6.

The previous approach which uses spectral BRDF based features for material classification uses 150 LEDs for capturing the material images. As described in the previous section, the LEDs are the same for all material images, their spectra are broadband, and they are limited in number to six (6).

Further described herein is an embodiment which uses 32 narrow spectral bands as compared with 6 broadband ones for imaging materials for the purpose of classifying them. In this embodiment, these 32 bands are obtained through the usage of a Liquid Crystal Tunable Filter (LCTF) mounted in front of the camera lens. FIG. 14 shows the spectral transmissions of the 32 bands as provided by the manufacturer. There are 32 narrow spectral bands in total ranging from 410 nm to 720 nm with an interval of 10 nm. Imaging materials with narrow bands would provide images which are more discriminative in terms of subtle changes in the spectral reflectance of different materials.

Also described herein is an embodiment by which a subset of fewer than the 32 filters is selected. The subset may, for example, contain five (5) filters selected from the 32 filters, and the filters in the subset are selected in such a way as to provide significant discrimination among the materials to be classified. Reducing the number of filters needed, from a first large number such as 32 to a second lower number such as 5, has several advantages in a recycling factory or other industrial inspection or robotic application settings. These advantages include reducing capture time, reducing cost through replacing an expensive LCTF with a filter wheel which would use around 5 filters, and providing the potential to design a color filter array for material sensing. These advantages are described in more detail below.

Aspects described herein thus include selection of spectral bands using spectral BRDF slice images captured under multiplexed illumination for material classification, and may comprise analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials.

According to further aspects described herein, analysis may comprise access to a database of labeled training material samples within a multi-class classification framework, the samples being captured using a relatively large number of spectral bands, computation of feature vector representations of these materials, machine-learning of a set of weights representing the importance of the spectral bands on the features in each binary classification task, conversion of weights from the binary classification tasks to a set of weights for the multi-class classification framework using a mapping function, and selecting spectral bands of highest weight as the selected spectral bands.

According to still further aspects described herein, a set of weights may be learned by application of an Adaboost algorithm. A classification engine may be trained using the selected spectral bands, the corresponding images obtained using them, and feature vector representations computed from the material samples using these images. Material sub-categories may be considered. The feature vectors may be pixel intensities of spectral BRDF slice images captured under multiplexed illumination, and the feature vector representations may be learned using pixel intensities of spectral BRDF slice images captured under multiplexed illumination. The training images may be labeled by material by calculating a probability function based on determining a correlation between a sample signature and a set of pre-labeled signatures in a database. The number of selected spectral bands may be selected automatically, for example, using thresholding on the weights.

Aspects described herein also include selection of spectral bands using spectral BRDF slice images captured under multiplexed illumination for material classification, by accessing a database of labeled training material samples within a multi-class classification framework, captured using a relatively large number of spectral bands; computing feature vector representations of these materials; learning a set of weights representing the importance of the spectral bands, using Adaboost for example, on the features in each binary classification task; converting the weights from the binary classification tasks to a set of weights for the multi-class classification framework using a mapping function; and selecting spectral bands of highest weight as the selected spectral bands. A classification engine may be trained using the selected spectral bands, the corresponding images obtained using them, and feature vector representations computed from the material samples using these images.

According to such aspects, the feature vectors may be pixel intensities of spectral BRDF slice images captured under multiplexed illumination, or the feature vector representations may be learned using pixel intensities of spectral BRDF slice images captured under multiplexed illumination. The training images may be labeled by material by calculating a probability function based on determining a correlation between a sample signature and a set of pre-labeled signatures in a database. The number of selected spectral bands may be selected automatically, for example, using thresholding on the weights. Material sub-categories may be considered.

With respect to labeling of training images by material by calculating a probability function based on determining a correlation between a sample signature and a set of pre-labeled signatures in a database, reference is made to the following which are incorporated herein by reference as if set forth herein in full: (1) U.S. Provisional Application No. 61/736,130, filed Dec. 12, 2012 and assigned to the Applicant herein, entitled "Systems and Methods for Material Classification Based on Decomposition of Spectra into Sensor Capturing and Residual Components" by Francisco Imai; and (2) U.S. application Ser. No. 13/887,163, filed May 3, 2013 and assigned to the Applicant herein, entitled "Method for Simultaneous Colorimetric and Spectral Material Estimation" by Francisco Imai, now published at U.S. Patent Application Publication No. 2014/0010443.

Aspects described herein also include material classification of an object fabricated from an unknown material, and may comprise illuminating an object by multiplexed illumination such as by using multiple broadband light sources, measuring multiple spectral bands of light reflected from the illuminated object, and classifying the material from which the object is fabricated using the measured reflected light. With respect to the measured multiple spectral bands, wavelengths for the multiple spectral bands may be selected by analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials in the database.

With respect to the spectral bands at which light reflected from the illuminated object is measured, the spectral bands may be implemented as spectral bands from a spectrally-narrow light source or sources, or as spectral filters on the light source or on the reflected light, or as combinations thereof.

According to aspects described herein, the multiple spectral bands may be selected by steps which include computing feature vector representations of the materials in the database, learning a set of weights representing the importance of the spectral bands, using Adaboost for example, on the features in each binary classification task, converting the weights from the binary classification tasks to a set of weights for the multi-class classification framework using a mapping function, and selecting spectral bands of highest weight as the selected spectral bands.

Further according to such aspects, feature vector representations may be computed from the measured spectral bands. The feature vectors may be pixel intensities of spectral BRDF slice images captured under multiplexed illumination, or the feature vector representations may be learned using pixel intensities of spectral BRDF slice images captured under multiplexed illumination.

Further according to such aspects, classification may comprise applying a trained classification engine to the captured light information to classify the material of the illuminated object. Material sub-categories may be considered. The trained classification engine may make a decision for cases with a pre-determined level of confidence in the prediction. When a decision is not made, the sample may be subjected to manual labeling. The trained classification engine may be trained on-line with new material samples. The trained classification engine may make a decision for cases with a pre-determined level of confidence in the prediction, wherein when a decision is not made, the sample is subjected to manual labeling in which the sample is placed into an online material classifier.

According to further aspects, the disclosure herein describes finding a subset of spectral bands that are optimized to classify the materials in a group of materials. The optimized subset of spectral bands allows classification of the materials in the group of materials without a significant loss of classification accuracy. Thus, given a set of materials, a set of spectral bands, and a first group of materials that are to be classified, the system determines a subset of spectral bands that is optimized to detect the first group. Different optimized subsets of spectral bands may be generated for the different groups of materials. For example, even though two groups of materials might overlap, their respective optimized subsets of spectral bands do not necessarily overlap. Also, although two groups of materials might not overlap, their respective optimized subsets of spectral bands might in fact overlap.

Another problem with the conventional feature vector is its high dimensionality, particularly due to per-pixel classification of images. For example, given a relatively modest database of 150 image slices having 1000×1000 pixels in size for 100 material samples of 10 main categories, the number of samples would be $1000 \times 1000 \times 150 = 150 \times 10^6$, for a dimensionality of the same $150 \times 10^6$. The space required to store these samples, and the power and time required to process them, scale with the number of materials, leading to an impractical situation.

The foregoing situation is addressed by computing a feature vector representation for an image slice based on clustering of low-level features of the image slice.

Thus, in an example embodiment described herein, feature vector representations are computed for BRDF image slices in a database of known materials captured under a relatively large number of incident illumination directions.

Low-level features of each image slice are clustered into two or more clusters. An intermediate feature vector representation is computed for each image slice with entries that are weighted means of the clusters.

By computing a feature vector representation for an image slice based on clustering of low-level features of the image slice, it is ordinarily possible to represent the BRDF based features of material while substantially reducing the size of the data.

In one example aspect, the low-level features of each image slice are clustered into at least two clusters such as a first cluster for specular reflections and a second cluster for diffuse reflections, or into at least three clusters such as a first cluster for specular reflections, a second cluster for diffuse reflections, and a third cluster for dark reflections.

In another example aspect, feature vector representations of each slice are computed by sorting all entries of the intermediate feature vector representations by the mean of the corresponding clusters.

In still another example aspect, a classification engine is trained for material classification using the computed feature vector representations of labeled training data.

In yet another example aspect, an object fabricated from an unknown material is illuminated, and BRDF image slices for the illuminated object are captured. A feature vector representation is computed for the BRDF image slices of the object of unknown material, and the material for the unknown object is classified by applying the feature vector representation of the unknown object to the trained classification engine.

In another example aspect, material classification includes material sub-categories. In still another example aspect, the classification engine is configured to make a decision for classification with a pre-determined level of confidence. In yet another example aspect, in response to failure of the classification engine to make a decision, the object is subjected to a manual labeling.

In still another example aspect, the number of clusters is selected automatically by using a clustering algorithm. In one example aspect, clustering includes application of K-means clustering on the low-level features for each image slice. In another example aspect, K-means clustering is applied to derive more than three clusters. In yet another example aspect, with respect to the clusters for specular reflections, diffuse reflections and dark reflections, at least one such cluster includes a sub-cluster. In still another example aspect, the low-level features include pixel intensity values of the BRDF image slices.

In another example aspect, the database of labeled training data is labeled according to classification of material by calculating a probability function based on determining a correlation between a sample signature and a set of pre-labeled signatures in a database.

In still another example aspect, the intermediate feature vectors are computed by using an algorithm selected from the group including, but not limited to, K-means algorithm and Gaussian Mixture Models.

In yet another example embodiment described herein, material classification is achieved using an approach to jointly learn optimal incident illumination, both angle and wavelength, using spectral BRDF image slices of raw materials. In such an approach, the orientation invariant image-level feature vectors which represent specular, diffuse and dark components of these BRDF image slices are extracted.

In another aspect, the feature vectors are further used to cluster angles by spectral BRDF images in a joint learning algorithm. This clustering allows for reduction in the search space of optimal angle and wavelength.

This brief summary has been provided so that the nature of this disclosure may be understood quickly. A more complete understanding can be obtained by reference to the following detailed description and to the attached drawings.

BRIEF DESCRIPTION OF THE DRAWINGS

FIGS. 12 and 13 illustrate a further embodiment for the determination and calculation of the spectral wavebands used by the classification system depicted in FIG. 9, wherein FIG. 12 illustrates an embodiment in which a training sample of objects fabricated from known materials is subjected to illumination from multiple light sources, and wherein FIG. 13 illustrates more details concerning the internal architecture of a light source configuration controller and analyzer.

DETAILED DESCRIPTION

FIGS. 1 to 8 illustrate techniques for a material classification environment, whereby the number of clustered light sources can be reduced from a superset of many light sources down to a subset of far fewer light sources, without any significant loss in accuracy for material classification.

Approaches previously considered for spectral BRDF-based features for material classification use large numbers of sight sources and corresponding image captures, such as 150 LEDs for capturing the material images. As described previously, the LEDs are clustered into groups of six (6) LEDs each, yielding twenty-five (25) clusters in total. Building a dome with 150 LEDs to deploy in a factory or other industrial robotic application setting is cumbersome and difficult to maintain. In this description, therefore, there is a selection of the most discriminative LED clusters, corresponding to incident illumination angles, which would be sufficient to image and to classify a set of given materials. With this approach, as few as only 2 or 3 LED clusters or incident illumination angles (12 or 18 spectral BRDF slices) can be used, while not compromising on the accuracy of material classification.

In this discussion, it is assumed that all LEDs in one cluster have the same incident illumination angle. This is a valid assumption since the difference in the incident angle illumination for the LEDs is very small and can be attributed to noise in a real-world setting.

Figure 1:
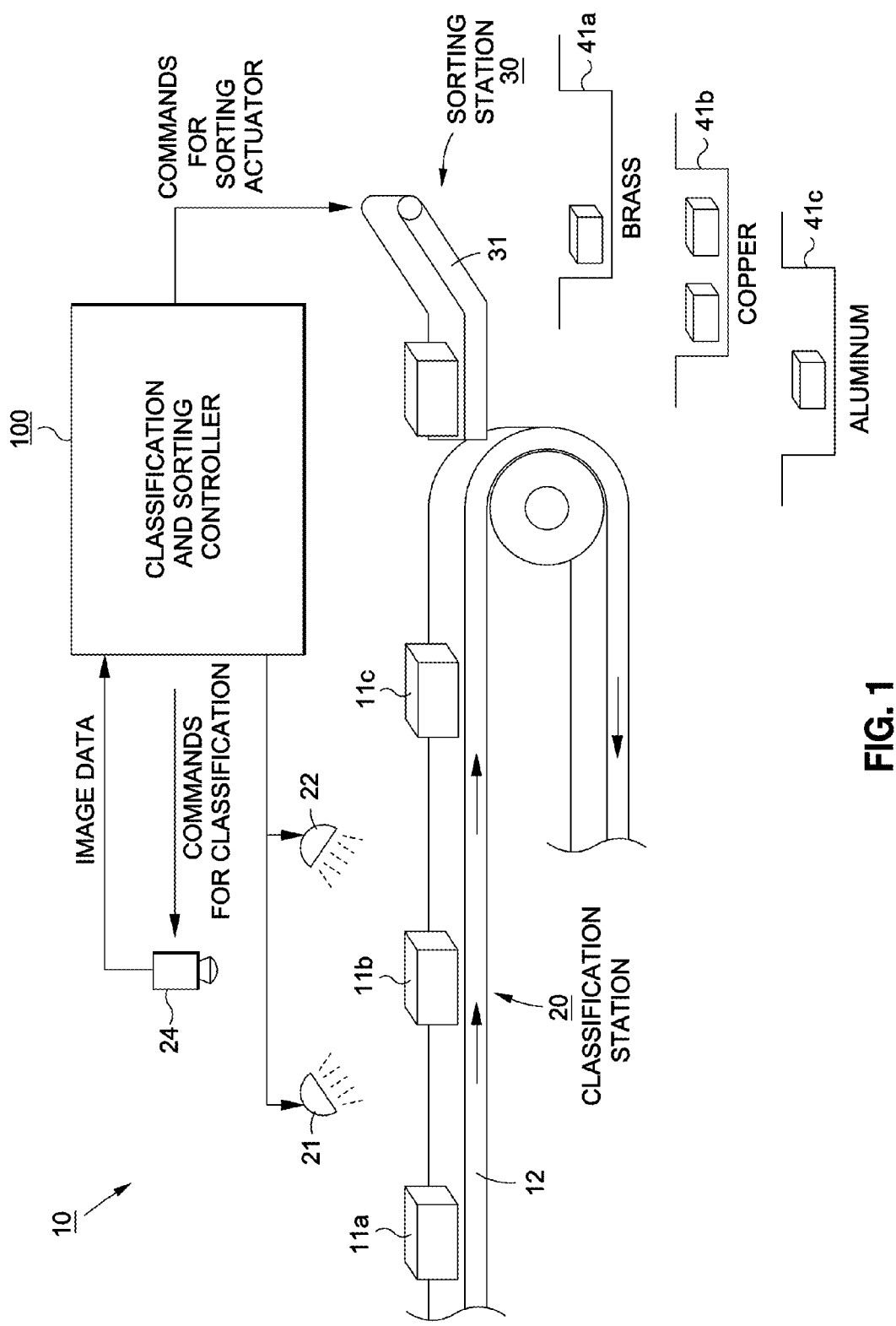
FIG. 1 is an example embodiment of a classification system according to the description herein, in the form of a recycling system in which objects to be recycled are classified according to the materials from which the objects are fabricated, and the classified objects are sorted for recycling according to their material classification.

FIG. 1 is an example embodiment of a classification system according to the description herein, in the form of a recycling system 10 in which objects to be recycled are classified according to the materials from which the objects are fabricated, and the classified objects are sorted for recycling according to their material classification. As shown in FIG. 1, objects 11a, 11b, etc. are conveyed on a conveyor mechanism 12 to a classification station 20, where the objects are classified according to their material, and thence to a sorting station 30, where the objects are sorted according to their material classification. Classification station 20 includes plural light sources 21 and 22, together with a camera 24 for capturing images of objects positioned at classification station 20. The object at the classification station is illuminated individually by each of the plural light sources under control of classification and sorting controller 100, and camera 24 captures one or more images for each individual illumination. Under control of the classification and sorting controller 100, a classification is made for the material from which the object is fabricated.

Conveyor mechanism 12 continues to convey the object to sorting station 30, where sorting actuator 31 sorts the objects according to the material classification. Sorting is controlled by classification and sorting controller 100, which commands actuator mechanism 31 to sort the classified objects into multiple receptacles 41a, 41b and 41b.

In this example embodiment, material classification differentiates between different types of metals from which the objects are fabricated, such as brass, copper and aluminum. Naturally, it will be understood that this is a non-limiting example. In other embodiments, material classification could differentiate between metal, plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

A description will now be made of the angular positioning of the plural light sources and the camera relative to the object at the classification station, the spectral content of the light sources, and the spectral sensitivity of the camera.

Figure 2:
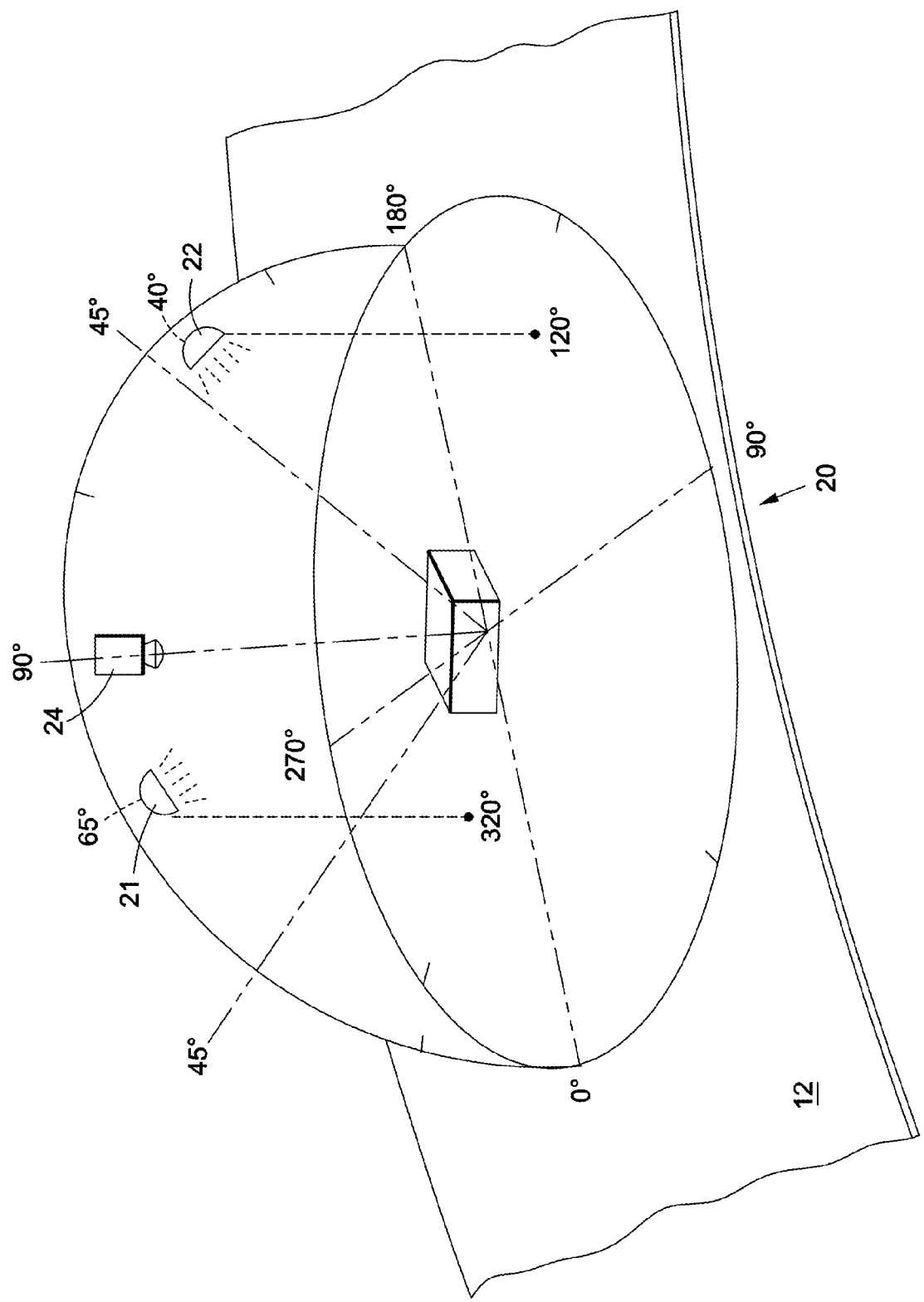
FIG. 2 is a more detailed view of an object being subjected to classification at a classification station of the FIG. 1 view.

FIG. 2 is a more detailed view of an object on conveyor mechanism 12 at classification station 20. In this figure, an angular coordinate system has been superimposed for purposes of explanation, and for purposes of explaining the angle of incidence for each of light sources 21 and 22, and the angle of exitant for light reflected from the object and imaged by camera 24. In this example embodiment, light source 21 is positioned at an incident angle of 320 degrees azimuth and 65 degrees elevation; and light source 22 is positioned at an incident angle of 120 degrees azimuth and 40 degrees elevation. Also in this example, camera 24 is positioned at an exitant angle of 90 degrees elevation. The derivation and calculation for these incident and exitant angles are described in greater detail below in connection particularly with FIGS. 4 through 8.

With respect to the spectral content of light sources 21 and 22, each light source is formed from an LED cluster with six (6) differently-colored LEDs arranged circularly with a white LED in the center. In this embodiment, the LEDs cover the visible wavelength range, and include the colors of blue, green, yellow, red, orange and the afore-mentioned white. In other embodiments, it might be helpful to include LEDs beyond the visible wavelength, such as LEDs which emit light in the ultraviolet or infrared range. The precise spectral content of the light sources is discussed in greater detail below, but in general will assist in distinguishing between different classifications of materials.

Camera 24 in this embodiment is a RGB camera, and it thus exhibits spectral sensitivity in each of the red, green and blue wavelengths. In other embodiments, camera 24 might include spectral sensitivity in wavelengths other than red, green, and blue, or it might include a monochrome camera which exhibits broad spectral sensitivity across the visible and near-visible ranges of wavelengths, possibly along with a liquid crystal tunable filter.

As shown in FIG. 2, this example embodiment includes two (2) light sources and one (1) camera. The determination of the number of light sources, together with their incident angles, is discussed below in greater detail, particularly with respect to FIGS. 4 through 8. Likewise, the number of cameras, together with their exitant angles, is discussed in greater below in connection with the same figures. In general, however, in order to facilitate rapid classification of materials, such as real-time classification of materials, the number of light sources, and the number of cameras is relatively small, such that materials can be classified with only a few illuminations and with only a few images for each such illumination. Preferably, the number of light sources should range between two and five, inclusive, most preferable two or three light sources, and the number of cameras should range between one and two, inclusive, most preferably one camera.

Although in this embodiment the spectral content of each individual light source is identical to all others, it should be understood that the spectral content of the light sources might differ from each other. Likewise, in embodiments where there are plural cameras, although the spectral sensitivities of the cameras might match, it is also possible for the spectral sensitivities to differ.

Under control of classification and sorting controller 100, each individual LED in each individual light source of the plural light sources is illuminated individually and independently of other LEDs in the light source, and independently and individually of other light sources and other LEDs in those other light sources. For each such illumination, camera 24 captures an image of light reflected from the object at the exitant angle. The captured images are collected by classification and sorting controller 100, and are analyzed thereby, such as by deriving one slice of the so-called bidirectional reflectance distribution function (BRDF). The BRDF is a four-dimensional function that depends on incident and exitant angles, and defines how light is reflected from the surface of an object. With a camera positioned at a fixed exitant angle, only a "slice" of the BRDF is obtained.

Based on the BRDF slices, and other analysis which includes application of a feature vector algorithm to extract feature vectors for each image, and feeding of such feature vectors to a trained classification engine, classification and sorting controller 100 obtains a classification of the material from which the illuminated object is fabricated.

Figure 3:
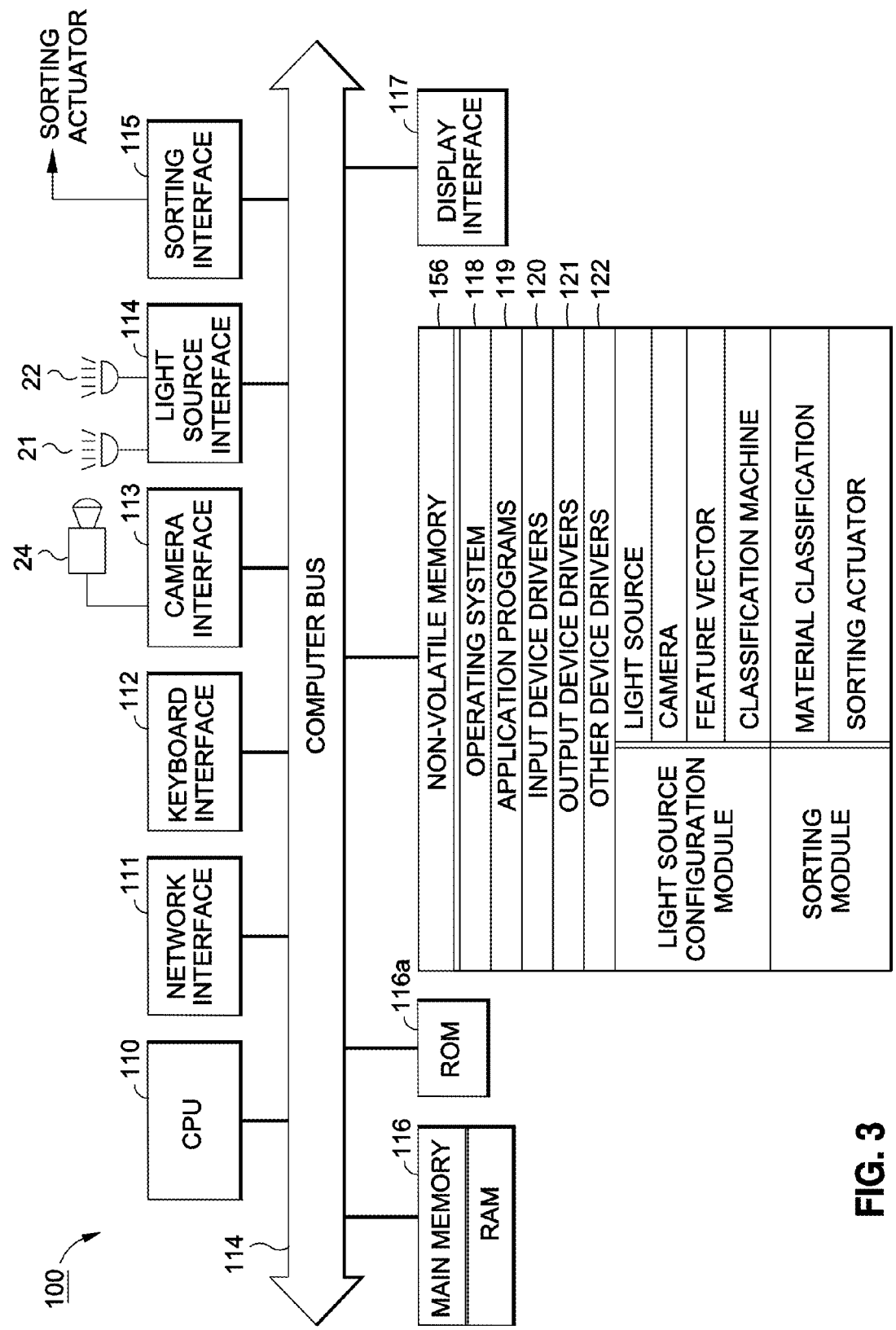
FIG. 3 is a view for explaining the architecture of a classification and sorting controller.

FIG. 3 is a view for explaining the architecture of classification and sorting controller 100.

As shown in FIG. 3, classification and sorting controller 100 includes central processing unit (CPU) 110 which interfaces with computer bus 114. Also interfacing with computer bus 114 are non-volatile memory 156 (e.g., a hard disk or other nonvolatile storage medium), network interface 111, keyboard interface 112, camera interface 113, random access memory (RAM) 116 for use as a main run-time transient memory, read only memory (ROM) 116a, and display interface 117 for a display screen or other output.

RAM 116 interfaces with computer bus 114 so as to provide information stored in RAM 116 to CPU 110 during execution of the instructions in software programs, such as an operating system, application programs, image processing modules, and device drivers. More specifically, CPU 110 first loads computer-executable process steps from non-volatile memory 156, or another storage device into a region of RAM 116. CPU 110 can then execute the stored process steps from RAM 116 in order to execute the loaded computer-executable process steps. Data, also, can be stored in RAM 116 so that the data can be accessed by CPU 110 during the execution of the computer-executable software programs, to the extent that such software programs have a need to access and/or modify the data.

As also shown in FIG. 3, non-volatile memory 156 contains computer-executable process steps for operating system 118, and application programs 119, such as graphic image management programs. Non-volatile memory 156 also contains computer-executable process steps for device drivers for software interface to devices, such as input device drivers 120, output device drivers 121, and other device drivers 122.

Non-volatile memory 156 also stores a material classification module and a sorting module. The material classification module and the sorting module comprise computer-executable process steps for material classification of an object fabricated from an unknown material, and for sorting the object based on the material classification.

The computer-executable process steps for these modules may be configured as part of operating system 118, as part of an output device driver in output device drivers 121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The material classification module includes a corresponding plurality of modules for control of the light sources, for control of the camera(s) and for gathering of image data of such camera(s) a module for derivation of feature vectors according to a feature vector algorithm, such as feature vectors based on BRDF slices, and a classification machine. The classification machine accepts as inputs the feature vectors derived by the feature vector module, and provides a classification of the material from which the object under inspection is fabricated.

More details concerning the nature of the feature vector algorithm and the classification machine are provided below, in connection with FIGS. 4 through 8.

The sorting module for its part includes a corresponding plurality of modules related to input of material classification from the classification machine, and actuation of the sorting mechanism based on the classification.

FIGS. 4 through 8 describe a further embodiment according to the description herein. These figures are used to describe the determination and calculation of the angular placement for the plural light sources depicted in FIG. 1, the angular placement of the camera(s) depicted in FIG. 1, the spectral content of the plural light sources, and the spectral sensitivity of the camera.

In particular, FIGS. 4 through 8 describe an embodiment in which a training sample of objects fabricated from known materials is subjected to illumination from a large number of light sources at a respectively large number of incident angles, together with the capture of a corresponding large number of images by one or more cameras of BRDF slices and other feature vectors are calculated from the captured images, and a mathematical clustering is performed on the feature vectors so as to identify a relatively small number of incident angles of light sources, and/or spectral content thereof, with the most significant aptitude for distinguishing between materials. A classification machine is trained using the feature vectors corresponding to the identified clusters, using the labels from the labeled training sample.

Figure 4:
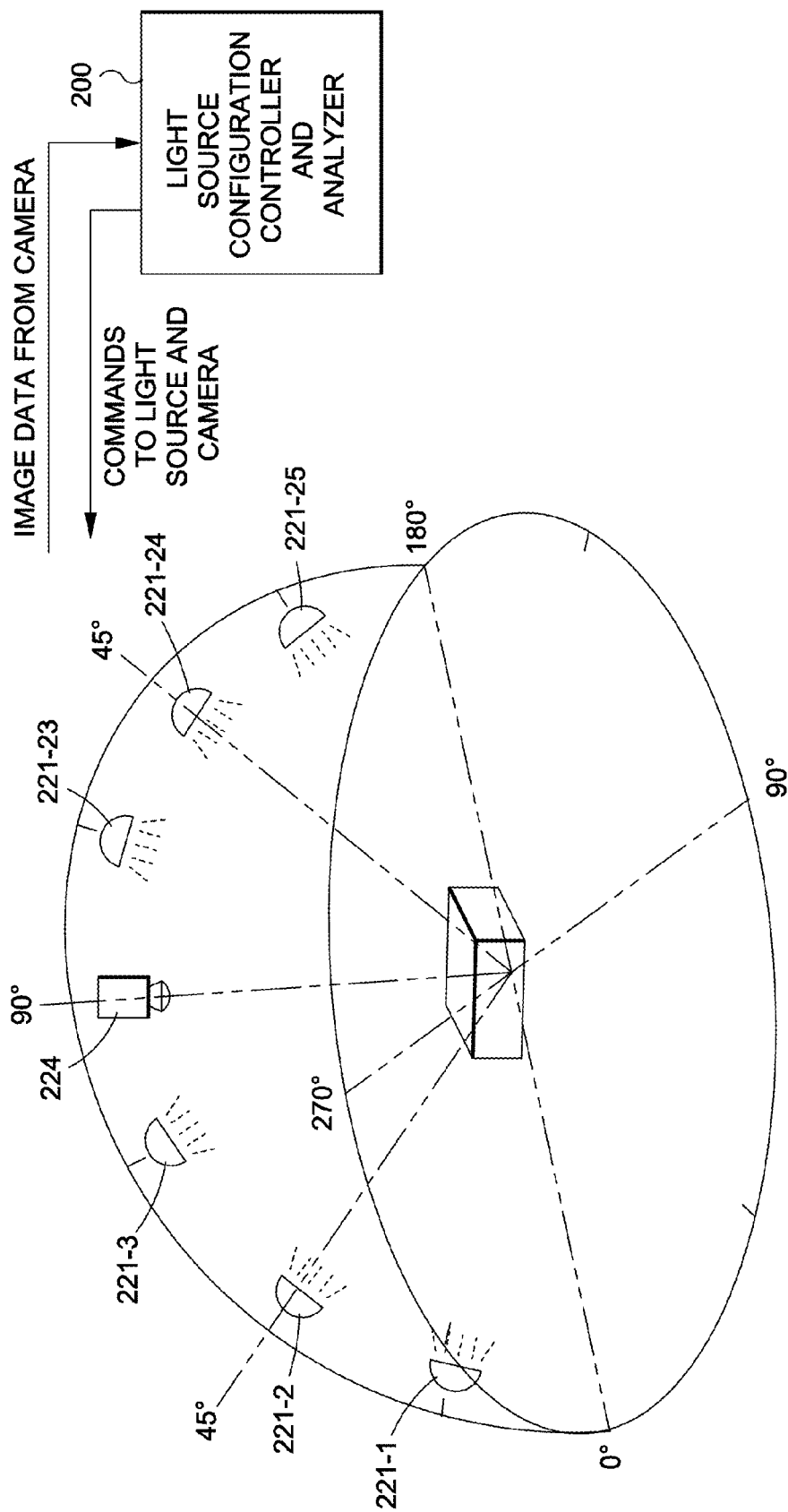
FIG. 4 illustrates an embodiment in which a training sample of objects fabricated from known materials is subjected to illumination from a large number of light sources at a respectively large number of incident angles.

In one example embodiment depicted in FIG. 4, there are twenty-five (25) light sources (221-1, 221-2, 221-3, . . . , 221-23, 221-24 and 221-25) arranged uniformly over a hemispherical dome surrounding a labeled object in the training sample, and one camera 224 positioned at a predetermined exitant angle such as 90 degrees elevation. Each light source may include six (6) differently-colored LEDs arranged in a circular cluster consisting of colors blue, green, yellow, red, orange and white, with white arranged at the center of the cluster. Each of the six (6) LEDs in each light source is illuminated independently, over all twenty-five (25) light sources, with the camera capturing an image of light reflected from the labeled training sample, for a total of one hundred and fifty (150) images for each labeled object in the training sample. After a similar capture of one hundred and fifty (150) images for each of the multiple labeled objects in the training set, feature vectors using the BRDF slices are derived (by application of a feature vector algorithm) for each captured image. The low-level feature vectors may be computed as the means of the intensities of the spectral BRDF slice images. The feature vectors may be obtained by application of a feature vector algorithm that computes the histogram over the clusters using all the spectral BRDF slices of a training sample. The distance metric can be the Euclidean distance, L1 or other appropriate metrics. The feature vectors are subjected to mathematical clustering so as to identify a small number of the better incident angles of the light sources, and/or the better spectral content thereof, with these mathematical clusters having the most significant aptitude for distinguishing between materials. The number of mathematical clusters should be relatively small; preferably, the number of clusters ranges between two and five clusters, inclusive. The number of mathematical clusters so-identified determines the number of light sources, the incident angles thereof, and their spectral content, for the classification system depicted in FIG. 1.

Likewise, the number of cameras, and the spectral sensitivity thereof, may also be determined by mathematical clustering. Again, the number of mathematical clusters as so-identified, and the spectral sensitivities thereof, are determinative of the number of cameras in the classification system depicted in FIG. 1, the exitant angle thereof, and their spectral sensitivities.

In one preferable arrangement, the spectral content of the light sources in the FIG. 4 embodiment is identical to the spectral content of a corresponding light source in the FIG. 1 classification system. Likewise, the spectral sensitivity of the camera is identical to that of the camera shown in the FIG. 1 classification system. It should be understood, however, that the spectral content of the light sources, and the spectral sensitivity of the camera, might in some embodiments be different.

In FIG. 4, for purposes of clarity and illustration, only six (6) light sources are depicted, at 221-1, 221-2, 221-3, 221-23, 221-24 and 221-25. In fact, in this embodiment, there are a total of twenty-five (25) light sources arranged uniformly over a hemispherical dome surrounding the labeled object in the training sample.

Figure 5:
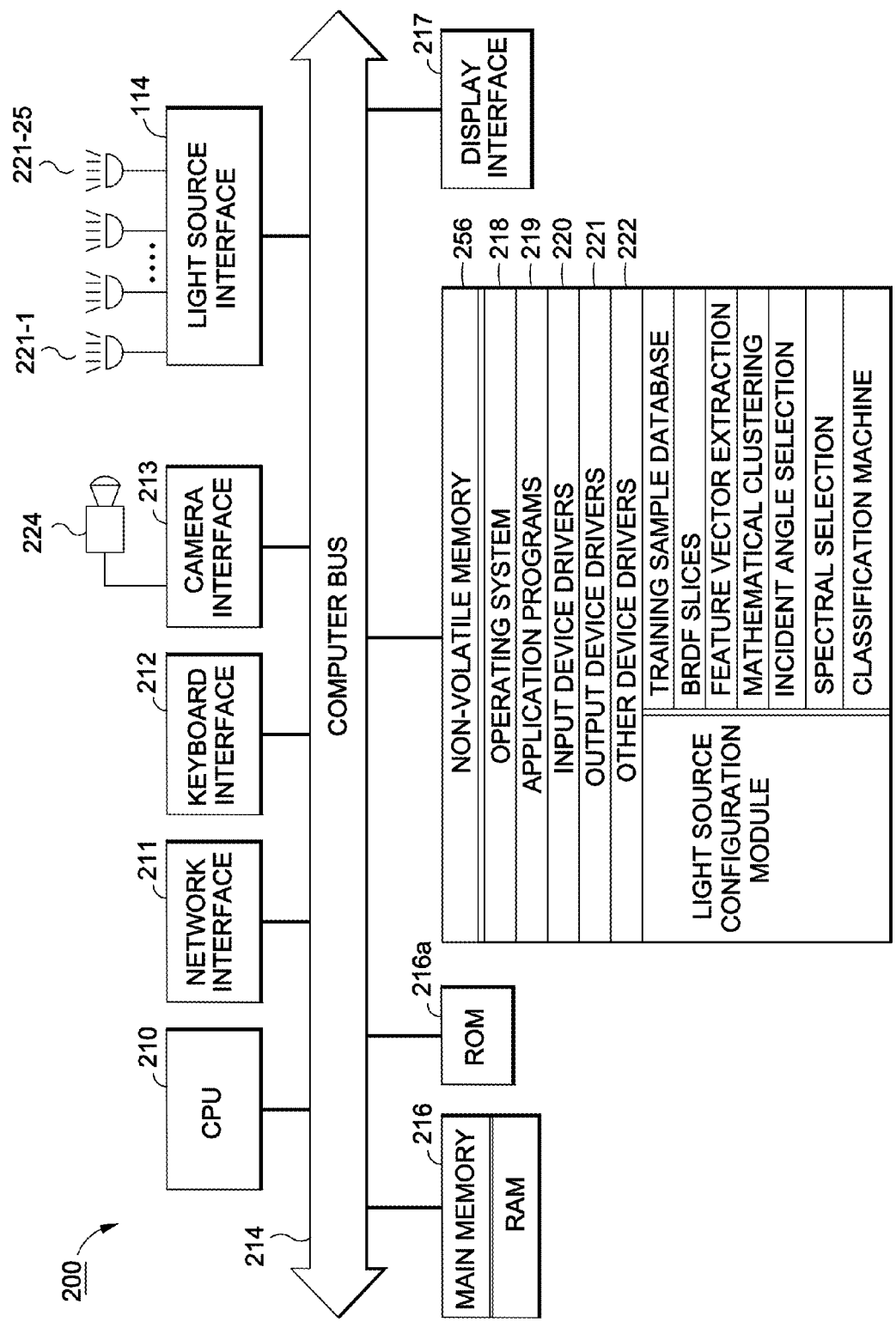
FIG. 5 is a view for explaining the architecture of a controller and analyzer for light source configurations.

Operation of the FIG. 4 embodiment proceeds under control of the light source configuration controller and analyzer 200. FIG. 5 illustrates more details concerning the internal architecture of light source configuration controller and analyzer 200.

As shown in FIG. 5, light source configuration controller and analyzer 200 includes central processing unit (CPU) 210 which interfaces with computer bus 214. Also interfacing with computer bus 214 are non-volatile memory 256 (e.g., a hard disk or other nonvolatile storage medium), network interface 211, keyboard interface 212, camera interface 213, random access memory (RAM) 216 for use as a main run-time transient memory, read only memory (ROM) 216*a*, and display interface 217 for a display screen or other output.

RAM 216 interfaces with computer bus 214 so as to provide information stored in RAM 216 to CPU 210 during execution of the instructions in software programs, such as an operating system, application programs, image processing modules, and device drivers. More specifically, CPU 210 first loads computer-executable process steps from non-volatile memory 256, or another storage device into a region of RAM 216. CPU 210 can then execute the stored process steps from RAM 216 in order to execute the loaded computer-executable process steps. Data, also, can be stored in RAM 216 so that the data can be accessed by CPU 210 during the execution of the computer-executable software programs, to the extent that such software programs have a need to access and/or modify the data.

As also shown in FIG. 5, non-volatile memory 256 contains computer-executable process steps for operating system 218, and application programs 219, such as graphic image management programs. Non-volatile memory 256 also contains computer-executable process steps for device drivers for software interface to devices, such as input device drivers 220, output device drivers 221, and other device drivers 222.

Non-volatile memory 256 also stores a light source configuration module. The light source configuration module comprises computer-executable process steps for determining, from the superset of all incident angles and spectral content of all light sources, which in this embodiment is twenty-five (25) light sources, and from the superset of all exitant angles and spectral sensitivities of all cameras, which in this embodiment is a single camera, a satisfactory subset by which material classification of an object fabricated from an unknown material may be made accurately and without any significant loss in accuracy as compared to material classification made by the superset.

The computer-executable process steps for these modules may be configured as part of operating system 218, as part of an output device driver in output device drivers 221, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The light source configuration module includes a corresponding plurality of modules including a module for storing a database of the labeled training sample, a module for calculation and storage of the BRDF slices, a module for extracting feature vectors in accordance with application of an algorithm for feature vectors, a module for performing mathematical clustering, a module to select incident angles for each mathematical cluster identified by the mathematical clustering algorithm, a module for selecting spectral content of light sources, and a module for storing and training a classification machine.

Figure 6:
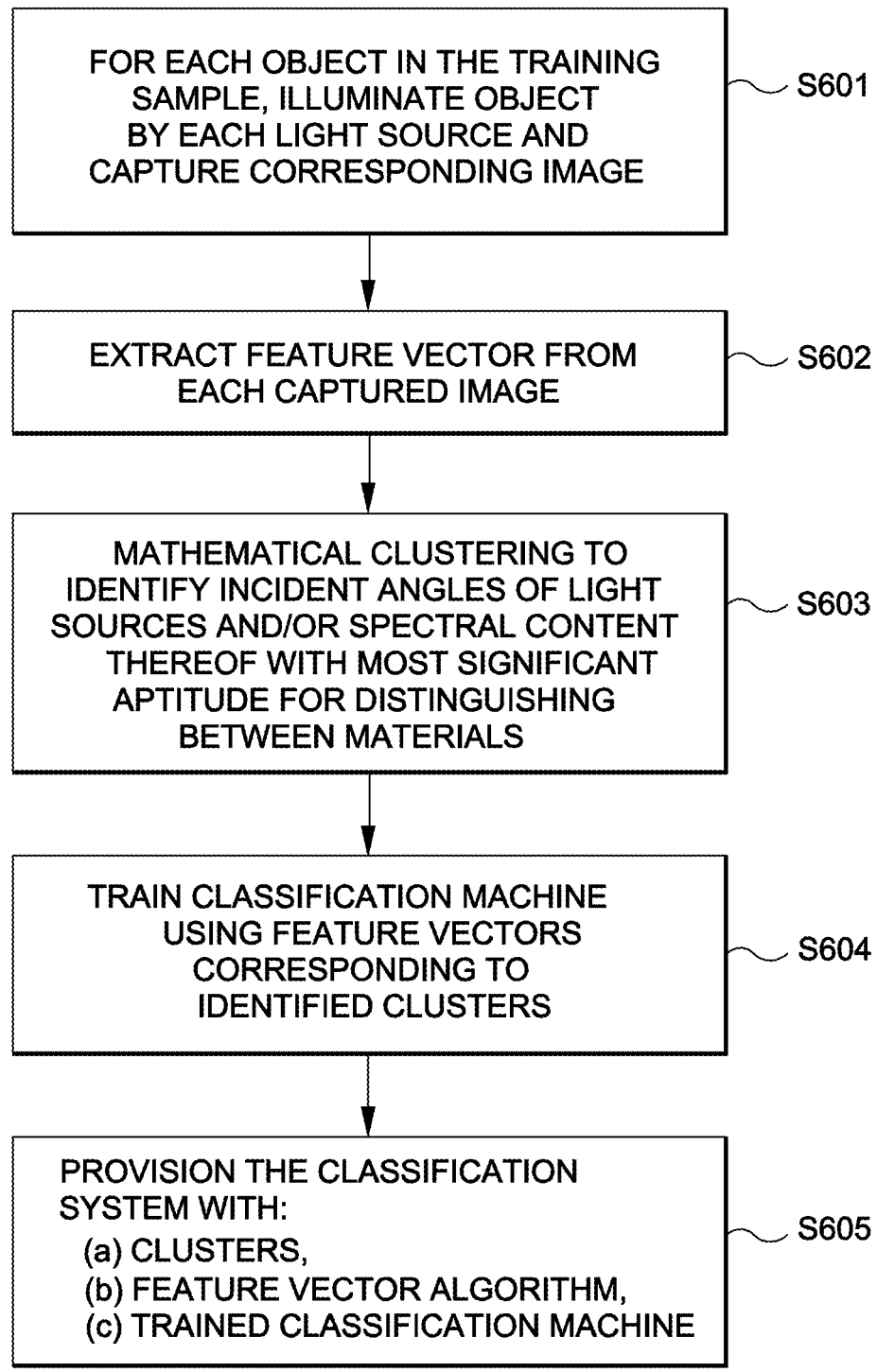
FIG. 6 is a flow diagram illustrating the general flow of processing performed by an embodiment of a light source configuration controller and analyzer.

FIG. 6 is a flow diagram illustrating the general flow of processing performed by light source configuration controller and analyzer 200. In step S601, for each labeled object in the training sample the object is illuminated in turn by each of the twenty-five (25) light sources 221-1 ... 221-25, and individually and independently for each of the six (6) differently-colored LEDs in each such light source, with a corresponding image being captured at the exitant angle by camera 224. After all labeled objects in the training sample have been illuminated, and corresponding images captured, step S602 calculates BRDF slices and extracts feature vectors from each captured image. The nature of the feature vectors is described below in connection with FIG. 7. In general, the nature of the feature vectors depends on the nature of the classification challenge, and might include, for example, feature vectors extracted by application of a histogram-based feature vector algorithm.

In step S603, mathematical clustering is performed on the extracted feature vectors, so as to identify clusters of incident angles for the light sources, and/or spectral content thereof, with the most significant aptitude for distinguishing between materials. The nature of the mathematical clustering might include, for example, K-means clustering. The mathematical clustering is performed so as to identify two or three mathematically significant clusters of data for a corresponding two or three incident illumination angles.

The clusters identified in step S603 might not correspond to actual incident angles of any one of the twenty-five (25) light sources. Likewise, if clustering is performed for spectral content, the mathematical clusters might not correspond exactly to the actual spectral content of the light sources. In such cases, the actual light sources and spectral content closest to the mathematical clusters, and the feature vectors corresponding to these actual locations and spectral content, are selected for further processing.

In step S604, a classification machine is trained using feature vectors corresponding to the identified clusters. The classification machine might include an SVM (support vector machine) algorithm.

In step S605, a classification system such as that depicted in FIG. 1 is provisioned with the results. In particular, the classification system is provisioned with the clusters identified by the mathematical clustering, the algorithms selected for extraction of feature vectors, and the trained classification machine. Thereafter, and returning to the classification system depicted in FIG. 1, given an object fabricated from an unknown material, the classification system of FIG. 1 illuminates the object with light sources whose incident angle and/or spectral content are determined in step S603, and images from each illumination are captured by camera 24. In this embodiment, camera 24 is positioned at an exitant angle identical to that of camera 224, and the spectral sensitivity of camera 24 is identical to that of camera 224. In other embodiments, where mathematical clustering is performed so as to identify an optimal position or positions for camera(s) 24, or spectral sensitivities for such camera, camera(s) 24 is positioned at an exitant angle in accordance with the mathematical clustering, and its spectral sensitivity is matched to that of the mathematical clustering.

Thereafter, based on the captured image data, the classification system of FIG. 1 applies the feature vector algorithm provisioned in step S605, so as to derive BRDF slices and other feature vectors from the captured images. The feature vectors as so-calculated are fed to the trained classification machine, so as to result in a classification of material for the illuminated object.

Figure 7:
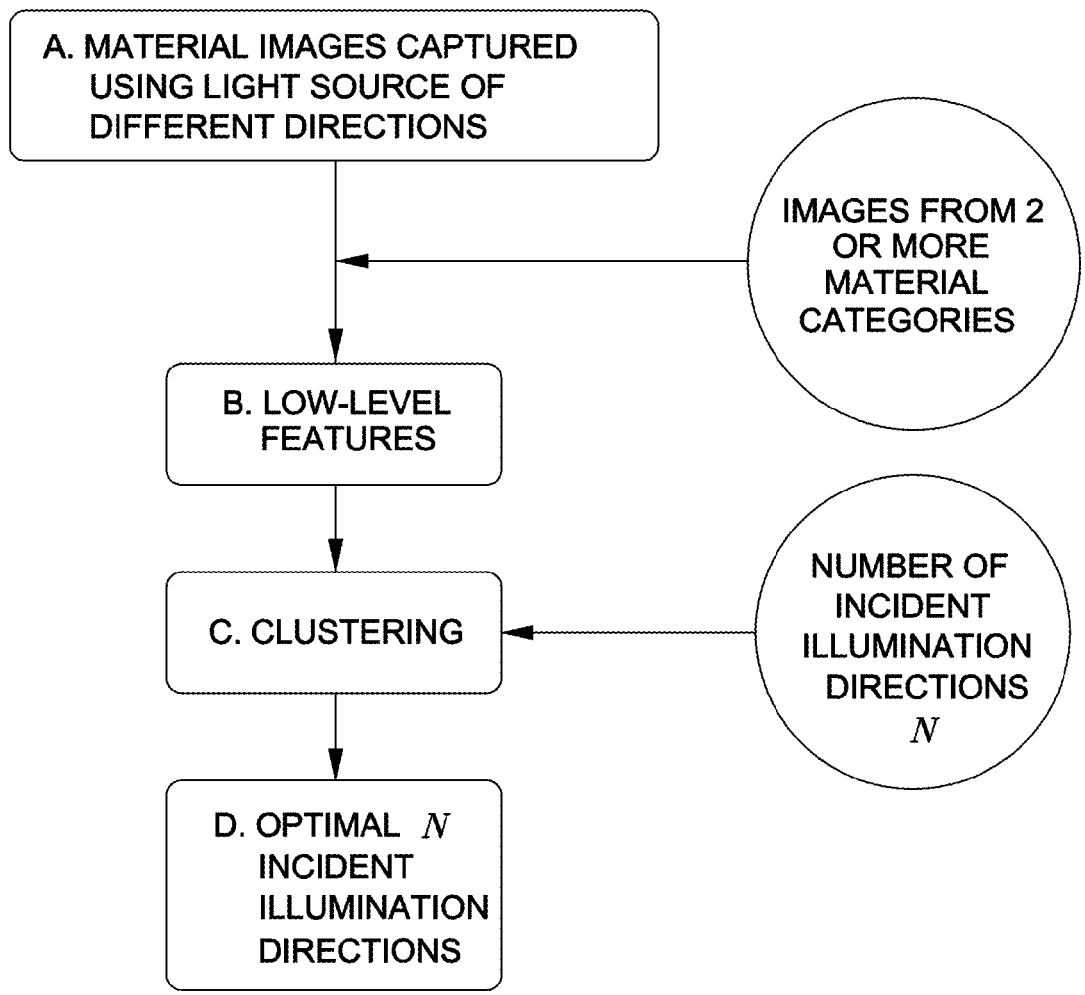
FIGS. 7 and 8 are views illustrating a framework for a determination of the incident angle for plural light sources used for material classification, and for a determination of the number of light sources, according to an embodiment described herein.

FIG. 7 illustrates a further embodiment of a light source configuration controller and analyzer. This further embodiment is somewhat more specifically tailored to the classification of different types of metals, using the dataset published by Gu in connection with citation [3].

It is again appropriate to note that approaches previously considered for spectral BRDF-based features for material classification use large numbers of sight sources and corresponding image captures, such as 150 LEDs for capturing the material images. As described previously, the LEDs are clustered into groups of six (6) LEDs each, yielding twenty-five (25) clusters in total. Building a dome with 150 LEDs to deploy in a factory or other industrial robotic application setting is cumbersome and difficult to maintain. In this description, therefore, there is a selection of the most discriminative LED clusters, corresponding to incident illumination angles, which would be sufficient to image and to classify a set of given materials. With this approach, as few as only 2 or 3 LED clusters or incident illumination angles (12 or 18 spectral BRDF slices) can be used, while not compromising on the accuracy of material classification.

In this discussion, it is assumed that all LEDs in one cluster have the same incident illumination angle. This is a valid assumption since the difference in the incident angle illumination for the LEDs is very small and can be attributed to noise in a real-world setting. It is also an appropriate assumption given that this explanation is using LED clusters specific to the type of data provided by Gu in his dataset. It is possible that each light source or some of them might include only a single LED and not a cluster of LEDs. In such a case, clustering of the spectra for the light sources might not be applicable.

The framework of this embodiment is shown in FIG. 7, which illustrates a framework for selecting incident illumination angles using spectral BRDFs for material classification. In a first explanation, the steps of the framework are described. In a second explanation, there is a description of how different feature vectors can be computed using the optimal LED clusters or incident illumination angles. One type of feature requires only 12 or 18 spectral BRDF slices. The second type is computed using all 150 spectral BRDF slices in addition to the optimal LED clusters or incident illumination angles. A verification is provided using the dataset given by Gu at citation [3], to the effect that the feature vectors computed using the optimal incident illumination angles provide competitive accuracy in material classification, in the sense that by using a subset of only two or three (first number) light sources at incident angles determined by mathematical clustering, material classification can be achieved at an accuracy not significantly worse than the accuracy provided by the superset of all twenty-five (25) (second number) light sources.

The steps of the framework depicted in FIG. 7 will now be explained (i.e., the first explanation mentioned above).

At (A) in FIG. 7, the images are obtained from the RIT dataset given by Gu in connection with citation [3] (see <http://compimg1.cis.rit.edu/data/metal/>). This dataset contains 10 samples in each of 10 material categories to add up to 100 samples in total. Each material sample is imaged 150 times using each of the LEDs of the dome as described previously. Thus, at (A), images are obtained corresponding to images of materials captured using light sources of different directions.

At (B) of FIG. 7, given the training samples belonging to material categories for which the optimal set of incident illumination angles will be computed, the low-level features are computed. These are denoted by X={$x_t$, where t=1 ... T}, where $x_t$ is the feature, in this case the mean value, for one slice and T=150 is the number of slices. For each material sample, the mean over all the pixels of a cropped region is taken for each of the 150 slices. The features are concatenated yielding a 150 D (dimensional) feature vector for each material.

At (C) of FIG. 7, the incident illumination angles to be selected correspond to those of the LED clusters in the imaging setup. The number of LED clusters N is inputted by the user. Given a set of training samples belonging to one material category, all the 150 D low-level feature vectors as described in (B) for each material are placed into 25×M matrices. M is the number of LEDs in each cluster, which is 6 in this case. Next the aggregated low-level features for all the training data are clustered into N clusters, since one purpose of this framework is to select the N LED clusters. Note that there is a slight difference between the terms "clusters" and "LED cluster(s)" as referred to in this document. The former refers to the mathematical clusters as computed by the mathematical clustering algorithm, while the latter refers to the actual clusters of LEDs in the imaging setup dome. The 25×M matrices for each material are used to perform K-means clustering or Gaussian Mixture Models clustering to obtain the most representative N clusters of the data. As such, the set of means for the clusters, $\mu_i$ where i= 1 ... N, is obtained where each mean $\mu_i$ is of dimension M. In other embodiment, a convex clustering algorithm can be used, whereby the number of most representative clusters N is automatically determined by the algorithm.

At (D) of FIG. 7, given the cluster means as computed in (C), the N optimal LED clusters from the imaging dome are then selected. Each cluster mean is used to search through the 25×M matrices for all material samples to find the LED cluster with minimum distance to it. The angle corresponding to the intensity values in the M dimensional row of the matrix would be the optimal angle. The same is repeated for obtaining the remainder of the optimal LED clusters, resulting in a subset of N optimal directions for incident illumination.

Figure 8:
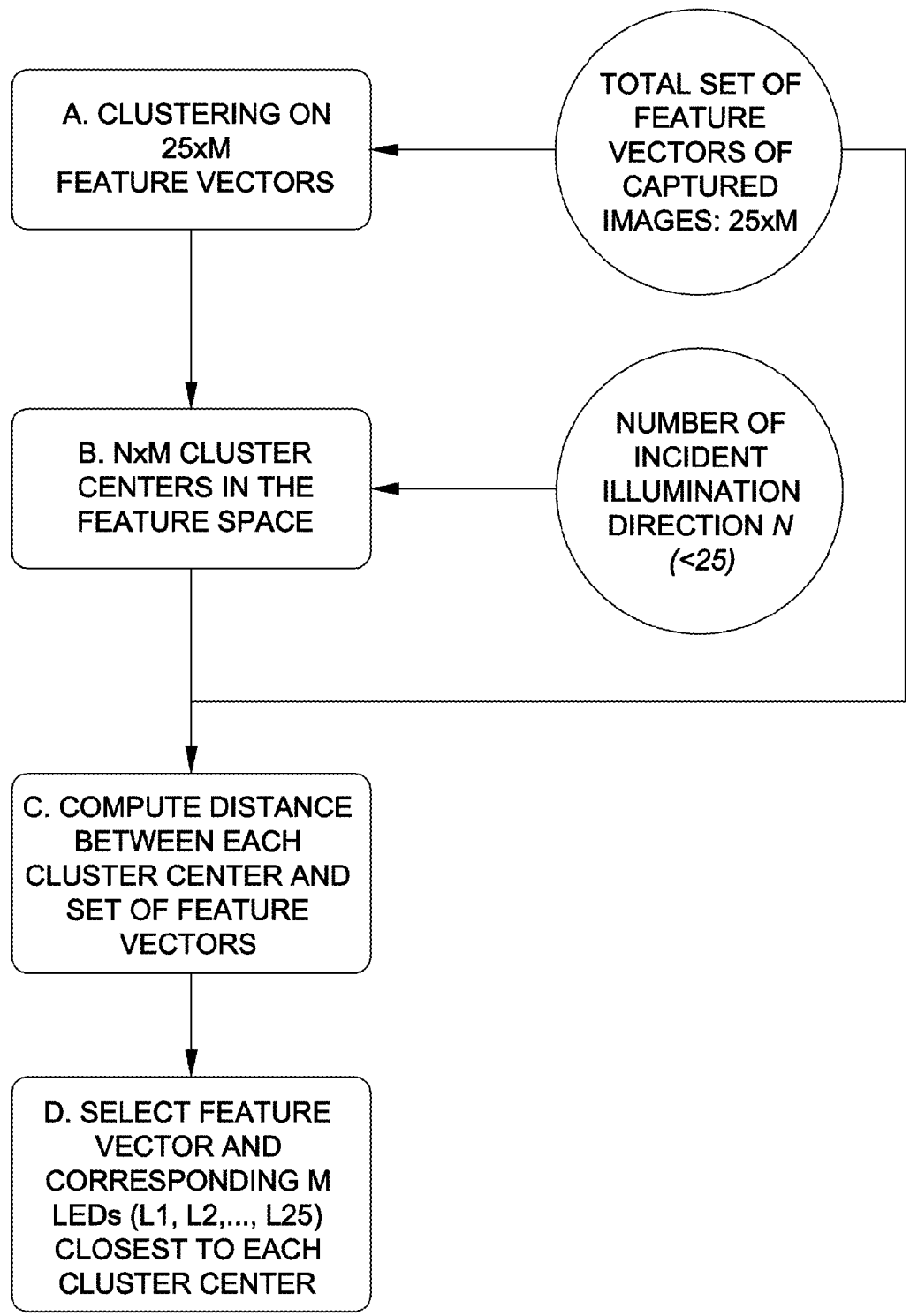

FIG. 8 is another view for explaining the framework of this embodiment, and is largely the same as the framework illustrated in FIG. 7. In FIG. 8, the variable M represents the number of different-colored spectral sources in each different light source. For example, referring to the hemispherical dome arrangement shown in FIG. 4, there may be twenty-five (25) light sources (221-1, 221-2, 221-3, ..., 221-23, 221-24 and 221-25) arranged uniformly over a hemispherical dome, where each light source may include six (6) differently-colored LEDs arranged in a circular cluster consisting of colors blue, green, yellow, red, orange and white, with white arranged at the center of the cluster. In such an arrangement, M=6. It will be understood that M=6 is a non-limiting example, and that other values for M are possible, in correspondence to the constitution and arrangement of illumination light sources by which the training set is built.

Likewise, in FIG. 8, the variable N represents the desired number of different incident illumination directions for each different light source in the classification engine. More specifically, it is understood that according to the framework described herein, there is a selection of a subset of illumination angles for only a few light sources from a superset of illumination angles for many such light sources. For example, referring again to the hemispherical dome arrangement shown in FIG. 4, there may be twenty-five (25) light sources in the superset of light sources, but a subset of only three (3) such light sources is desired for the classification engine. In such an arrangement, N=3. It will be understood that N=3 is a non-limiting example, and that other values for N are possible, in correspondence to the constitution and arrangement of illumination light sources by which the training set is built, and in correspondence to the desired number of different incident illumination directions in the subset of illumination angles. The value of N in all cases is expected to be less than the number of illumination angles in the superset of light sources, such that in this example embodiment, N<25.

Turning more specifically to FIG. 8, a framework is illustrated for selecting N incident illumination angles using spectral BRDFs for material classification. At (a) in FIG. 8, there is clustering on the total set of feature vectors of captured images in the training set. In this example embodiment, which uses the images are obtained from the RIT dataset given by Gu in connection with citation [3] (see <http://compimg1.cis.rit.edu/data/metal/>), the dataset contains 10 samples in each of 10 main material categories to add up to 100 samples in total. Each material sample is imaged 150 times, once for each of the M=6 LEDs of the 25 illumination sources as described previously. Thus, there are 15000 images in the training database, where 15000=25×6 (i.e., M=6 LEDs)×100 (i.e., the number of samples). Feature vectors are developed for the captured images, and at (a) there is clustering on 25×M feature-vectors. The feature-vectors may be obtained by application of a feature vector algorithm, the mean computation in this case, on each of the spectral BRDF slices of a training sample.

At (b) of FIG. 8, given the number N of desired illumination angles, there is a determination of N M-dimensional cluster centers (N cluster centers of dimension M) in the feature space. More precisely, given the 25×M set of feature vectors for each training sample (for example, Aluminum1, Aluminum2, and so on, for the Aluminum material category and Copper1, Copper2, and so on, for the Copper material category) from (a), N M-dimensional clusters are determined, and the respective centers of each such cluster are thereafter determined in the feature space.

At (c) of FIG. 8, a distance is calculated between each of the N M-dimensional cluster centers (from (b) of FIG. 8) and each of the 25 M-dimensional feature vectors (from (a) of FIG. 8). One purpose of computing these distances is to allow selection of the M-dimensional feature vectors closest to the centers, as these selected M-dimensional feature vectors correspond to illumination light sources in the superset of light sources that can be selected as the subset of illumination light sources for the classification engine. The distance metric can be the Euclidean distance, L1 or other appropriate metrics.

At (d) of FIG. 8, given the distances computed at (c), the respective M-dimensional feature vectors closest to each cluster center are selected. Correspondingly, for each cluster center, there is a selection of the M LEDs in the light source corresponding to the selected M-dimensional feature vector, thus resulting in selection of a subset of N illumination angles for only a few light sources (first number of light sources) from a superset (here, 25) of illumination angles for many such light sources (second number of light sources).

A description will now be made as to how different feature vectors can be computed using the optimal LED clusters or incident illumination angles, and as to how feature vector computation and classification proceeds in this embodiment (i.e., the second explanation mentioned above).

Given a set of labeled training samples belonging to 2 different material categories, and the optimal N LED clusters (or incident illumination angles) as described in the previous section, the set of feature vectors can now be obtained which uses only N LED clusters. These are taken to be the low-level feature vectors computed using the spectral BRDF slices taken using the N×M-LED clusters. In the case of 2 LED clusters, a material sample would be represented by a 12 D feature vector, for example, since there are M=6 LEDs in each cluster. This type of feature vector, and the algorithm therefor, is referred to as the "optimal" one, even though it might not be optimal in a strict mathematical sense.

A second type of feature vector considered is a high-level one. It is computed using the low-level features corresponding to the 150 spectral BRDF slices corresponding to all the LEDs, as described in (B) in the previous section. The approach used is similar in nature to the Bag-Of-Visual Words one used commonly in computer vision for image classification tasks. In this case, given the N clusters as computed in (C) of the previous section, a histogram over the clusters is computed for each material sample using its BRDF slices. For each of the 25×M aggregated features for one material, the distance is computed to each of the cluster means. Two types of distance measures are considered: the Euclidean distance (ED) and the L1. The histogram bin corresponding to the smallest distance measure is incremented by one. Therefore each material sample would be represented by a histogram of occurrence of the optimal clusters. As such, a material sample would be represented by an N-dimensional vector. Note again that the clusters from the previous section referred to here are obtained from (C) and not (D). This type of feature vector, and the algorithm therefor, is referred to as "histogram-based".

The third type of feature vector tested in the classification algorithm is the low-level feature vector as described in (B) above. This type of feature vector, and the algorithm therefor, is referred to as the "mean" one.

A classification engine is then trained on multiple folds of training data and tested on the remaining folds. In the case of two material categories, where there are four (4) samples per category (8 samples in total), there would be 16 folds of training and testing data. For each fold, a training set would have 6 material samples, while a test set would have 2 samples. The classification accuracy computed is then taken to be the average over the test sets of the 16 folds. The classification engine can be either discriminative or generative. This embodiment uses an SVM (Support Vector Machine) classification engine, which is a discriminative classifier. Two items need to be set when using an SVM: the kernel type and the C parameter. Since the RIT dataset contains only a small number of training samples, use of a linear kernel is sufficient. However, in an alternate embodiment, an SVM classification engine was used with a radial kernel, with no significant difference (better or worse) in the results. As for the parameter C, it was set to 10.

A comparison was made amongst the results for the 3 feature vector representations described above. Tests were on the separation of aluminum versus copper, as well as the separation of brass versus copper. Table A shows the classification accuracies using the 3 types of feature vectors described for the aluminum and copper categories, where the number of optimal clusters selected is N=2 and N=3, respectively. Table B shows the classification accuracies using the 3 types of feature vectors described for the brass and copper categories, where the number of optimal clusters selected is N=2 and N=3, respectively. The best results obtained for each of the separation cases are highlighted by arrows surrounding the name of the feature vector algorithm that provides the best results, for example, "--> Optimal (18 D) <--".

TABLE A

| Feature Vector Type | Number of light sources | Aluminum (%) | Copper (%) | Overall (%) |
|---|---|---|---|---|
| Optimal (12D) | 2 | 81 | 75 | 78 |
| Histogram-based, using ED metric (2D) | 2 | 75 | 100 | 88 |
| Histogram-based, using L1 metric (2D) | 2 | 75 | 88 | 81 |
| --> Optimal (18D) <-- (best results) | 3 | 94 | 94 | 94 |
| Histogram-based, using ED metric (3D) | 3 | 81 | 94 | 88 |
| Histogram-based, using L1 metric (3D) | 3 | 94 | 94 | 94 |
| Mean (150D) | 25 | 75 | 81 | 78 |

Table A: Classification accuracies using the 3 types of feature vectors described for the aluminum and copper categories, where the number of optimal clusters selected is N=2 (for the top four rows), and where the number of optimal clusters selected is N=3 (for the bottom four rows).

Table A thus shows classification accuracies obtained using an SVM with a linear kernel, for each of the aluminum, copper and then both categories, computed over 16 folds. Three types of feature vectors are considered: the optimal where the feature vectors are computed as the mean ones over the BRDF slices corresponding to the optimal LED clusters; the histogram-based where the feature vectors are computed as the number of occurrences of the estimated N clusters using the Euclidean distance metric and the L1 metric; and the mean feature vector computed as the concatenation of the means over all 150 slices. The number of selected clusters in this case is N=2 for the top four rows, and N=3 for the bottom four rows, as indicated in the table.

TABLE B

| Feature Vector Type | Number of light sources | Brass (%) | Copper (%) | Overall (%) |
|---|---|---|---|---|
| --> Optimal (12D) <-- (best results) | 2 | 100 | 94 | 97 |
| Histogram-based, using ED metric (2D) | 2 | 81 | 94 | 88 |
| Histogram-based, using L1 metric (2D) | 2 | 75 | 100 | 88 |
| Optimal (18D) | 3 | 75 | 100 | 88 |
| Histogram-based, using ED metric (3D) | 3 | 56 | 94 | 75 |
| Histogram-based, using L1 metric (3D) | 3 | 75 | 94 | 84 |
| Mean (150D) | 25 | 81 | 100 | 91 |

Table B: Classification accuracies using the 3 types of feature vectors described for the brass and copper categories, where the number of optimal clusters selected is N=2 (for the top four rows), and where the number of optimal clusters selected is N=3 (for the bottom four rows).

Table B thus shows classification accuracies obtained using an SVM with a linear kernel, for each of the brass, copper and then both categories, computed over 16 folds. Three types of feature vectors are considered: the optimal where the feature vectors are computed as the mean ones over the BRDF slices corresponding to the optimal LED clusters; the histogram-based where the feature vectors are computed as the number of occurrences of the estimated N clusters using the Euclidean distance metric and the L1 metric; and the mean feature vector computed as the concatenation of the means over all 150 slices. The number of selected clusters in this case is N=2, for the top four rows, and N=3 for the bottom four rows, as indicated in the table.

Generally, accuracy percentages listed in Tables A and B are calculated by dividing the number of correctly classified test samples by the total number of test samples. For example, in the case of 10 brass test samples, if the number of test samples correctly classified as brass is 6 and the total number of brass samples is 10, the classification accuracy is 60%. Furthermore, for purposes of this description, the classification accuracy was computed sixteen (16) times for different combinations of training and test samples. Therefore the classification accuracies reported in the tables are the means over the accuracies computed for all the folds. This is a metric commonly used in the art, for evaluating classification algorithms.

Representative incidence angles found for the light sources, for each case, are set out below. Each angle is given using three (3) coordinates in degrees. Each coordinate is the angle between the radius vector and one of the three coordinate axes. The radius vector is drawn from the (0, 0, 0) center to the light source.

Aluminum Versus Copper:
N=2: (118°, 84°, 29°) and (119°, 70°, 36°)
N=3: (116°, 84°, 27°), (119°, 70°, 36°), and (63°, 46°, 55°)
Brass Versus Copper:
N=2: (119°, 70°, 36°), (63°, 46°, 55°)
N=3: (119°, 70°, 36°), (63°, 46°, 55°), and (102°, 88°, 13°)

As noted above, the classification engine used in this embodiment is an SVM-based classification engine. As compared to the classification considered by Gu in citation [2], citation [2] uses two classification algorithms, one of which is SVM-based. The description of classification engines herein does not compare directly to the classification used by Gu in citation [2] for the reason that Gu uses the optimal two shots (as computed by their algorithm) to capture the images they use in classification. Therefore they capture only two images of their materials with different combinations of LEDs; however they do not provide these images. They only provide images taken under each LED independently, so 150 images captured under 150 LEDs. Furthermore, their classification treats each pixel as a sample independently, while the classification engine herein takes each stack of 150 images for one material to be one sample. Experiments were performed on per-pixel classification of material samples but results of those experiments are not included herein at least in part for the reasons listed above.

With respect to the incident illumination angles corresponding to the optimally-selected light sources, the optimal clusters or their corresponding angles are selected from the original ones in the dome, which has 25 LED clusters or equivalently 25 angles in total. The optimal angles computed by the algorithm proposed in the MOI are different for different sets of materials. For a given set of training samples, K-means clustering is performed to obtain N=2 or N=3 clusters of angles. These clusters are estimated by the K-means algorithm and therefore their means do not directly correspond to any of the angles in the dome. Afterwards (in step (D) of the FIG. 7 workflow) the cluster means are mapped to the angles of the dome using a minimum distance metric.

As shown in the above Table A, N=3 is apparently better than N=2 for the classification of aluminum versus copper, which seems consistent with intuitive expectations. On the other hand, as shown in the above Table B, N=2 is apparently better than N=3 for classification of brass versus copper, which seems to be a non-intuitive result since it might be expected that a larger number of N is better than smaller number of N. From a physical standpoint, it might indeed be expected that the case of N=3 should be better than the case N=2. However, the mathematical clustering technique is data-driven. Therefore, it learns its parameters based on a set of input data, and then classifies test data. Additionally, the parameter C which is set manually also plays a role in the parameter estimation (or learning) process. This is generally the case in machine learning algorithms. Although the value of the parameter C was varied experimentally, and automatically, the results did not differ significantly. It is thought that the non-intuitive result of better classification at N=2 as compared with N=3 might be attributed to the fact that in machine learning, sometimes increasing the dimensionality of the feature space does not necessarily result in a better classification algorithm.

Among the conclusions that might be drawn from these results are the following two conclusions. First, the optimal number of illumination angles is at least partly dependent on the material categories considered, as expected. For separating aluminum from copper, the case of N=3 consistently provides classification performance on par with or superior to the case of N=2. For separating brass from copper, the case of N=2 consistently provides classification performance on par with or superior to the case of N=3. Second, it can generally be concluded that the classification accuracies using the optimal feature vectors are generally superior to the accuracies when using other types of feature vectors. The optimal feature vectors correspond to the incident illumination angles selected by the mathematical clustering approach described herein.

Among the advantages provided by the embodiments and description herein is the advantage of determining a minimal subset of light sources from among a superset of light sources, and corresponding incident illumination angles, which can be used to image materials without compromising on material classification accuracy. As the number of light sources increases, there is a geometric increase in the complexity of building, maintaining and using a material classification system, and a geometric increase in the time and processing power required for accurate classification results.

Other advantages include a reduction in the number of images captured and consequently the dimensionality of the feature vectors needed to represent the materials in the classification algorithm. This would result in decreasing both the training and test time. Decreasing the training time would be useful in case of deployment of an online training material classifier. Decreasing the test time can be important when a classifier is deployed in a factory setting for recycling.

FIGS. 9 to 21 illustrate techniques for material classification with selection of spectral bands using spectral BRDF slice images captured under multiplexed illumination for material classification, and may comprise analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials.

Figure 9:
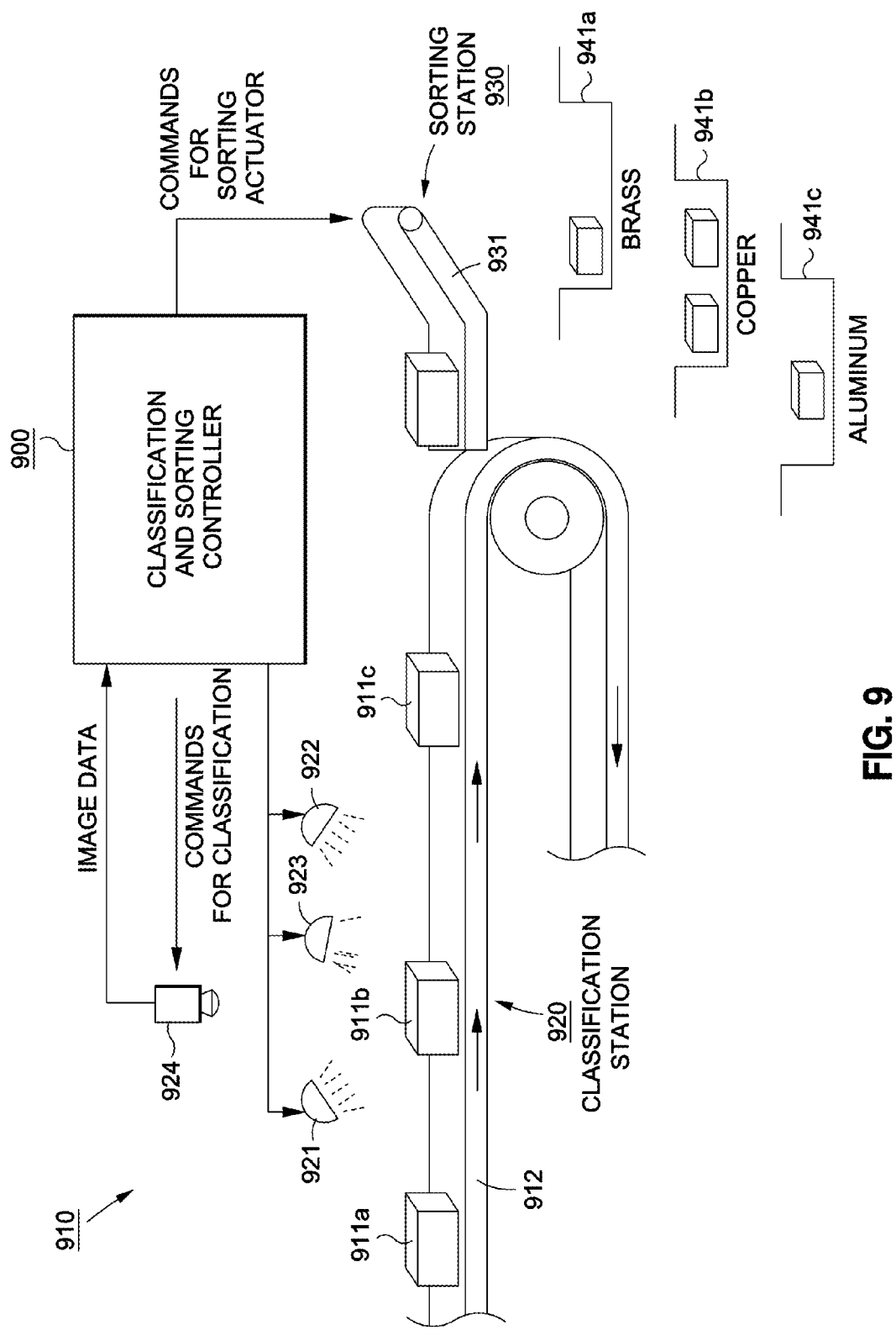
FIG. 9 is an example embodiment of a classification system according to the description herein, in the form of a robotic industrial inspection system.

FIG. 9 is an example embodiment of another classification system according to the description herein, in the form of an industrial inspection system such as a recycling system in which objects to be recycled are classified according to the materials from which the objects are fabricated, and the classified objects are sorted for recycling according to their material classification.

As shown in FIG. 9, objects 911a, 911b, etc. are conveyed on a conveyor mechanism 912 to a classification station 920, where the objects are classified according to their material, and thence to a sorting station 930, where the objects are sorted according to their material classification. Classification station 920 includes plural broadband light sources 921, 922 and 923, together with a camera 924 for capturing images of objects positioned at classification station 920. The object at the classification station is illuminated by multiplexed illumination by simultaneously using all of the plural broadband light sources under control of classification and sorting controller 900, and camera 924 captures one or more images for each multiplexed illumination. Under control of the classification and sorting controller 900, a classification is made for the material from which the object is fabricated.

Camera 924 is a multi-spectral capture camera, capable of capturing images in each of plural spectral bands which are narrow, such as in each of 32 spectral bands ranging from 410 nm to 720 nm with an interval of 10 nm. For example, camera 924 may be a broad-band capture camera with a tunable filter positioned before it, such as a liquid crystal tunable filter (LCTF) with 32 spectral bands ranging from 410 nm to 720 nm with an interval of 10 nm.

More preferably, however, while being a multi-spectral capture camera, capable of capturing images in each of plural spectral bands which are narrow, camera 924 does not necessarily have the capability of capturing images in all 32 spectral bands ranging from 410 nm to 720 nm with an interval of 10 nm. Rather, camera 924 more preferably is equipped to capture images in a subset of fewer than the 32 of spectral bands, such as a subset of 5 spectral bands. The precise identity of the spectral bands selected for the subset, and methodology by which the selection is effected, are both described in greater detail below, in connection with FIGS. 12 through 21.

Because camera 924 preferably captures images in only a subset of spectral bands (such as 5 spectral bands), the camera may be a relatively inexpensive camera since it is not necessary to capture all 32 spectral bands. As an example, the camera 924 may be implemented with a simple filter wheel in front of the camera, or in front of a light source which may be a broadband light source, with filters on the filter wheel corresponding in wavelength to the spectral bands selected for the subset.

Conveyor mechanism 912 continues to convey the object to sorting station 930, where sorting actuator 931 sorts the objects according to the material classification. Sorting is controlled by classification and sorting controller 900, which commands actuator mechanism 931 to sort the classified objects into multiple receptacles 941a, 941b and 941b.

In this example embodiment, material classification differentiates between different types of metals from which the objects are fabricated, such as brass, copper and aluminum. Naturally, it will be understood that this is a non-limiting example. In other embodiments, material classification could differentiate between metal, plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

A description will now be made of the spectral content of the light sources, of the angular positioning of the plural light sources and the camera relative to the object at the classification station, and of the spectral sensitivity of the camera.

Figure 10:
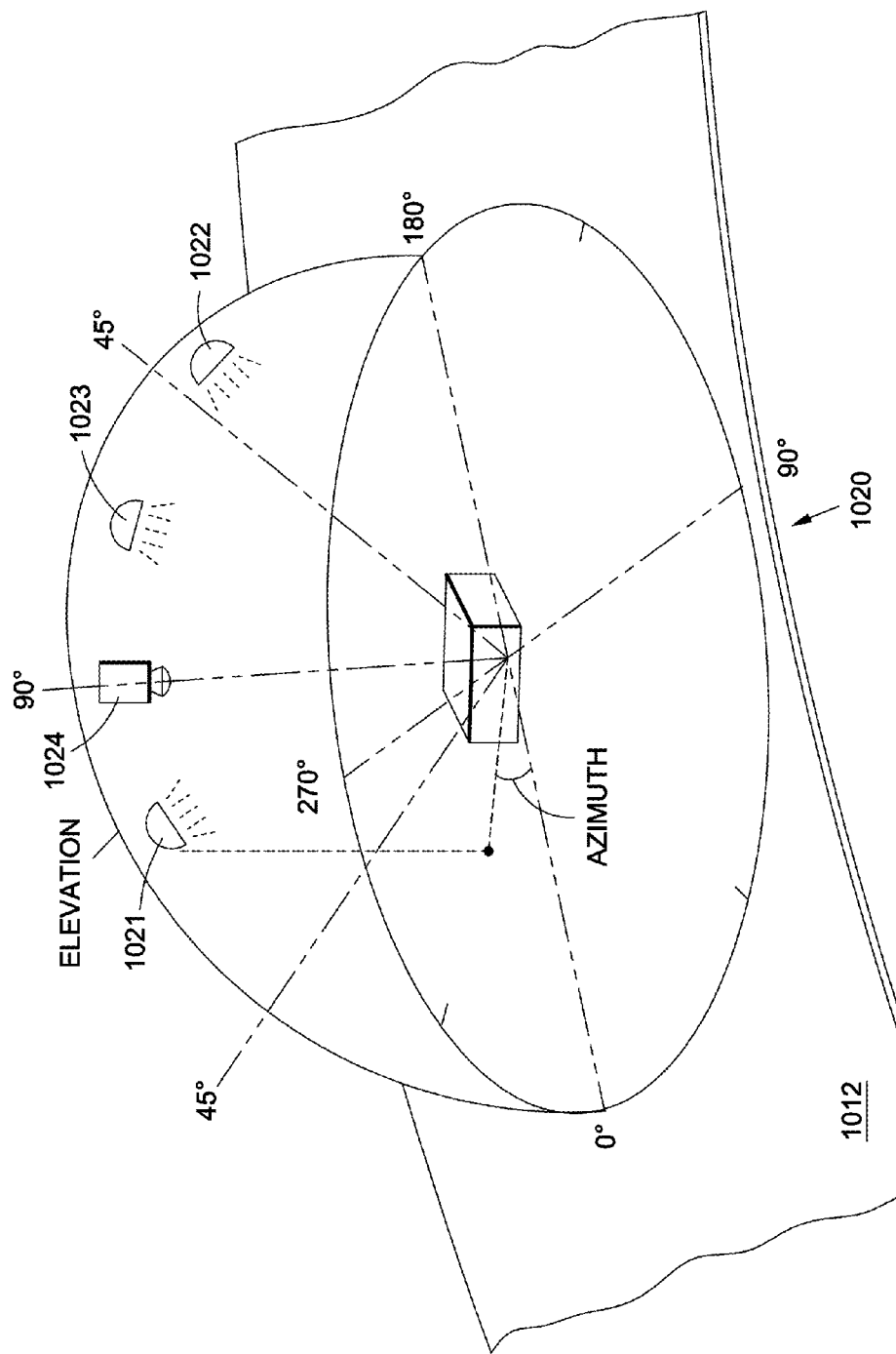
FIG. 10 is a more detailed view of an object on the conveyor mechanism of FIG. 9.

FIG. 10 is a more detailed view of an object being subjected to classification at a classification station of the FIG. 9 view. In FIG. 10, an object is positioned on conveyor mechanism 1012 at classification station 1020. Each of the light sources 1021, 1022 and 1023 has a broadband spectral content so as to provide multiplexed illumination of the object at classification station 1020. In multiplexed illumination, multiple light sources illuminate the object simultaneously from different directions.

In FIG. 10, an angular coordinate system has been superimposed for purposes of explanation, and for purposes of explaining the angle of incidence for each of light sources 1021, 1022 and 1023, and the angle of exitant for light reflected from the object and imaged by camera 1024. For purposes of illustration, the elevational and azimuthal angles of only one light source has been depicted, namely, the elevational and azimuthal angles of light source 1021, but it is to be understood that each of the light sources is positioned at respective elevational and azimuthal angles relative to the angular coordinate system. The light sources 1021, 1022 and 1023 may be positioned at incidence angles selected by any means that also provides discriminative illumination for the object under inspection using only a relatively few illumination light sources, such as only 2 to 5 light sources, so as to facilitate distinguishing between different classifications of materials. One preferred means for selecting incidence angles is described above.

In this example, camera 1024 is positioned at an exitant angle of 90 degrees elevation, but this is merely convenient and is not necessarily a limiting feature. The derivation and calculation for this exitant angles is also described in greater detail below in the aforementioned U.S. application Ser. No. 14/092,492.

Camera 1024 may be a broadband capture camera which exhibits broad spectral sensitivity across the visible and near-visible ranges of wavelengths, together with a liquid crystal tunable filter (LCTF) positioned in front of the camera so as to provide for multi-spectral image capture with 32 spectral bands ranging from 410 nm to 720 nm with an interval of 10 nm. More preferably, however, and as mentioned above, camera 1024 preferably captures images in only a subset of spectral bands (such as 5 spectral bands). Accordingly, in other embodiments contemplated herein, the camera may be a relatively inexpensive camera since it is not necessary to capture all 32 spectral bands. As an example, the camera 1024 may be implemented with a simple filter wheel in front of the camera, or in front of a light source which may be a broadband light source, with filters on the filter wheel corresponding in wavelength to the spectral bands selected for the subset As shown in FIG. 10, this example embodiment includes three (3) light sources and one (1) camera. One way to determine the number of light sources, and one way to determine the incident angles of the light sources, is discussed in greater detail above. Likewise, the number of cameras, together with their exitant angles, is discussed in greater detail in connection with the same application. In general, however, in order to facilitate rapid classification of materials, such as real-time classification of materials, the number of light sources, and the number of cameras is relatively small, such that materials can be classified with only a single multiplexed illumination. Preferably, the number of light sources should range between two and five, inclusive, most preferably two or three light sources, and the number of cameras should range between one and two, inclusive, most preferably one camera.

Although in this embodiment the spectral content of each individual light source is broadband and is identical to all others, it should be understood that the spectral content of the light sources might differ from each other. Likewise, in embodiments where there are plural cameras, although the spectral sensitivities of the cameras might match, it is also possible for the spectral sensitivities to differ.

Under control of classification and sorting controller 900, an object at inspection station 1020 is subjected to multiplexed illumination wherein all of plural broadband light sources 1021, 1022 and 1023 are illuminated simultaneously. Under such multiplexed illumination, camera 1024 captures a multi-spectral stack of plural images of light reflected from the object at the exitant angle, one image at each of multiple narrow spectral bands. The captured images are collected by classification and sorting controller 100, and are analyzed thereby, such as by deriving one slice of the so-called bidirectional reflectance distribution function (BRDF). The BRDF is a four-dimensional function that depends on incident and exitant angles, and defines how light is reflected from the surface of an object. With a camera positioned at a fixed exitant angle, only a "slice" of the BRDF is obtained.

Based on the BRDF slices, and other analysis which includes application of a feature vector algorithm to extract feature vectors for each image, and feeding of such feature vectors to a trained classification engine, classification and sorting controller 900 obtains a classification of the material from which the illuminated object is fabricated.

Figure 11:
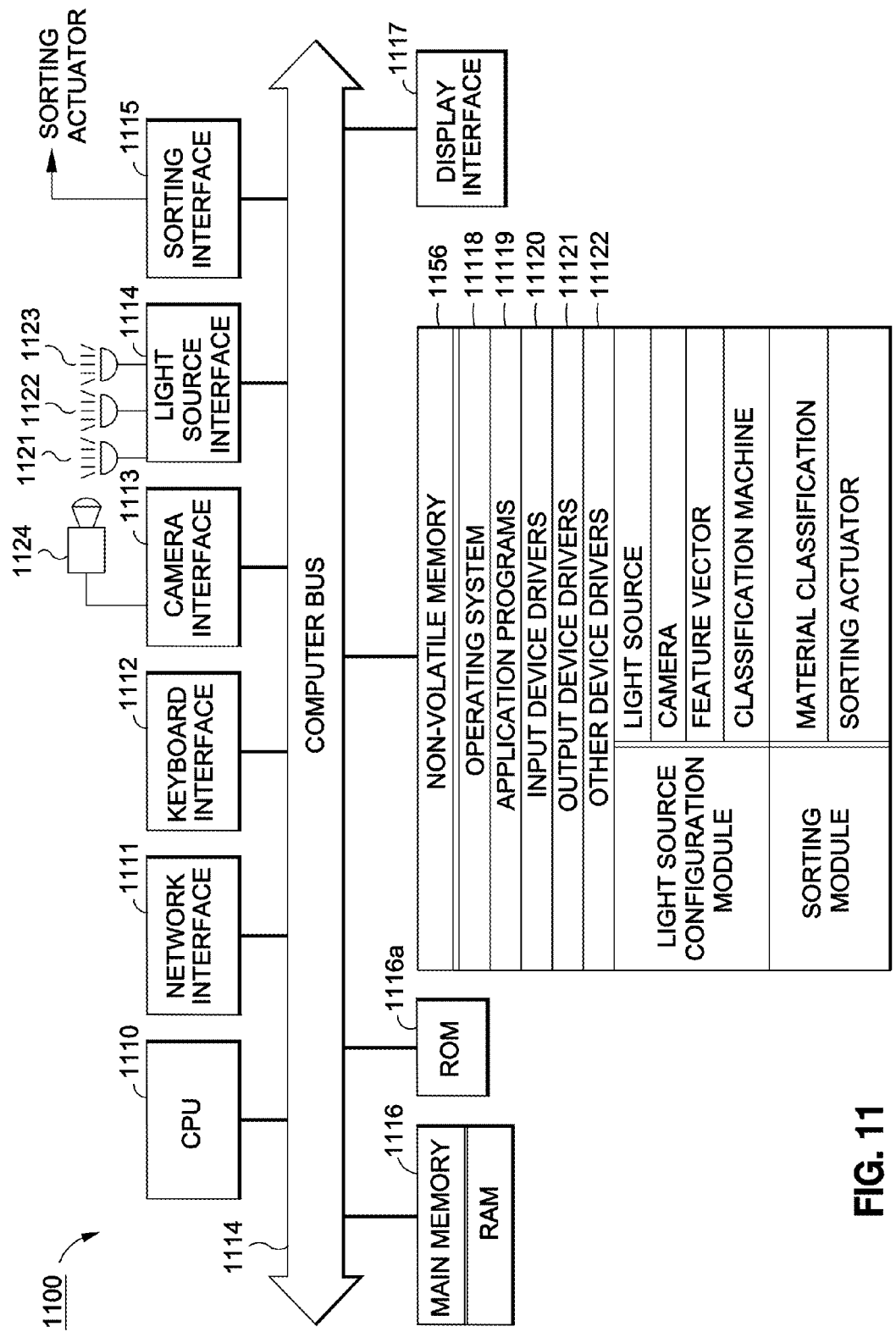
FIG. 11 is a view for explaining the architecture of a classification and sorting controller.

FIG. 11 is a view for explaining the architecture of classification and sorting controller 1100.

As shown in FIG. 11, classification and sorting controller 1100 includes central processing unit (CPU) 1110 which interfaces with computer bus 1114. Also interfacing with computer bus 1114 are non-volatile memory 1156 (e.g., a hard disk or other nonvolatile storage medium), network interface 1111, keyboard interface 1112, camera interface 1113, random access memory (RAM) 1116 for use as a main run-time transient memory, read only memory (ROM) 1116a, and display interface 1117 for a display screen or other output.

RAM 1116 interfaces with computer bus 1114 so as to provide information stored in RAM 1116 to CPU 1110 during execution of the instructions in software programs, such as an operating system, application programs, image processing modules, and device drivers. More specifically, CPU 1110 first loads computer-executable process steps from non-volatile memory 1156, or another non-transitory storage device into a region of RAM 1116. CPU 1110 can then execute the stored process steps from RAM 1116 in order to execute the loaded computer-executable process steps. Data also can be stored in RAM 1116 so that the data can be accessed by CPU 1110 during the execution of the computer-executable software programs, to the extent that such software programs have a need to access and/or modify the data.

As also shown in FIG. 11, non-volatile memory 1156 is an example of non-transitory computer-readable storage medium on which is stored computer-executable process steps for operating system 1118, and application programs 1119, such as graphic image management programs. Non-volatile memory 1156 also stores computer-executable process steps for device drivers for software interface to devices, such as input device drivers 1120, output device drivers 1121, and other device drivers 1122.

Non-volatile memory 1156 also stores a material classification module and a sorting module. The material classification module and the sorting module comprise computer-executable process steps for material classification of an object fabricated from an unknown material, and for sorting the object based on the material classification.

The computer-executable process steps for these modules may be configured as part of operating system 1118, as part of an output device driver in output device drivers 1121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The material classification module includes a corresponding plurality of modules for control of the light sources, for control of the camera(s) and for gathering of image data of such camera(s) a module for derivation of feature vectors according to a feature vector algorithm, such as feature vectors based on BRDF slices, and a classification machine. The classification machine accepts as inputs the feature vectors derived by the feature vector module, and provides a classification of the material from which the object under inspection is fabricated.

The sorting module for its part includes a corresponding plurality of modules related to input of material classification from the classification machine, and actuation of the sorting mechanism based on the classification.

Figure 12:
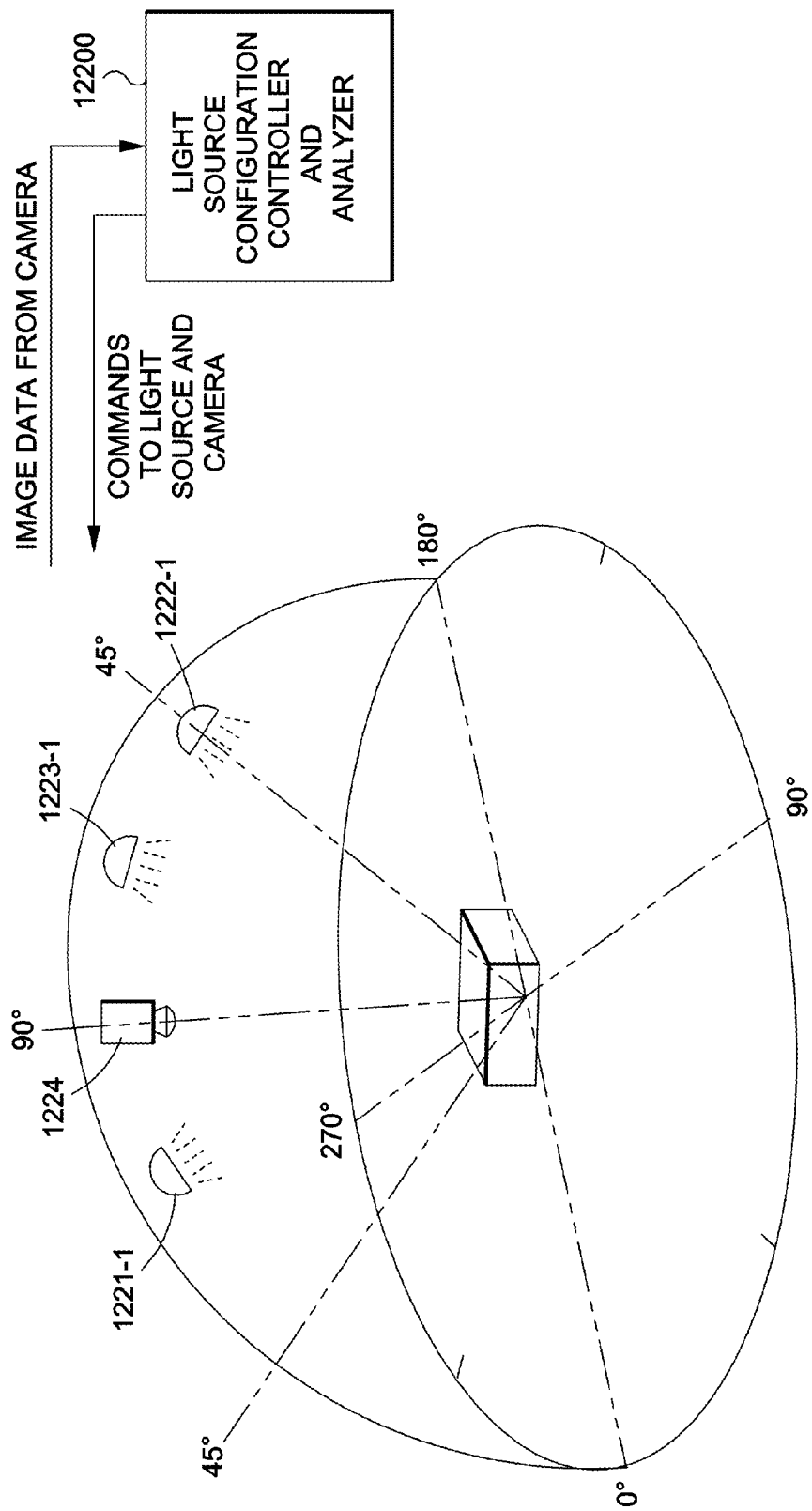
Figure 13:
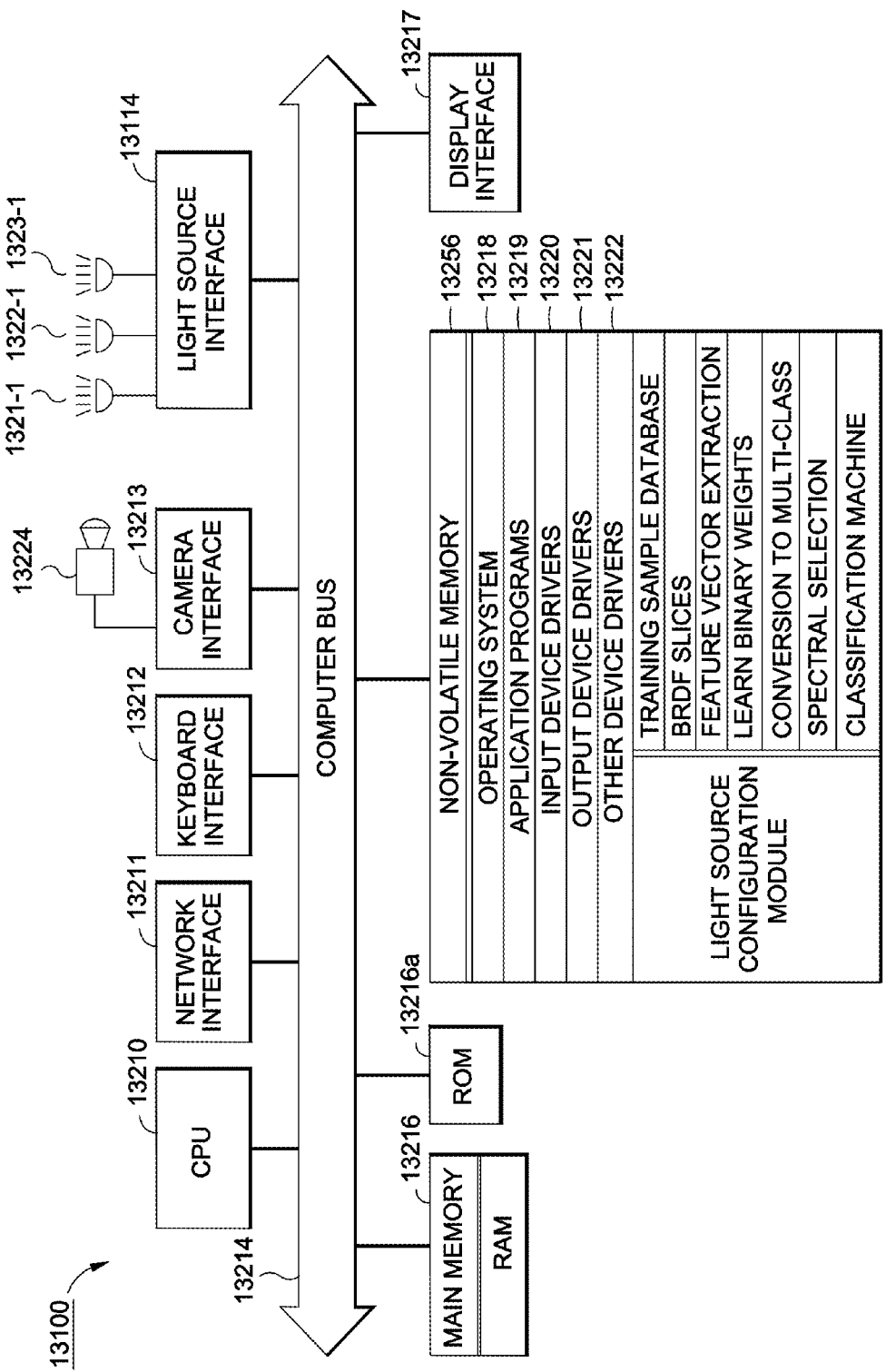

FIGS. 12 and 13 describe a further embodiment according to the description herein. These figures are used to describe the determination and calculation of the spectral wavebands captured by the classification system depicted in FIG. 9.

In particular, FIGS. 12 and 13 describe an embodiment in which a training sample of objects fabricated from known materials is subjected to illumination from plural light sources 1221-1, 1222-1 and 1223-1 of the same number and positioning as the light sources 921, 922 and 923 shown in FIG. 9. One purpose of the arrangement described in FIGS. 12 and 13 is to generate labeled training data over a wide variety of spectral wavebands, and thereafter to use the labeled training data to determine a relatively small subset of spectral wavebands that can be used in the arrangement of FIG. 9 yet still yield effective discrimination and classification of materials.

In one example embodiment, each of light sources 1221-1, 1222-1 and 1223-1 has a broadband spectral content, and each is positioned in azimuth and elevation so as to illuminate the labeled sample from directions that are unlabeled in FIG. 12, for purposes of clarity of illustration.

It should be recognized that more light sources than the three shown in FIGS. 12 and 13 can be used to generate the labeled training data. The training data can be used to determine the position and incidence angles of a subset of light sources having a large discriminative effect on material classification; such a subset thereafter is determinative of the position and incidence angles of the light sources 921, 922 and 923 shown in the industrial inspection system of FIG. 9. For example, twenty-five (25) light sources may be arranged in a hemispherical dome as proposed by Gu in [2]. Labeled training data is generated, and a subset of only a few such light sources is selected, such as three light sources (preferably two to five), together with the training data associated with the light sources in the subset. This process of selecting a small subset of light sources is described above.

The labeled training data is used to determine spectral wavebands captured from the multiplexed illumination of the light sources 921, 922 and 923 shown in the industrial inspection system of FIG. 9, with the selected spectral wavebands having a significant aptitude for distinguishing between and classifying materials. A classification machine is trained using the feature vectors corresponding to the spectral wavebands, using the labels from the labeled training sample.

FIG. 12 illustrates an embodiment in which a training sample of objects fabricated from known materials is subjected to illumination from light sources 1221-1, 1222-1 and 1223-1 each with a large broadband spectral content.

In one example embodiment depicted in FIG. 12, there are three light sources, but as explained previously other embodiments might have more, such as twenty-five (25) light sources arranged uniformly over a hemispherical dome surrounding a labeled object in the training sample. One camera 1224 is positioned at a predetermined exitant angle such as 90 degrees elevation. Each of the light sources 1221-1, 1222-1 and 1223-1 has a broadband spectral content so as to provide multiplexed illumination of the labeled object in the training sample. In multiplexed illumination, multiple light sources illuminate the object simultaneously from different directions. Camera 1224 captures a multi-spectral stack of plural images of light reflected from the object at the exitant angle, one image at each of 32 multiple narrow spectral bands.

Camera 1224 is a multi-spectral capture camera, capable of capturing images in each of plural spectral bands which are narrow, such as in each of 32 spectral bands ranging from 410 nm to 720 nm with an interval of 10 nm. For example, camera 1224 may be a broad-band capture camera with a tunable filter positioned before it, such as a liquid crystal tunable filter (LCTF) with 32 spectral bands ranging from 410 nm to 720 nm with an interval of 10 nm.

In this embodiment, camera 1224 is a broadband capture camera which exhibits broad spectral sensitivity across the visible and near-visible ranges of wavelengths, together with a liquid crystal tunable filter (LCTF) positioned in front of the camera so as to provide for multi-spectral image capture with 32 spectral bands ranging from 410 nm to 720 nm with an interval of 10 nm.

In one preferable arrangement, the spectral content of the light sources in the FIG. 12 embodiment is identical to the spectral content of a corresponding light source in the FIG. 9 classification system. Likewise, the spectral sensitivity of the camera is identical to that of the camera shown in the FIG. 9 classification system. It should be understood, however, that the spectral content of the light sources, and the spectral sensitivity of the camera, might in some embodiments be different.

Operation of the FIG. 12 embodiment proceeds under control of the light source configuration controller and analyzer 200.

FIG. 13 illustrates more details concerning the internal architecture of light source configuration controller and analyzer 12200.

As shown in FIG. 13, light source configuration controller and analyzer 12200 includes central processing unit (CPU) 13210 which interfaces with computer bus 13214. Also interfacing with computer bus 13214 are non-volatile memory 13256 (e.g., a hard disk or other nonvolatile storage medium), network interface 13211, keyboard interface 13212, camera interface 13213, random access memory (RAM) 13216 for use as a main run-time transient memory, read only memory (ROM) 13216*a*, and display interface 13217 for a display screen or other output.

RAM 13216 interfaces with computer bus 13214 so as to provide information stored in RAM 13216 to CPU 13210 during execution of the instructions in software programs, such as an operating system, application programs, image processing modules, and device drivers. More specifically, CPU 13210 first loads computer-executable process steps from non-volatile memory 13256, or another non-transitory storage device into a region of RAM 13216. CPU 13210 can then execute the stored process steps from RAM 13216 in order to execute the loaded computer-executable process steps. Data also can be stored in RAM 13216 so that the data can be accessed by CPU 13210 during the execution of the computer-executable software programs, to the extent that such software programs have a need to access and/or modify the data.

As also shown in FIG. 13, non-volatile memory 13256 is an example of non-transitory computer-readable storage medium on which is stored computer-executable process steps for operating system 13218, and application programs 13219, such as graphic image management programs. Non-volatile memory 13256 also stores computer-executable process steps for device drivers for software interface to devices, such as input device drivers 13220, output device drivers 13221, and other device drivers 13222.

Non-volatile memory 13256 also stores a light source configuration module. The light source configuration module comprises computer-executable process steps for determining, from labeled training data which includes a superset of all spectral content of all light sources, a satisfactory subset of spectral content for light sources by which material classification of an object fabricated from an unknown material may be made accurately and without any significant loss in accuracy as compared to material classification made by the superset.

The computer-executable process steps for these modules may be configured as part of operating system 13218, as part of an output device driver in output device drivers 13221, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The light source configuration module includes a corresponding plurality of modules including a module for storing a database of the labeled training sample. The database of labeled training material samples is defined within a multi-class classification framework and is captured using a relatively large number of spectral bands.

The light source configuration module further includes a module for computing feature vector representations of these materials, such as in accordance with application of an algorithm for extraction of feature vectors; a module for learning a set of weights representing the importance of the spectral bands, using Adaboost for example, on the features in each binary classification task; a module for converting the weights from the binary classification tasks to a set of weights for the multi-class classification framework using an appropriate mapping function; and a module for selecting the optimal spectral bands of highest weight as more optimal than other spectral bands for purposes of material classification.

In addition, the light source configuration module further includes a module for storing and training a classification machine. Given the optimal spectral bands as selected above, and given the corresponding images obtained using them, the feature vector representations of the material samples may be computed using these images. Then a classification engine is trained, such as SVM, on the set of features of the training samples. The trained classification engine along with an imaging setup including the optimal spectral bands may then be used in a factory setting such as the industrial inspection system of FIG. 1 to obtain images of and classify new material samples as observed.

<Framework>

Referring again to the architectures described in FIGS. 9 through 13 above, an implementation will now be described.

As described herein, selecting spectral bands for material classification involves image capture and estimation of multiplexed images, applying machine learning techniques such as Adaboost to estimate the weight of each spectral band in a binary classification framework, selecting the spectral bands which provide most discrimination among a set of materials in multi-class classification, and material classification.

With regard to selecting spectral bands or filters for material classification under multiplexed illumination, one motivation is to use 32 narrow spectral bands as compared with 6 broadband ones in the arrangement of Gu at [2] for imaging materials for the purpose of classifying them. In the arrangement of Gu at [2], each light source was composed of a cluster of six differently-colored LEDs, with colors blue, green, yellow red, orange and white, with the white LED positioned at the center of the cluster. In this embodiment, for selecting spectral bands or filters for material classification under multiplexed illumination, five (5) spectral bands are selected from 32 filters which would provide the most discrimination among the materials to be classified.

Figure 14:
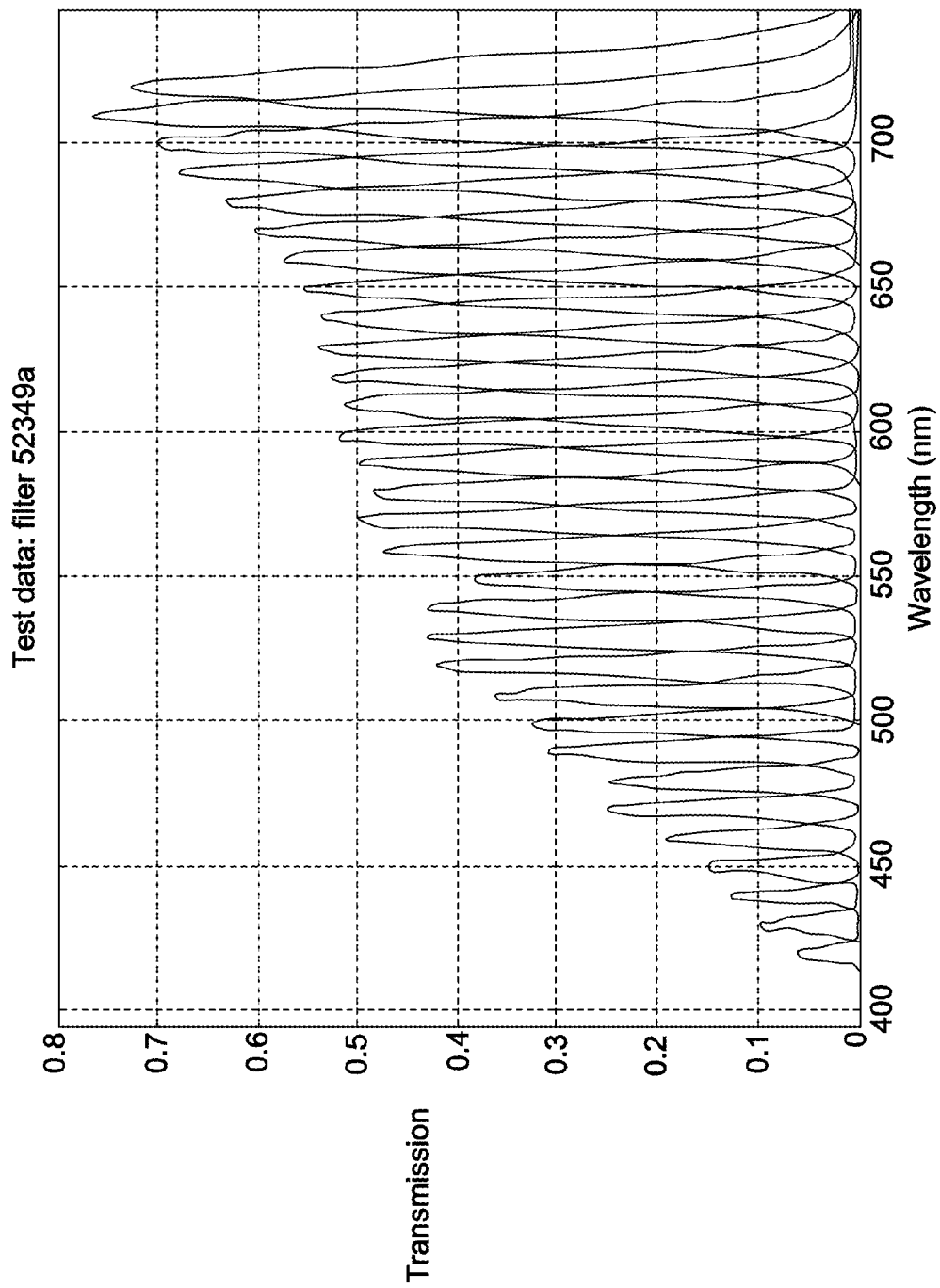
FIG. 14 illustrates transmittance spectra for 32 bands in a LCTF (liquid crystal tunable filter).
Figure 15:
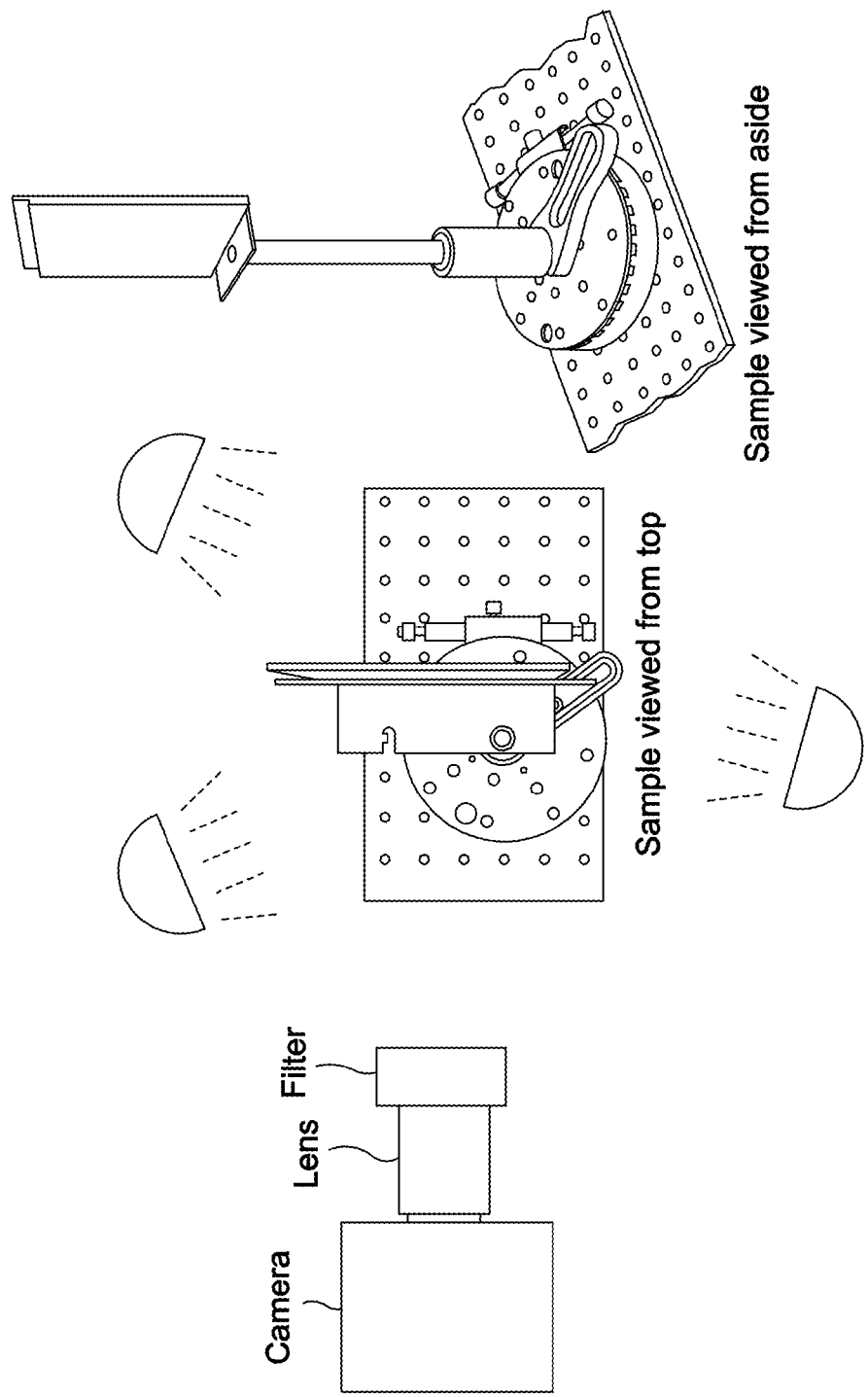
FIG. 15 schematically depicts an image capture configuration.

As for spectral transmittances of the 32 spectral bands in a typical Liquid Crystal Tunable Filter (LCTF), these transmittances are depicted in FIG. 14. In particular, FIG. 14 shows the transmittance spectra for 32 bands in the LCTF FIG. 15 schematically depicts an image capture configuration of this embodiment, in which there are three broadband lights sources that illuminate the sample with broad spectral light, and in which a camera with an LCTF filter positioned in the light path thereof captures multiple different images of the object, each image under a different narrow-band spectral filter as provided by the LCTF filter.

Figure 16:
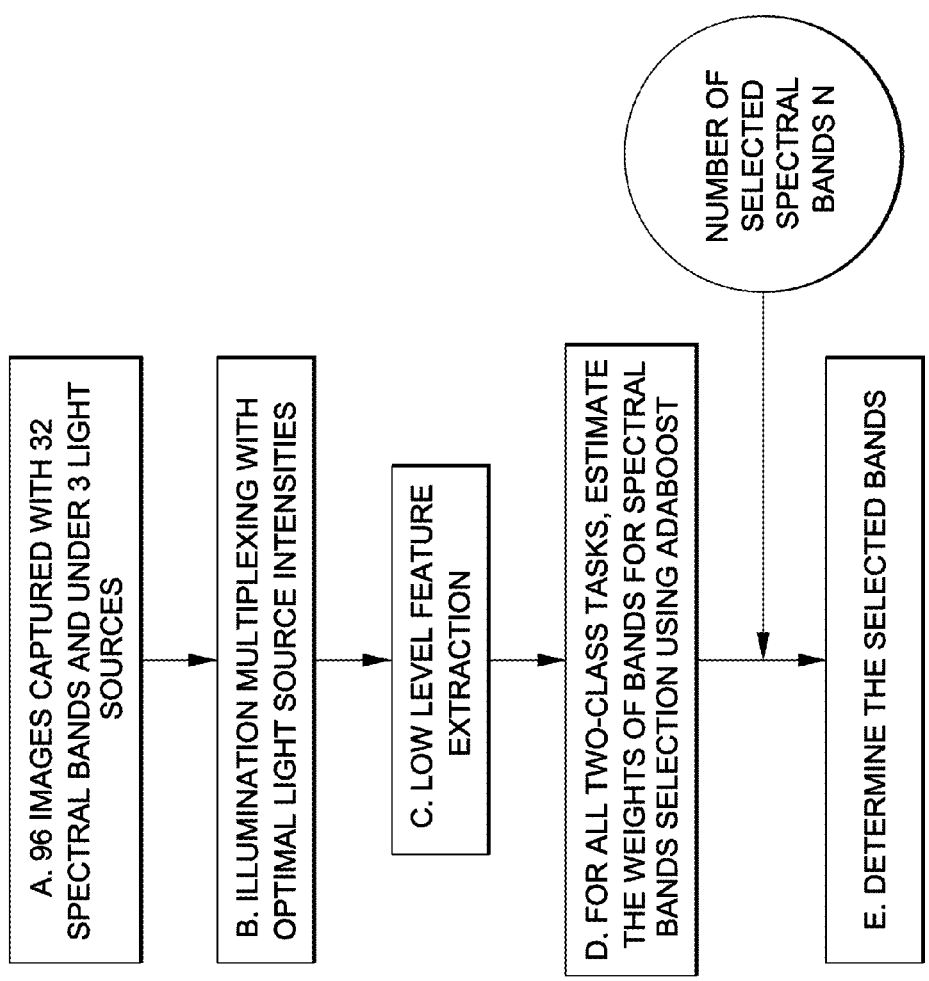
FIG. 16 illustrates a framework for spectral bands selection for material classification under multiplexed illumination.

FIG. 16 shows a framework for the approach described herein. The framework of FIG. 16 includes steps A through E. These steps A through E are described below in Part 1, below, "Steps of the Framework for Selection of Spectral Bands or Filters". In addition, there is a Part 2, also described below, "Training and Classification Using Images Corresponding to the Selected Bands or Filters". Part 2 describes the effect of choosing the optimal subset of filters, such as the compromise on material classification when using images corresponding to a smaller set of filters. Part 2 includes a verification that even the raw measurements or pixel intensities from images corresponding to the optimal spectral bands provide competitive accuracy in material classification.

<Part 1: Steps of the Framework for Selection of Spectral Bands or Filters>

Referring to FIG. 16, the lettered steps A through E therein are explained below.

Step A: Database of Captured Images.

The database of images captured by the FIG. 7 configuration will now be described.

In the database, there were twenty-seven (27) different classes of materials, as follows: Wood (2 different classes), Stainless Steel, ABS plastic-gray, Ceramic, Titanium, HIPS plastic-white, Fabric, Tin, Nitrile rubber-black, Gray Silicone, Aluminum (5 different classes), Copper, Zinc (2 different classes), ABS plastic-white, Brass, Mild Steel, HIPS plastic-white (2 different classes), Steel, Nickel, Lead.

Figure 19:
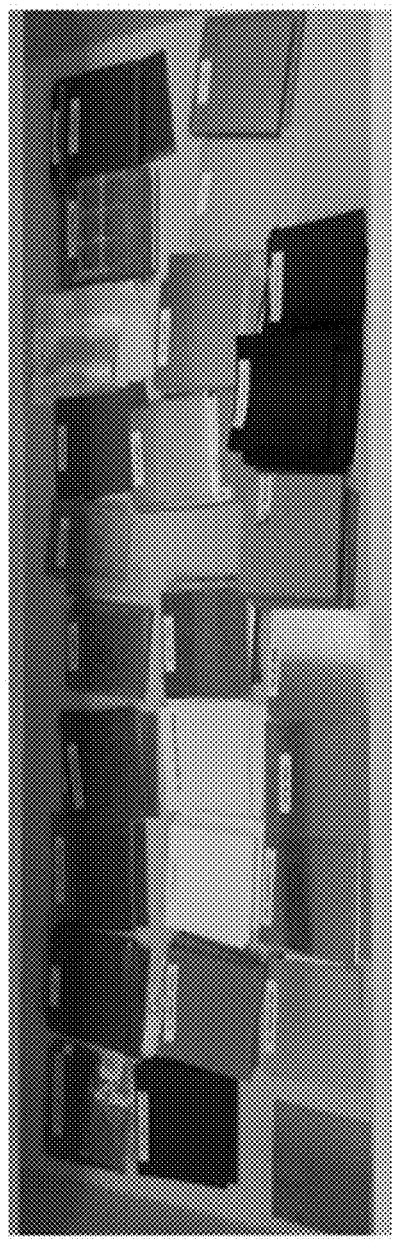
FIG. 19 shows a photograph of twenty-seven (27) classes of material samples used to build a labeled database of training images.

FIG. 19 shows a photograph of the 27 classes of materials used to build the database of one example embodiment As seen in FIG. 19, there are 27 classes, and each class of materials contains 4 samples. Each sample is imaged using 32 spectral narrow bands under 3 directions of incident illumination. As a result, each sample is imaged 96 times with different configurations of spectral bands and illumination directions.

Step B: Illumination Multiplexing.

Given the sets of 3 images captured under different illumination directions in 32 spectral bands, 32 sets of light source intensities for multiplexing are computed so that the multiplexed image for each spectral band is most discriminative. Illumination multiplexing typically consists of capturing the image of the sample under multiple light sources which are illuminated simultaneously to thereby reduce the number of images that need to be captured. However, if there are equipment restrictions, the image may be captured under multiple light sources.

As mentioned, each sample is captured under incident illumination in 3 directions to obtain images $I_1$, $I_2$, and $I_3$. Given the linearity of the image formation process, the multiplexed image is then estimated as a linear combination of images captured when the sample is illuminated by each of the light sources:

$$I = w_1 I_1 + w_2 I_2 + w_3 I_3 \qquad \text{(Equation 1-1)}$$

where the weights w1, w2 and w3 form a vector of weights $\vec{w}$ of light intensities.

One advantage of using illumination multiplexing is increasing the Signal-to-Noise-Ratio (SNR) of the image. This embodiment uses the SVM (Support Vector Machine) with a linear kernel to estimate the light source intensities $\vec{w}$, which are used for estimating the multiplexed image. Other algorithms for discriminative analysis, such as LDA (Linear Discriminant Analysis), can also be used to compute the intensities, although it is preferable that such algorithms are linear.

Table C, below, shows a numerical example of the multiplexed illumination of Step B in the FIG. 16 framework. In the example of Table C, there are three light sources and 32 spectral bands. Each light source is turned on independently, and an image is captured for each one of 32 spectral bands, at full intensity each spectral band. This yields a total of 3×32 image captures, each one at full intensity for one spectral band and at zero intensity for the remaining 31 spectral bands. In this example, intensity is controllable with an 8-bit command, such that intensity is represented as a number between 0 and 255 inclusive. Linearized weighting is applied so that the multiplexed image for each spectral band is most discriminative, thereby to form a vector of weights $\vec{w}$ of light intensities. Table C gives numerical examples of the resulting vector of weights $\vec{w}$ of light intensities w1, w2 and w3. As seen in Table C, each of the weights falls between 0 and 255 inclusive.

TABLE C

| | band 1 (λ1) | band 2 (λ2) | band 3 (λ3) | band 4 (λ4) | band 5 (λ5) | ... | band 32 (λ32) |
|---|---|---|---|---|---|---|---|
| Weight w1 for Source 1 | 10 | 50 | 30 | 150 | 50 | ... | 100 |
| Weight w2 for Source 2 | 100 | 22 | 12 | 22 | 112 | ... | 94 |
| Weight w3 for Source 3 | 35 | 125 | 50 | 12 | 125 | ... | 40 |

Table C: An example of light source intensities for illumination multiplexing in different spectral bands.

Samples of objects for classification are thereafter illuminated by multiplexed illumination in which all three light sources are turned on simultaneously, and with intensity of each of the 32 spectral bands controlled in accordance with weight vector $\vec{w}$ of light intensities w1, w2 and w3.

Step C: Low-Level Feature Extraction.

Given the multiplexed spectral images, the low-level features are extracted. In this embodiment, the low level features are the concatenations of the pixel values in the images corresponding to the 32 spectral bands. More specifically, each point on the material is considered as a sample point so the low level feature for one point is a 32×1 column vector. Statistics other than the raw pixel values could be used for the features as well, such as the means of pixel values clusters which can be estimated with the K-Means algorithm.

Step D: Weight Estimation.

With the labeled samples and low-level features of samples under multiplexed illumination, the weight indicating the discriminative ability of each spectral band is estimated. Estimation may be made using a classification engine such as a classification engine built by application of the Adaboost algorithm. The Adaboost algorithm takes in the feature in each spectral band as the input for each weak learner, which is a classifier that performs slightly better than random. Then the final inference result is the ensemble of the inferences of all the weak learners. One advantage of using Adaboost for combining the ensemble of weak learners is that it estimates the weights of the weak learners. Because each weak learner corresponds to a specific spectral band, the estimated weights indicate the discriminative abilities of the spectral bands. The spectral band selection is based on those discriminative abilities (i.e. weights). This step is performed for all of the two-class material classification tasks.

Figure 17:
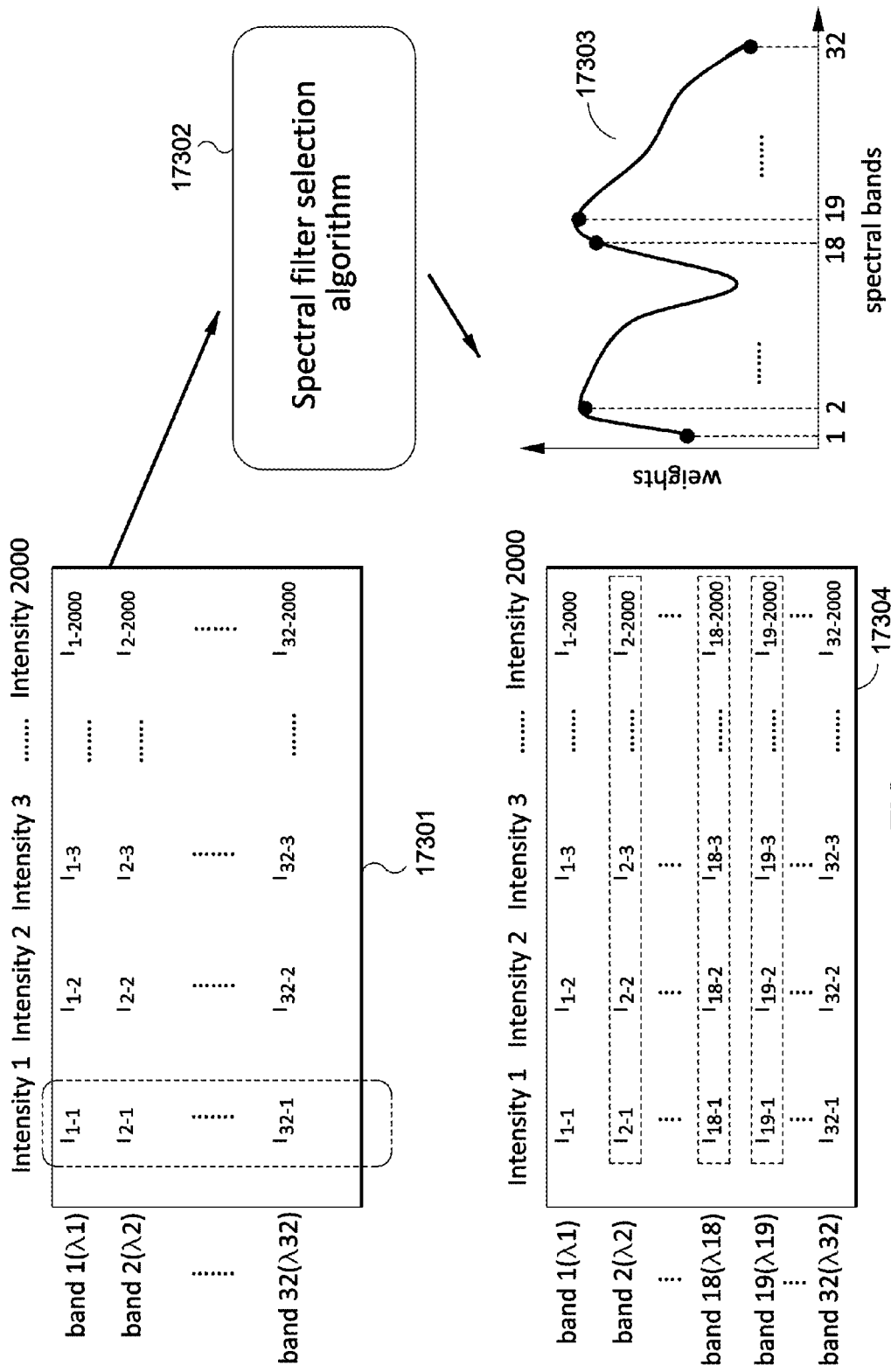
FIG. 17 illustrates selection of weights and spectral bands using the framework of FIG. 16.

FIG. 17 diagrammatically illustrates selection of weights according to Steps C and D of the framework depicted in FIG. 16. FIG. 17 also illustrates selection of spectral bands according to Step E of the framework, and this aspect of FIG. 17 is discussed later. In FIG. 17, reference number 17301 refers to the low-level features extracted at Step C. Reference number 17302 refers to the weight estimation of Step D, wherein 17303 refers to weight determinations for each of the spectral bands, showing spectral bands with the largest weights, and wherein 17304 is a repetition of 17301 but with highlighting for the spectral bands with the largest weights.

More specifically, reference number 17301 is an example of extracted low-level features in the form of acquired intensity values. Intensity 1, highlighted with a dashed line, is a 32×1 column vector including intensity values of each of 32 spectral bands λ1 through λ32 acquired from a first point in a captured image. For example, when the captured image is a rectangle of 40 pixels times 50 pixels, 2000 such column vectors are acquired. All of the column vectors are used as the input of the spectral filter selection algorithm, which is Adaboost in this example embodiment.

Based on the inputted features, the filter selection algorithm depicted at 17302 provides two outputs: weight determinations as depicted at 17303, and selected spectral bands having the largest weights as depicted at 17304. In more detail, filter selection at 17302 estimates the weights of all the spectral bands, and provides a determination of weights at each spectral band, as depicted at 17303. For purposes of illustration, FIG. 9 shows only five (5) representative weights, at spectral bands corresponding to wavelengths λ1, λ2, λ18, λ19 and λ32. It should be understood, however, that filter selection at 17302 estimates weights at all 32 spectral bands.

Reverting to the example embodiment described herein, and with respect to all of the two-class material classification tasks, the classification problem addressed by these experiments may be formulated as follows: Consider a five-class material classification problem: Nickel, Titanium, Tin, Aluminum and Copper. The formulation of the classification problem may therefore be broken down into 10 binary classification problems/tasks, as follows: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

Spectral band selection for the classification problem as so formulated leads to the following Table D, which shows the indexes of the first 5 filters with the largest weights for each of the above ten (10) sets of binary classification tasks within the five-class material classification framework. The last column shows the indexes of the filters selected for the five-class classification framework.

TABLE D

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | All |
| Index of selected bands | 16 | 19 | 5 | 3 | 30 | 16 | 16 | 16 | 16 | 5 | 16 |
| | 19 | 16 | 30 | 6 | 31 | 19 | 17 | 19 | 19 | 3 | 19 |
| | 17 | 18 | 10 | 5 | 14 | 11 | 18 | 9 | 14 | 4 | 5 |
| | 28 | 32 | 4 | 32 | 4 | 9 | 32 | 5 | 4 | 30 | 30 |
| | 29 | 21 | 31 | 4 | 18 | 18 | 21 | 3 | 18 | 31 | 3 |

Table D: Indexes of the first 5 filters with the largest weights for each of ten (10) sets of binary classification tasks within the five-class material classification framework. The materials are Nickel, Titanium, Tin, Aluminum and Copper. In each column, the indexes of filters are arranged in descending order of their weights. The last column shows the set of selected filters after combing the weights. The 10 binary classification tasks correspond to the 10 possible combinations of two materials selected from the five materials of Nickel, Titanium, Tin, Aluminum and Copper. The corresponding task numbers are: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper For each task, there was an estimation of the discriminative ability of each spectral band. The pixels of the material images are taken to be the samples. The low-level features are 32-dimensional. The Adaboost algorithm was used to estimate a weighting coefficient α corresponding to each spectral band by minimizing an exponential loss. Each weak learner corresponds to one spectral band.

The application of the Adaboost algorithm to spectral band selection will now be explained. The given is the training set $(x_1,y_1), \ldots, (x_m,y_m)$ where $x_i$ and $y_i$ are the training data and labels respectively. From this given, the applied Adaboost algorithm is as follows:

$$\text{For } i = 1, \ldots, m: D_1(i) = 1/m \quad \text{(Equation 2-1)}$$

$$\text{For } t = 1, \ldots, T: h_t = \underset{h_t \in H}{\operatorname{argmax}} |0.5 - \varepsilon_t|,$$

where:

$$\varepsilon_t = \sum_{i=1}^{m} D_t(i) I(y_i \neq h_t(x_i)) \quad \text{(Equation 2-2)}$$

and I is the indicator function.

$$\alpha_t = \frac{1}{2} \ln \frac{1-\varepsilon_t}{\varepsilon_t} \quad \text{(Equation 2-3)}$$

$$\text{Update: } D_{t+1}(i) = \frac{D_t(i) \exp(\alpha_t(2I(y_i \neq h_t(x_i)) - 1))}{Z_t} \quad \text{(Eq. 2-4)}$$

where $Z_t$ is a normalization factor.

Step E: Determination of Selected Bands.

For a two-class classification task, the selected spectral bands would be the first N bands with the largest weights computed in Step D, where N is a number set by the user. However, for a multi-class task, different sets of filters corresponding to different binary classification tasks would be selected, as the multi-class classification engine is typically broken down into a set of binary classification algorithms. The ensemble of the sets will eventually constitute more than N filters if sets of selected filters are not exactly the same.

In order to combine the N selected filters from the individual binary classification tasks, the weights calculated in Step D are combined to obtain a new set of weights W. Thus, in this example, the selected spectral bands from each task shown in Table B were combined. In combining the spectral bands, the weights corresponding to each spectral band and each binary task are combined to obtain a set of weights $W=\{W_\lambda, \lambda \in \{1, \ldots, 32\}\}$, where $W_\lambda$ is the combined weight for one spectral band. The combined weight is estimated as:

$$W_\lambda = \frac{1}{Z} \sum_i \exp\left(-\left(\frac{1-\tilde{\alpha}_{i,\lambda}}{\tilde{\alpha}_{i,\lambda}}\right)^p\right), \quad \text{(Equation 3-1)}$$

where $\tilde{\alpha}_{i,\lambda}$ is the normalized weight of spectral band λ corresponding to the binary classification task i, Z is a normalization term which ensures that the sum of $W_\lambda$ over all spectral bands is one. The selected spectral bands are taken to be the first N bands with the largest $W_\lambda$'s. The shape of the mapping function in Equation (3-1) is determined by the parameter p. The mapping function maps the weights of spectral bands as estimated in the two-class classification tasks to the weights W. In this embodiment, p=0.5.

The technique described above is used to find the five (5) selected filters within a five-class classification framework. Table D, above, is repeated here for convenience. Table D shows the indexes of the first 5 filters with the largest weights for each pair of classes considered for the binary classification tasks within the five-class material classification framework. The last column shows the indexes of the filters selected for the five-class classification framework. These indexes are computed using the mapping function as described in Equation (3-1) of Step E above.

TABLE D (repeated from above)

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | All |
| Index of selected bands | 16 | 19 | 5 | 3 | 30 | 16 | 16 | 16 | 16 | 5 | 16 |
| | 19 | 16 | 30 | 6 | 31 | 19 | 17 | 19 | 19 | 3 | 19 |
| | 17 | 18 | 10 | 5 | 14 | 11 | 18 | 9 | 14 | 4 | 5 |
| | 28 | 32 | 4 | 32 | 4 | 9 | 32 | 5 | 4 | 30 | 30 |
| | 29 | 21 | 31 | 4 | 18 | 18 | 21 | 3 | 18 | 31 | 3 |

Table D: The selection of spectral bands according to this Step E is depicted diagrammatically in FIG. 17. Referring again to FIG. 17, and as previously described, the filter selection algorithm depicted at 17302 provides two outputs: weight determinations as depicted at 17303, and selected spectral bands having the largest weights as depicted at 17304. Selection of spectral bands proceeds according to this Step E of the framework. As described herein, there is a selection of N spectral bands having the largest weights of the 32 weights at 17303. In the numerical example of FIG. 17, it will be observed that the three spectral bands corresponding to wavelengths $\lambda 2$, $\lambda 18$ and $\lambda 19$ have the largest weights. As a result, these three spectral bands are included amongst the N=5 spectral bands selected in this embodiment. The selection of these spectral bands is highlighted by dashed lines which enclose these spectral bands at 17304 in FIG. 17. Since in this example N=5, two other unshown spectral bands are also selected, so as to make up the complement of N=5 selected spectral bands with the largest weights.

<Part 2: Training and Classification Using Images Corresponding to the Selected Bands or Filters>

Given the labeled training samples and the N bands selected as described in the previous section (i.e., in Part 1), the classifiers can be trained and tested using the captured images corresponding to only the N bands. One goal of these experiments is to show that using images corresponding to only a subset N of the 32 spectral bands provides competitive performance in material classification. In this embodiment, N=5, i.e., a subset of 5 out of 32 spectral bands is selected. Different classification engines can be used and this embodiment uses the SVM with a linear kernel. The advantage of using an SVM is that it takes as input the features of different bands in one feature vector and therefore the information among spectral bands is taken into consideration.

The classifier is trained on multiple folds of training data and tested on the remaining folds. The total number of samples is split into 50% of training data and 50% of testing data. For each material category, there are four pieces of the material. Note that in this Part 2, the term "pieces" is used as compared with "samples" to distinguish between the samples as used in the classification algorithm. Since a sample is considered to be a pixel in the classification algorithm, the number of samples corresponding to one material category would be 4×M, where M is the number of pixels in an image of one piece of material. Given that there are two categories in a binary classification task, there would be 8×M samples in total. The samples are split into 6 folds of training and testing data. As mentioned earlier, half of the samples are taken to be training ones and the other half as testing ones. Also, it is assumed that there are equal numbers of samples from both categories in the test set and that the indices of the testing (or training) samples from both classes are the same. The classification accuracy computed is then taken to be the average over the classification accuracies of the test sets of the 6 folds.

Figure 20:
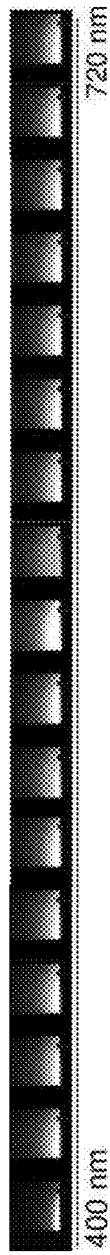
FIG. 20 shows seventeen (17) samples of 33 HDR (high dynamic range) images captured of Aluminum 2024 under one light source.

FIG. 20 illustrates 17 samples of the 33 HDR (high dynamic range) images captured of Aluminum 2024 under one light source.

In FIG. 20, the bands corresponding to the images shown have center wavelengths which were selected in the range of 400 nm to 720 nm with an increment of 20 nm.

Results obtained for these material classification experiments will now be presented.

Figure 21:
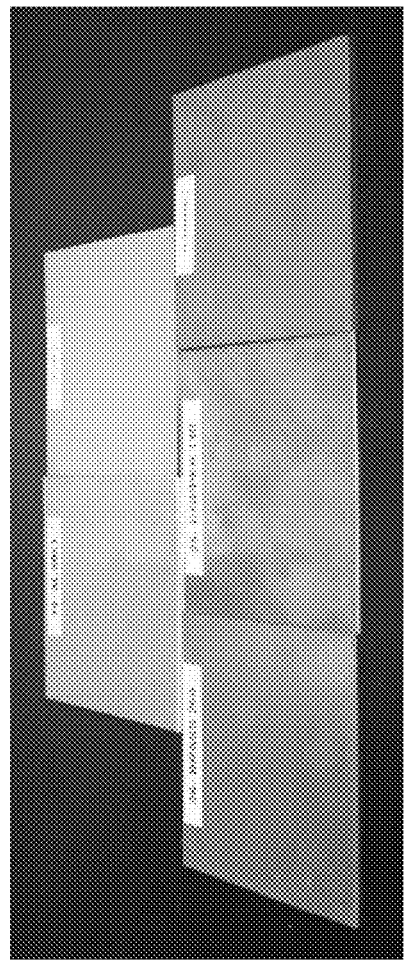
FIG. 21 shows a photograph of some of the samples of classified materials.

FIG. 21 shows a photograph of some of the samples of the materials classified in this experiment, namely, Aluminum, Tin, Brass, Copper, and Titanium.

To investigate the compromise on classification accuracy using images corresponding to a selected set of spectral bands as compared with all 32, five (5) material categories are taken from the database and classified using the images corresponding to the different numbers of filters. Results for classifying two different sets of five-(5) material categories are shown in Table E and Table F, respectively. The material categories for which results are shown in Table D are Nickel, Titanium, Tin, Aluminum, and Copper. The material categories for which results are shown in Table F are Zinc, Steel, Lead, Aluminum, and Brass. The tables show classification accuracies for each of the binary classification tasks within the five-class classification framework when images corresponding to 5 filters and 32 filters are used.

Table E thus shows classification accuracy for each binary classification task, for all ten (10) of the binary class pairs of the following five (5) materials: Nickel, Titanium, Tin, Aluminum, and Copper. In Table C, the top row shows classification accuracies using 5 selected spectral bands, whereas the bottom row shows classification accuracies using all 32 spectral bands. The indexes of the tasks are the same as the tasks in Table D, namely: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

TABLE E

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | All |
| 5 bands | 99.99 | 99.99 | 70.62 | 98.83 | 97.10 | 99.98 | 99.99 | 99.98 | 99.99 | 99.75 | 96.63 |
| All bands | 99.99 | 100.0 | 77.35 | 99.62 | 94.82 | 100.0 | 100.0 | 100.0 | 100.0 | 99.88 | 97.17 |

Table E: Classification accuracy for each binary classification task, comparing use of 5 selected spectral bands (top row) against use of all 32 spectral bands (bottom row) for a first set of five materials. The indexes of the tasks are: Task 1: Nickel vs. Titanium; Task 2: Nickel vs. Tin; Task 3: Nickel vs. Aluminum; Task 4: Nickel vs. Copper; Task 5 : Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

Likewise, Table F shows classification accuracy for each binary classification task, for all ten (10) of the binary class pairs of a different set of five (5) materials as compared against the five materials in Table E. In Table F, the materials are: Zinc, Steel, Lead, Aluminum and Brass. In Table F, the top row shows classification accuracies using 5 selected spectral bands, whereas the bottom row shows classification accuracies using all 32 spectral bands. The indexes of the tasks are: Task 1: Zinc vs. Steel; Task 2: Zinc vs. Lead; Task 3: Zinc vs. Aluminum; Task 4: Zinc vs. Brass; Task 5: Steel vs. Lead; Task 6: Steel vs. Aluminum; Task 7: Steel vs. Brass; Task 8: Lead vs. Aluminum; Task 9: Lead vs. Brass; Task 10: Aluminum vs. Brass.

TABLE F

| | Task number within the multi-class classification framework | | | | | | | | | |
|---|---|---|---|---|---|---|---|---|---|---|
| | Task 1 | Task 2 | Task 3 | Task 4 | Task 5 | Task 6 | Task 7 | Task 8 | Task 9 | Task 10 | All |
| 5 bands | 62.76 | 74.81 | 93.22 | 99.78 | 84.22 | 76.19 | 91.15 | 95.29 | 97.39 | 94.24 | 86.91 |
| All bands | 60.08 | 82.63 | 93.02 | 85.85 | 78.73 | 70.92 | 83.19 | 96.29 | 88.99 | 99.88 | 82.75 |

Table F: Classification accuracy for each binary classification task, comparing use of 5 selected spectral bands (top row) against use of all 32 spectral bands (bottom row) for a second, different set of five materials. The indexes of the tasks are: Task 1: Zinc vs. Steel; Task 2: Zinc vs. Lead; Task 3: Zinc vs. Aluminum; Task 4: Zinc vs. Brass; Task 5: Steel vs. Lead; Task 6: Steel vs. Aluminum; Task 7: Steel vs. Brass; Task 8: Lead vs. Aluminum; Task 9: Lead vs. Brass; Task 10: Aluminum vs. Brass.

It can be seen that on average the 5-band results are comparable to the 32-band results, or that there is an improvement when using 5 bands. The improvement can be attributed to the fact that the most discriminative features corresponding to the selected bands are used in the classification engine in the 5-band case.

In order to more closely examine the impact of using different numbers of filters on the multi-class classification engine, different numbers of N selected filters were considered: 3, 5, 7, 11, 21, and 32. Table G and Table H list the classification accuracies for the multi-class classification framework when images corresponding to each of these numbers of filters are used. For Table G, the material categories used are Nickel, Titanium, Tin, Aluminum, and Copper (which are the same materials as those listed in Table C), and for Table H, the material categories used are Zinc, Steel, Lead, Aluminum and Brass (which are the same materials as those listed in Table F). As shown and as compatible with the results shown in Table E and Table F, increasing N does not necessarily lead to an increase in classification accuracy. Also, the compromise on classification accuracy is small even when images from a subset of filters or spectral bands from the 32 are used.

TABLE G

| 3 filters | 5 filters | 7 filters | 11 filters | 21 filters | 32 filters |
|---|---|---|---|---|---|
| 90.30 | 96.63 | 92.80 | 94.25 | 97.07 | 97.17 |

Description of Table G: The overall average classification accuracies for the multi-class classification engine when different numbers of filters are used. The materials are the same set of materials used for Table E, namely: Nickel, Titanium, Tin, Aluminum and Copper.

TABLE H

| 3 filters | 5 filters | 7 filters | 11 filters | 21 filters | 32 filters |
|---|---|---|---|---|---|
| 85.49 | 86.91 | 82.41 | 82.71 | 82.45 | 82.75 |

Description of Table H: The overall average classification accuracies for the multi-class classification engine when different numbers of filters are used. The materials are the same set of materials used for Table F, namely: Zinc, Steel, Lead, Aluminum and Brass.

Figure 18:
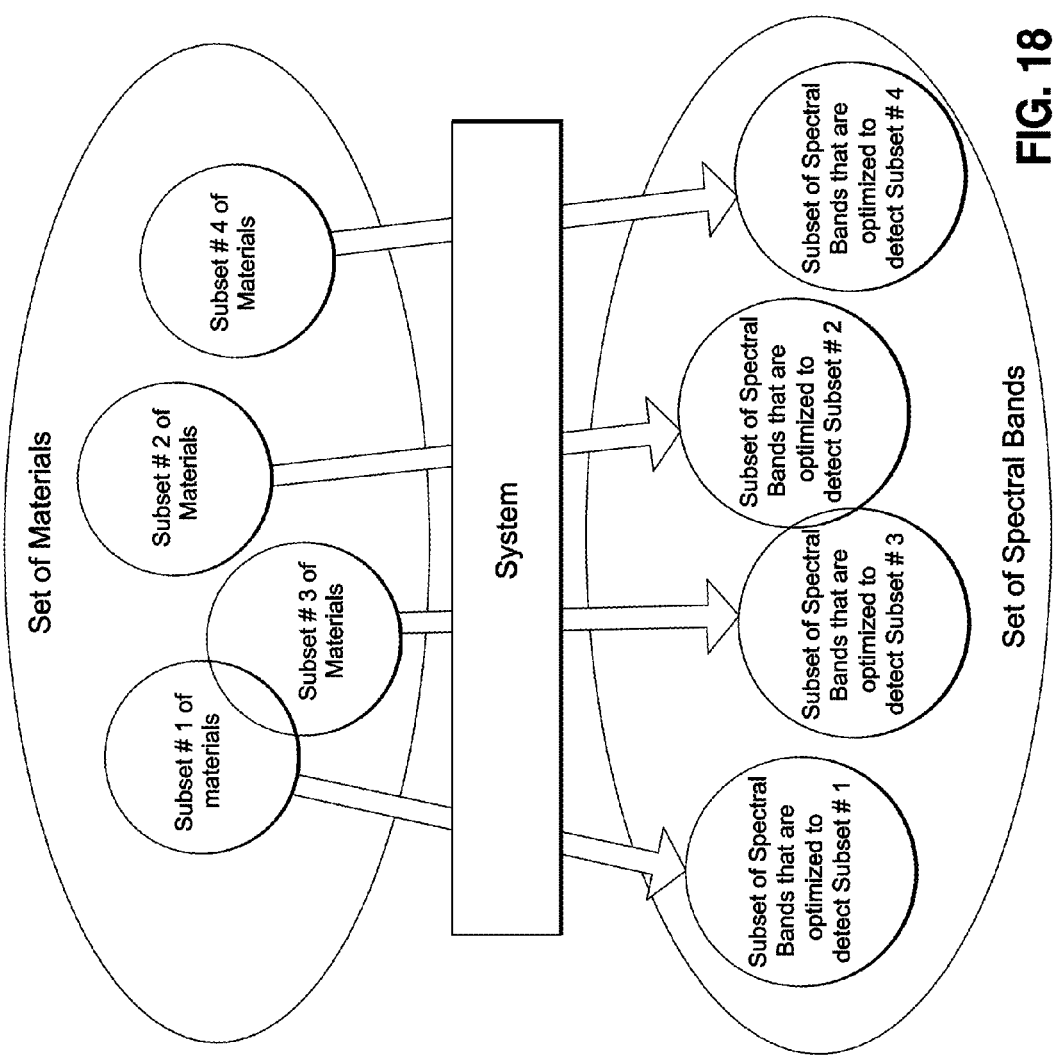
FIG. 18 illustrates some possible overlaps in subsets of materials in a given set of materials and some possible overlaps in subsets of spectral bands, each designed to differentiate between materials in respective ones of subsets of materials.

FIG. 18 illustrates some possible overlaps in subsets of materials in a given set of materials and some possible overlaps in subsets of spectral bands, each designed to differentiate between materials in respective ones of subsets of materials.

More specifically, as described hereinabove, a subset of spectral bands are selected that are optimized to classify the materials in a group of materials. The optimized subset of spectral bands allows classification of the materials in the group of materials without a significant loss of classification accuracy. Thus, if there is a set of materials, a set of spectral bands, and a first group, subset #1, of materials that are to be classified, the system determines the subset of spectral bands that are optimized to detect subset #1. Different optimized subsets of spectral bands may be generated for the different subsets of materials. For example, even though subset #1 and subset #3 overlap, their respective optimized subsets of spectral bands do not overlap. Also, although subset #2 and subset #3 do not overlap, their respective optimized subsets of spectral bands do overlap.

FIG. 18 illustrates some possibilities for this overlap. This figure illustrates some possible overlaps in subsets of materials in a given set of materials (such as Nickel, Titanium, Tin, Aluminum and Copper) and some possible overlaps in subsets of spectral bands, each designed to differentiate between materials in respective ones of the subsets of materials (such as a differentiation between each of the ten (10) combinations of two materials chosen from the five materials of Nickel, Titanium, Tin, Aluminum and Copper).

One advantage provided by the arrangements described herein is finding a small number of spectral bands (or equivalently filters), which can be used to image materials without compromising on material classification accuracy. The more filters in the image capture system, the longer it takes to image a material. Additionally, usage of images corresponding to additional filters does not necessarily increase the material classification accuracy as shown above.

Another advantage is the capability of reducing cost through replacing the LCTF of 32 bands by a filter wheel in which 5 selected filters can be used, such as for camera 924 in FIG. 9. The price of an LCTF for the visible wavelength range is in the order of $10,000, whereas the price for a broadband camera coupled with a simple filter wheel is much lower, thus allowing for deployment in multiple industrial inspection sites in the field.

In addition, knowing the five filters needed can allow for the design of a color filter array for material sensing. Such a filter would provide portability in robotics applications.

Other advantages which stem from the above are reducing the number of images captured and consequently the dimensionality of the feature vectors needed to represent the materials in the classification engine. For example, in a binary material classification case with one illumination setup, the capture time for one image would be 32 bands×5 sec=160 sec=2.67 minutes. Using only 5 bands, the capture time would be 5 bands×5 sec=25 sec. Additionally, the sizes of the feature vectors for the 32 band case and the 5 band case are about 100 Mb and 16 Mb respectively. This implies that the sizes of the feature vectors are reduced by a factor of 7 upon using a subset of filters. Note that in this example case, very few images are used, while in a factory or robotic industrial application setting, the number of images can scale considerably.

Reducing the sizes of the feature vectors would result in decreasing both the training and test time. Decreasing the training time would be useful in case of deployment of an online training material classifier. Decreasing the test time is important when a classifier is deployed in a factory setting for recycling.

As shown above, there has been described a technique for filter/spectral band selection using the captured images under multiplexed illumination. With such a technique, the number of filters can be reduced from 32 down to 3 or 4 or-5 while still achieving high classification accuracy. Some advantages include the replacement of the LCTF; and a reduction in capture time, image storage space, and classification time.

FIGS. 22 to 27 illustrate example aspects of computing a feature vector representation for an image slice based on clustering of low-level features of the image slice. As mentioned above, one problem with the conventional feature vector is its high dimensionality, particularly due to per-pixel classification of images. For example, given a relatively modest database of 150 image slices having 1000× 1000 pixels in size for 100 material samples of 10 main categories, the number of samples would be 1000×1000× 150=150×106, for a dimensionality of the same 150×106. The space required to store these samples, and the power and time required to process them, scale with the number of materials, leading to an impractical situation. The foregoing situation is addressed by computing a feature vector representation for an image slice based on clustering of low-level features of the image slice. The feature vector representation may also be referred to herein as an "image-level feature".

Figure 22:
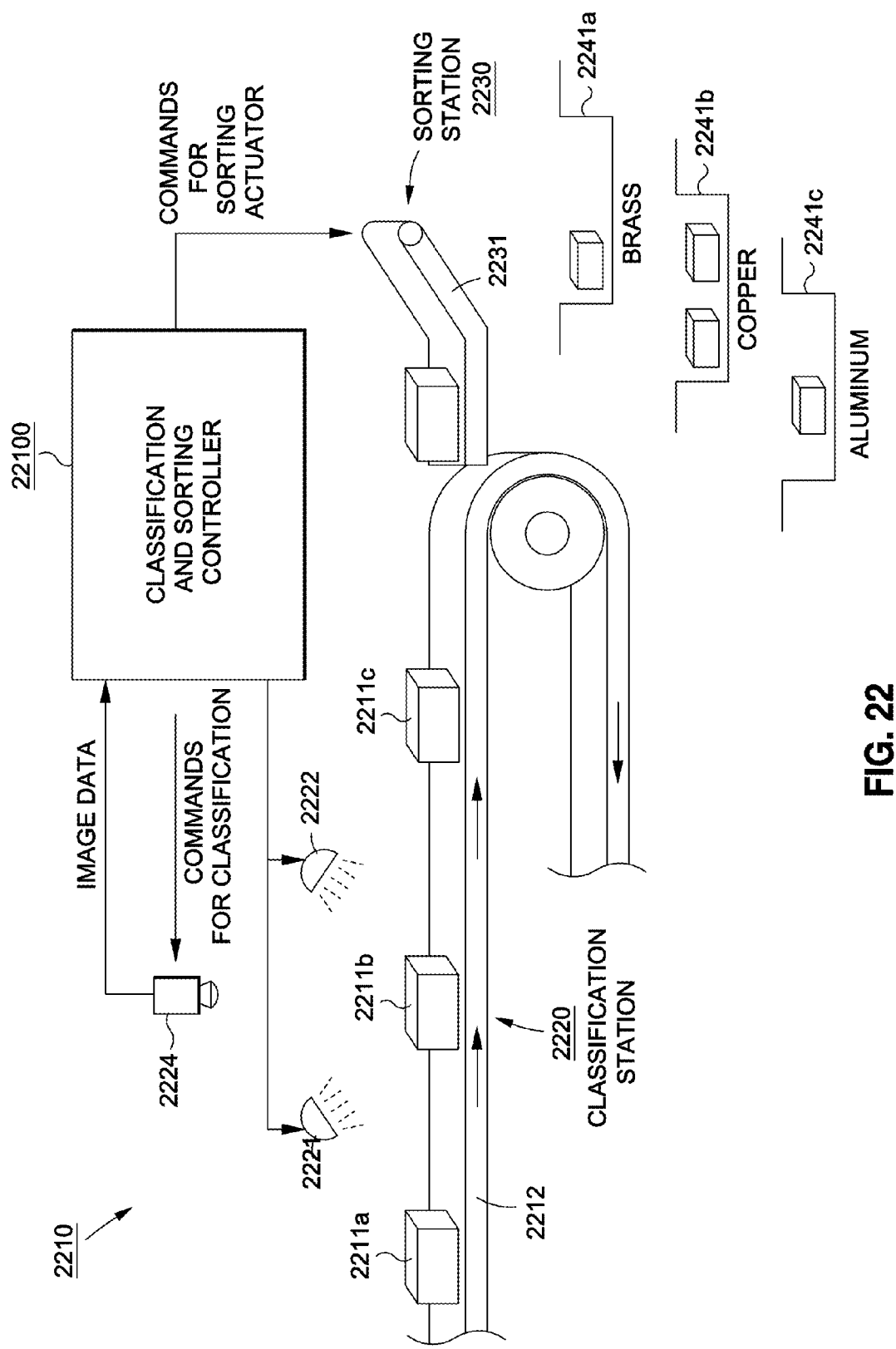
FIG. 22 is an example embodiment of a classification system according to the description herein, in the form of a recycling system in which objects to be recycled are classified according to the materials from which the objects are fabricated, and the classified objects are sorted for recycling according to their material classification.

FIG. 22 is an example embodiment of a classification system according to the description herein, in the form of a recycling system 2210 in which objects to be recycled are classified according to the materials from which the objects are fabricated, and the classified objects are sorted for recycling according to their material classification. As shown in FIG. 22, objects 2211a, 2211b, etc. are conveyed on a conveyor mechanism 2212 to a classification station 2220, where the objects are classified according to their material, and thence to a sorting station 2230, where the objects are sorted according to their material classification. Classification station 2220 includes plural light sources 2221 and 2222, together with a camera 2224 for capturing images of objects positioned at classification station 2220. The object at the classification station is illuminated individually by each of the plural light sources under control of classification and sorting controller 22100, and camera 2224 captures one or more images for each individual illumination. Under control of the classification and sorting controller 22100, a classification is made for the material from which the object is fabricated.

Conveyor mechanism 2212 continues to convey the object to sorting station 2230, where sorting actuator 2231 sorts the objects according to the material classification. Sorting is controlled by classification and sorting controller 22100, which commands sorting actuator 2231 to sort the classified objects into multiple receptacles 2241a, 2241b and 2241c.

In this example embodiment, material classification differentiates between different types of metals from which the objects are fabricated, such as brass, copper and aluminum. Naturally, it will be understood that this is a non-limiting example. In other embodiments, material classification could differentiate between metal, plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

A description will now be made of the positioning of the plural light sources and the camera relative to the object at the classification station, the spectral content of the light sources, and the spectral sensitivity of the camera.

Figure 23:
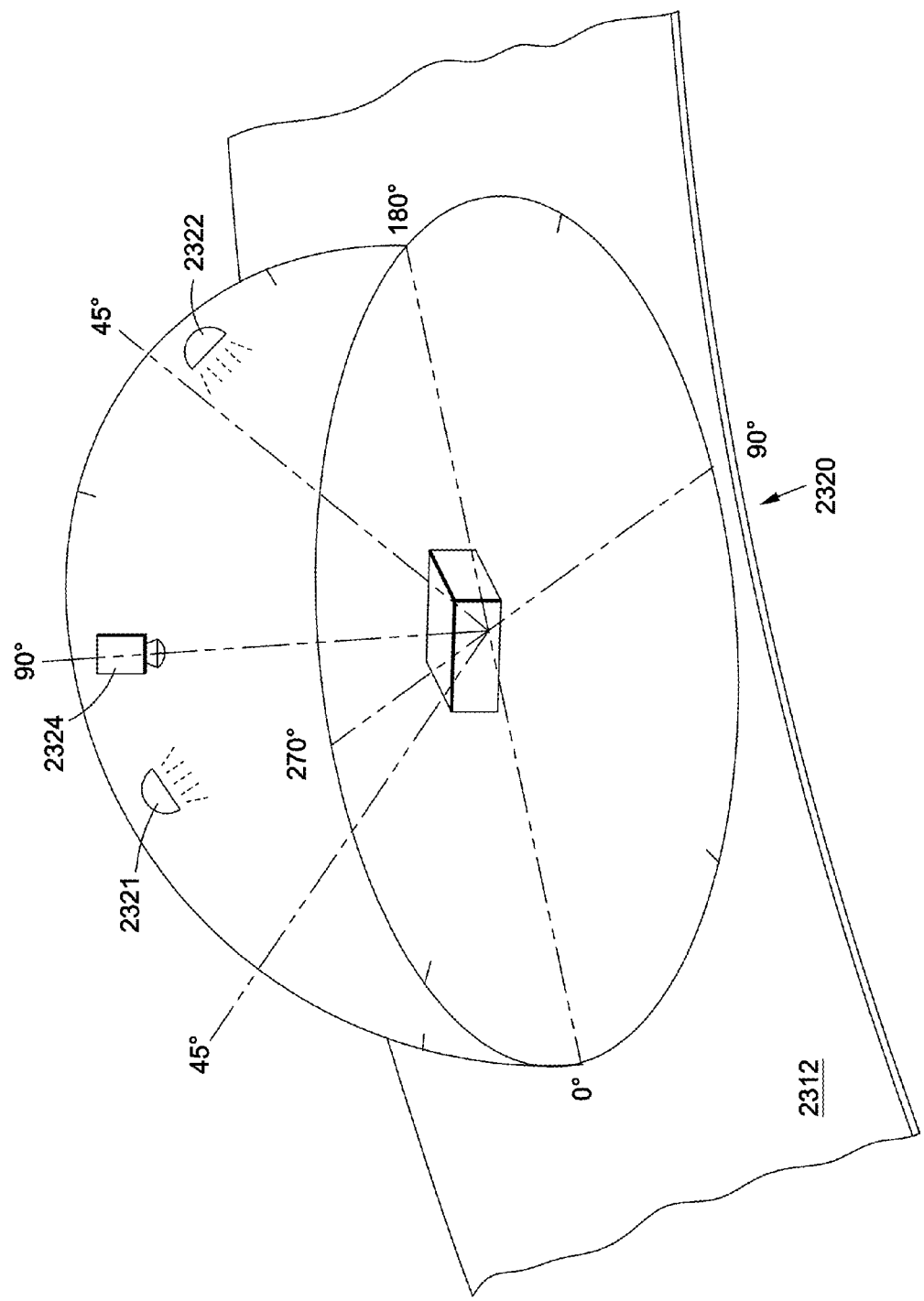
FIG. 23 is a more detailed view of an object being subjected to classification at a classification station of the FIG. 22 view.

FIG. 23 is a more detailed view of an object on conveyor mechanism 2312 at classification station 2320. In this figure, an angular coordinate system has been superimposed for purposes of explanation, and for purposes of explaining the angle of incidence for each of light sources 2321 and 2322, and the angle of exitant for light reflected from the object and imaged by camera 2324. In this example embodiment, light source 2321 is positioned at a first incident angle, and light source 2322 is positioned at a second incident angle. Also in this example, camera 2324 is positioned at an exitant angle of 90 degrees elevation.

With respect to the spectral content of light sources 2321 and 2322, in one embodiment, each light source is formed from an LED cluster with six (6) differently-colored LEDs arranged circularly with a white LED in the center. In this embodiment, the LEDs cover the visible wavelength range, and include the colors of blue, green, yellow, red, orange and the afore-mentioned white. In other embodiments, it might be helpful to include LEDs beyond the visible wavelength, such as LEDs which emit light in the ultraviolet or infrared range. The precise spectral content of the light sources in general will assist in distinguishing between different classifications of materials.

Camera 2324 in this embodiment is a RGB camera, and it thus exhibits spectral sensitivity in each of the red, green and blue wavelengths. In other embodiments, camera 2324 might include spectral sensitivity in wavelengths other than red, green, and blue, or it might include a monochrome camera which exhibits broad spectral sensitivity across the visible and near-visible ranges of wavelengths, possibly along with a liquid crystal tunable filter.

As shown in FIG. 23, this example embodiment includes two (2) light sources and one (1) camera. In general, in order to facilitate rapid classification of materials, such as real-time classification of materials, the number of light sources and the number of cameras is relatively small, such that materials can be classified with only a few illuminations and with only a few images for each such illumination. Preferably, the number of light sources should range between two and five, inclusive, most preferable two or three light sources, and the number of cameras should range between one and two, inclusive, most preferably one camera.

Although in this embodiment the spectral content of each individual light source is identical to all others, it should be understood that the spectral content of the light sources might differ from each other. Likewise, in embodiments where there are plural cameras, although the spectral sensitivities of the cameras might match, it is also possible for the spectral sensitivities to differ. Certain materials might provide a stronger response depending on which LED (red, green, etc.) is illuminating, the angle (45° incident angle vs. 90° incident angle), and so on. While how the surface reflects light is a characteristic of the surface despite such variations, some combinations of colors/angles and the like will provide a clearer or stronger response than others. Generally, it might be the case that angles of illumination where the light strikes the material at a more direct angle (i.e., 90°) illuminate more surface and are therefore more optimal, since the reflections returned have more pixels that are not dark. Additional details of variances in illumination angles and the like are discussed in U.S. application Ser. No. 14/092,492, entitled "Material Classification Using Spectral BRDF Slices", the contents of which are incorporated herein by reference.

Under control of classification and sorting controller 22100, each individual LED in each individual light source of the plural light sources is illuminated individually and independently of other LEDs in the light source, and independently and individually of other light sources and other LEDs in those other light sources. For each such illumination, camera 2324 captures an image of light reflected from the object at the exitant angle. The captured images are collected by classification and sorting controller 22100, and are analyzed thereby, such as by deriving one slice of the so-called bidirectional reflectance distribution function (BRDF). The BRDF is a four-dimensional function that depends on incident and exitant angles, and defines how light is reflected from the surface of an object. With a camera positioned at a fixed exitant angle, only a "slice" of the BRDF is obtained.

Based on the BRDF slices and other analysis, a feature extraction algorithm is applied to extract feature vectors for each image, as described more fully below with respect to FIGS. 25 to 27 and the accompanying text. The extracted feature vectors can then be fed to a trained classification engine, and classification and sorting controller 22100 can obtain a classification of the material from which the illuminated object is fabricated.

Figure 24:
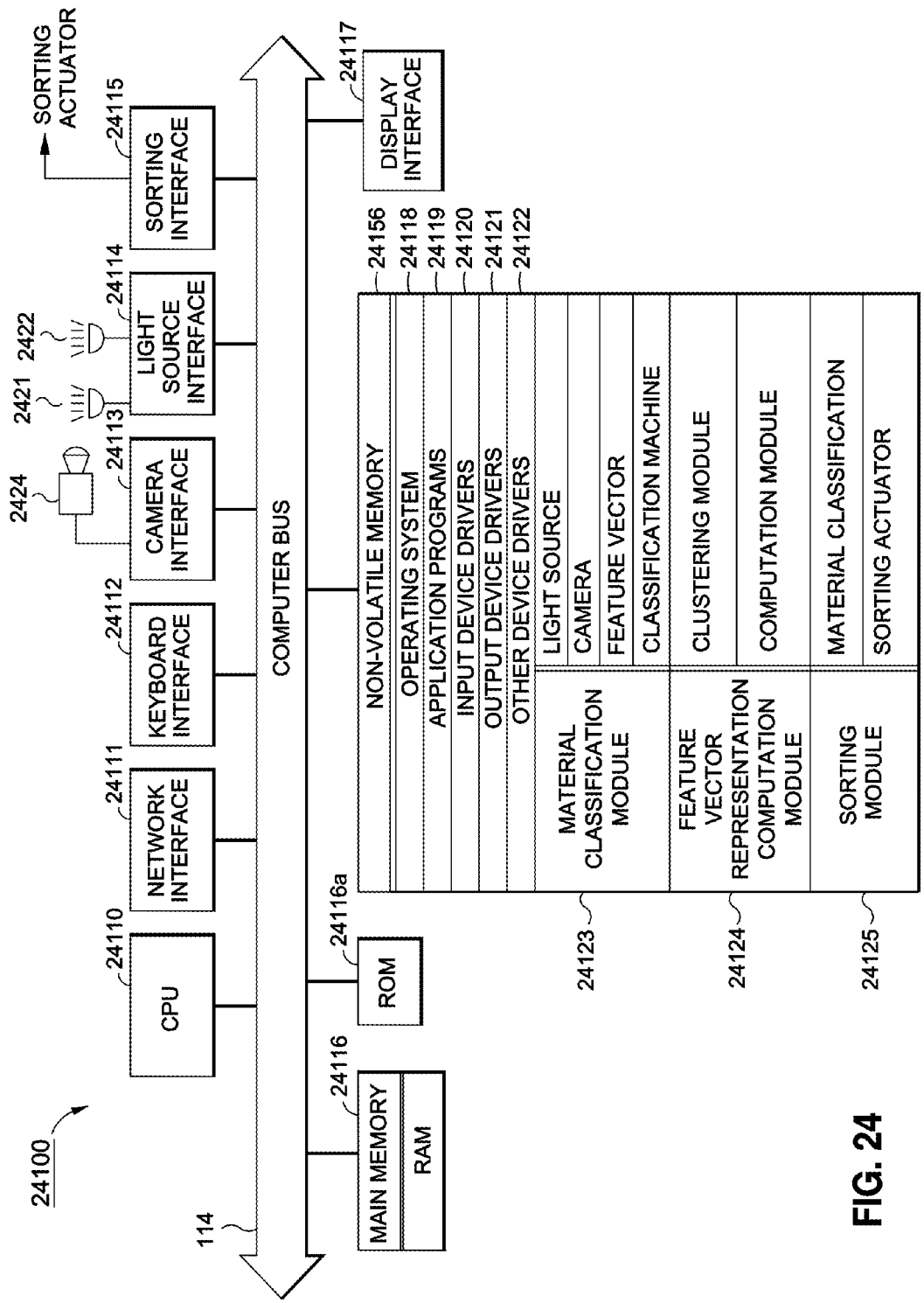
FIG. 24 is a view for explaining the architecture of a classification and sorting controller according to an example embodiment.

FIG. 24 is a view for explaining the architecture of classification and sorting controller 24100.

As shown in FIG. 24, classification and sorting controller 24100 includes central processing unit (CPU) 24110 which interfaces with computer bus 24114. Also interfacing with computer bus 24114 are non-volatile memory 24156 (e.g., a hard disk or other nonvolatile storage medium), network interface 24111, keyboard interface 24112, camera interface 24113, random access memory (RAM) 24116 for use as a main run-time transient memory, read only memory (ROM) 24116a, and display interface 24117 for a display screen or other output.

RAM 24116 interfaces with computer bus 24114 so as to provide information stored in RAM 24116 to CPU 24110 during execution of the instructions in software programs, such as an operating system, application programs, image processing modules, and device drivers. More specifically, CPU 24110 first loads computer-executable process steps from non-volatile memory 24156, or another storage device into a region of RAM 24116. CPU 24110 can then execute the stored process steps from RAM 24116 in order to execute the loaded computer-executable process steps. Data, also, can be stored in RAM 24116 so that the data can be accessed by CPU 24110 during the execution of the computer-executable software programs, to the extent that such software programs have a need to access and/or modify the data.

As also shown in FIG. 24, non-volatile memory 24156 contains computer-executable process steps for operating system 24118, and application programs 24119, such as graphic image management programs. Non-volatile memory 24156 also contains computer-executable process steps for device drivers for software interface to devices, such as input device drivers 24120, output device drivers 24121, and other device drivers 24122.

Non-volatile memory 24156 also stores a material classification module 24123 and a sorting module 24125. The material classification module and the sorting module comprise computer-executable process steps for material classification of an object fabricated from an unknown material, and for sorting the object based on the material classification.

In addition, non-volatile memory 24156 stores feature vector representation computation module 24124, which includes a clustering module for clustering low-level features of each image slice into at least two clusters, and a computation module for computing an intermediate feature vector representation for each image slice with entries that are weighted means of the clusters. These processes are described more fully below.

The material classification module 24123 includes a corresponding plurality of modules for control of the light sources, for control of the camera(s) and for gathering of image data of such camera(s), a module for derivation of feature vectors from, e.g., the intermediate feature vector representation, and a classification machine. The classification machine accepts as inputs the feature vectors derived by the feature vector module, and provides a classification of the material from which the object under inspection is fabricated. Sorting module 24125, for its part, includes a corresponding plurality of modules related to input of material classification from the classification machine, and actuation of the sorting mechanism based on the classification.

The computer-executable process steps for these modules may be configured as part of operating system 24118, as part of an output device driver in output device drivers 24121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

More details concerning the nature of the feature vector algorithm and the classification machine are provided below.

Figure 25:
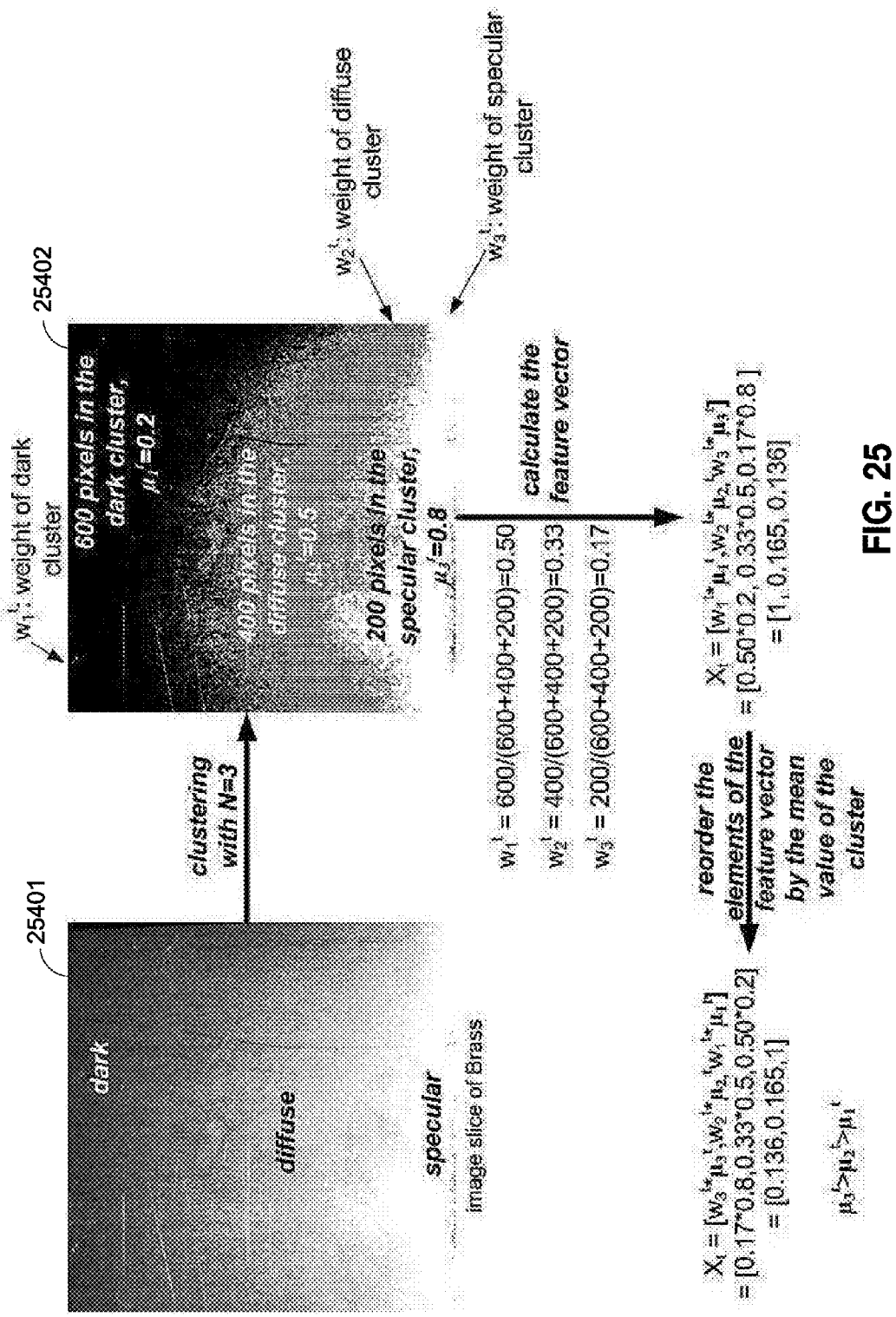
FIG. 25 is a view for explaining material classification according to an example embodiment.

FIG. 25 is a view for explaining material classification according to an example embodiment.

In FIG. 25, image slice 25401 is an input image slice of a material from which a feature vector will be generated. In the example shown in FIG. 25, image slice 25401 corresponds to brass, although various other materials are of course possible. Image slice 25401 includes pixels which generally appear to correspond to three categories, namely dark, diffuse, and specular pixels. Thus, in this example, the low-level features of each image slice are clustered into at least three clusters including a first cluster for specular reflections, a second cluster for diffuse reflections, and a third cluster for dark reflections.

As shown in FIG. 25, clustering is performed on input image slice 25401. In this example, K-means clustering is performed on low-level features of the pixels with the number of clusters N specified as N=3. Accordingly, according to this example, clustering includes application of K-means clustering on low-level features for each image slice. Generally, K-means clustering aims to partition observations into N clusters in which each observation belongs to the cluster with the nearest mean (or "center"), serving as a prototype of the cluster. In the examples that follow, the low-level features include pixel intensity values of the BRDF image slices. Nevertheless, it should be understood that various other types of low-level features could be used. Moreover, other clustering methods could be used. For example, the intermediate feature vectors could be computed by using an algorithm selected from a group, including, but not limited to, K-means and Gaussian Mixture Models. In one embodiment, rather than inputting the number of clusters, the cluster means or centers can be specifically input. In addition, N can also be varied.

In that regard, the specified number of clusters N has an effect on the accuracy of the feature vector. Generally, N=3 is desirable, since most images have at least or near 3 types of reflections. However, other numbers could be used. For example, N=4 would mean that one of the specular, dark and diffuse clusters will be split into two clusters, and thus some images might lose commonality if they fall into different clusters of the split cluster. Thus, in such a case, material classification would include material sub-categories, and the K-means clustering would derive more than three clusters. In particular, the low-level features would be clustered into clusters for specular reflections, diffuse reflections and dark reflections, at least one of which including a sub-cluster. On the other hand, in some cases N=2 might be desirable if the image only contains two types of reflections (or significant numbers thereof), e.g., if the image only includes specular and diffuse reflections. In some embodiments, the number of clusters can be selected automatically by using the clustering algorithm.

The clustering naturally identifies pixels belonging to each cluster of the three clusters, as shown in clustered image 25402. For example, in this example, 600 pixels are clustered into the dark (dark pixel) cluster, 400 pixels are clustered into the diffuse cluster, and 200 pixels are clustered into the specular cluster. As also shown in clustered image 402, the dark cluster has a mean pixel value $\mu_1^t$ of 0.2 (e.g., the mean pixel intensity), the diffuse cluster has a mean pixel value $\mu_2^t$ of 0.5, and the specular cluster has a mean pixel value $\mu_3^t$ of 0.8. In this embodiment, therefore, important features are extracted from the whole image slice, rather than needing to separate or otherwise segment portions of the image, such as by cropping out segments which include dark pixels. Naturally, the number of pixels in each cluster and mean pixel values mentioned above are only examples, and other numbers and values might be obtained.

Once the pixels are sorted into the clusters, weights can be assigned to each cluster, e.g., $W_1^t$ corresponding to the weight of the dark cluster, $W_2^t$ corresponding to the weight of the diffuse cluster, and $W_3^t$ corresponding to the weight of the specular cluster. In this example, each of weights $W_1^t$, $W_2^t$, and $W_3^t$ equals the number of pixels in the corresponding cluster divided by the total number of pixels. Thus, as shown in FIG. 25, $W_1^t$=600 pixels in the dark cluster divided by 1200 total pixels=0.5, $W_2^t$=400/1200=0.33, and $W_3^t$=200/1200=0.17.

To calculate an intermediate feature vector, the weight for each cluster is multiplied by the mean for each cluster, and the results of this computation for each cluster are concatenated. Thus, for example, the vector can be written as $X_t = [\mu_1^{'t} * W_1^t, \mu_2^{'t} * W_2^t, \ldots, \mu_N^{'t} * W_N^t]$, where $X_t$ is the feature vector representation of image slice t and N is the number of clusters, where $\mu_1^t$, $\mu_2^t$, and $\mu_3^t$ are the mean pixel values for each cluster as discussed above, and $W_1^t$, $W_2^t$, and $W_3^t$ are the weights, or percentage of pixels in each cluster for slice t.

To generate the feature vector, the elements of the intermediate feature vector are sorted by the mean value of the cluster. As described above, the dark cluster has a mean pixel value $\mu_1^t$ of 0.2, the diffuse cluster has a mean pixel value $\mu_2^t$ of 0.5, and the specular cluster has a mean pixel value $\mu_3^t$ of 0.8. Thus, reordering these elements in $X_t$ from highest to lowest mean value, results in $X_t = [\mu_3^{'t} * W_3^t, \mu_2^{'t} * W_2^t, \mu_1^{'t} * W_1^t] = [(0.17*0.8), (0.33*0.5), (0.5*0.2)] = [0.136, 0.165, 1]$. Accordingly, feature vector representations of each slice are computed by sorting all entries of the intermediate feature vector representations by the mean of the corresponding clusters.

In this regard, it should be noted that the elements can be sorted in other ways, although generally it is helpful if the manner of the sorting is the same for all image slices. Nevertheless, in some cases the elements of the intermediate feature vector can be used to train a classifier even if non-ordered, although such training often becomes more complex.

Figure 26:
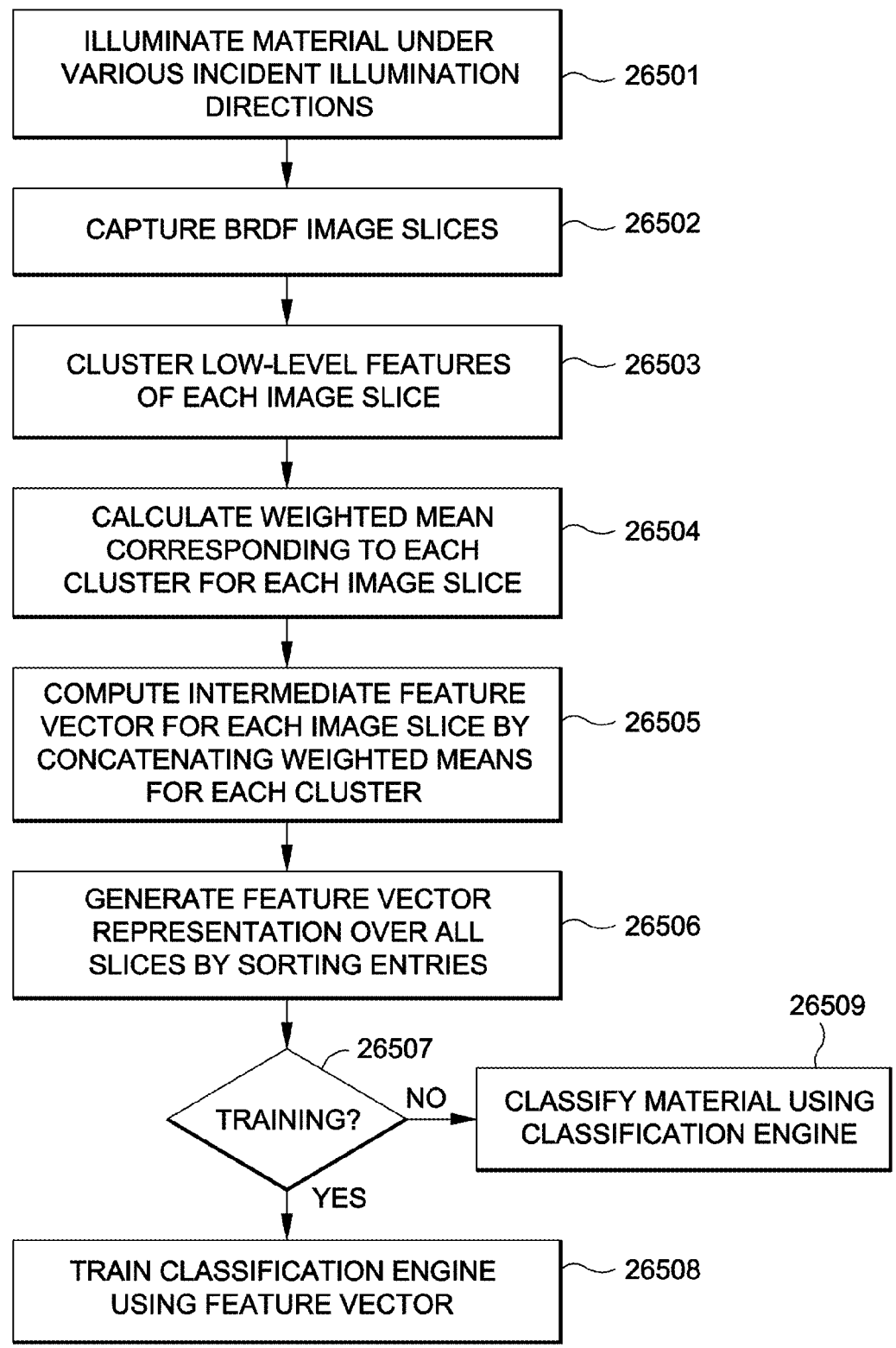
FIG. 26 is a flow diagram for explaining material classification according to an example embodiment.

FIG. 26 is a flow diagram for explaining material classification according to an example embodiment.

Briefly, in FIG. 26, feature vector representations are computed for BRDF image slices in a database of known materials captured under a relatively large number of incident illumination directions. Low-level features of each image slice are clustered into at least two clusters. An intermediate feature vector representation is computed for each image slice with entries that are weighted means of the clusters.

In more detail, in step 26501, a material is illuminated under various incident illumination directions. In particular, as mentioned above with respect to FIG. 23, each individual LED in each individual light source of the plural light sources is illuminated individually and independently of other LEDs in the light source, and independently and individually of other light sources and other LEDs in those other light sources. For each such illumination, camera 2324 captures an image of light reflected from the object at the exitant angle.

In step 26501, it does not matter whether the imaged material is unknown or known. Moreover, whether the material is a known training material or an unknown material to be classified, the process is the same from steps 26501 to 26506.

In step 26502, bidirectional reflectance distribution function (BRDF) slices are captured. In particular, one slice of the BRDF may be derived. The BRDF is a four-dimensional function that depends on incident and exitant angles, and defines how light is reflected from the surface of an object. With a camera positioned at a fixed exitant angle, only a "slice" of the BRDF is obtained.

In step 26503, low-level features of each image slice are clustered. In particular, as discussed above with respect to FIG. 25, K-means clustering is performed on low-level features of the image slice to identify pixels belonging to each cluster of N clusters (N being input before clustering).

In step 26504, a weighted mean corresponding to each cluster for each image slice is calculated based on the pixel values in the cluster, and in step 26505, an intermediate feature vector representation is computed for each image slice by concatenating the weighted means for each cluster, as also described above with respect to FIG. 25.

In step 26506, the feature vector representation is generated by sorting the entries of the intermediate feature vector representation, as described above. For example, the elements of the intermediate feature vector representation can be sorted from highest to lowest mean value.

At this point, the processing to be performed depends on whether the material under consideration is a known material used for training a classification engine such as a support vector machine, or whether the material under consideration is an unknown material which is being classified. Thus, in step 26507, there is a determination of whether the material is being used for training. If the material is a known material, then the material is being used for training, and the process proceeds to step 26508. On the other hand, if the material is an unknown material to be classified, the process proceeds to step 509.

In step 26508, the classification engine is trained using the feature vector generated in step 26506. For example, a support vector machine (SVM) may be trained on the set of features of the feature vector. Thus, the approach can be used to train a classifier, and the trained classifier can be used to label data. In one example, as discussed below, the SVM can use 75% of the samples for training, and 25% for testing. At some point, there may be a need to label the training data, i.e., to input, after deriving the feature vectors, which feature vector corresponds to which material, although such labeling could also be done with an unsupervised approach. Thus, in one embodiment, a classification engine is trained for material classification using the computed feature vector representations of labeled training data. For example, the database of labeled training data can be labeled according to classification of material by calculating a probability function based on determining a correlation between a sample signature and a set of pre-labeled signatures in a database.

The classification engine may be configured to make a decision for cases with a pre-determined level of confidence in the prediction. When a decision is not made, the sample can be sent to a human for labeling.

In addition, although some embodiments may be based on a one-time training of the classification engine, in other embodiments, the classification engine may be trained more than once, or may be updated at intervals, such as by training on-line with new material samples. In this regard, and particularly with respect to objects not classified with confidence by the engine, and for which a manual classification was needed, the training for the classification engine can be updated using the manually-classified result.

On the other hand, if the feature vector is not used for training and the material is to be classified, the process proceeds to step 26509, where the material is classified using the classification engine. Specifically, the material for the unknown object is classified by applying the feature vector representation of the unknown object to the classification engine. Thus, according to this embodiment, an object fabricated from an unknown material is illuminated, and BRDF image slices for the illuminated object are captured. A feature vector representation is computed for the BRDF image slices of the object of unknown material, and the material for the unknown object is classified by applying the feature vector representation of the unknown object to the trained classification engine.

While the above example describes training the classification engine with the generated feature vector, other alternatives are possible. For example, the classification engine can be trained beforehand and/or offline with labeled training samples. In another example, the classification engine need not be trained at all, and classification can be performed directly on unlabeled samples. Put another way, the unknown materials can be classified directly using their features, without training the classification engine.

A number of examples of material classification will now be described, for better evaluation of the derived feature vector.

In the examples that follow, material classification performance is compared using the feature vector calculated as described above, referred to hereafter as the multispectral histogram of reflections (msHOR). For comparison, performance is also evaluated in cases of using a mean feature vector, as will be described shortly, and a per-pixel feature vector representation.

For the comparison, binary classification is performed. 25 sets of materials of two types are constructed using materials from the RIT database, which is a dataset of spectral BRDF's of material samples published in 2012 by RIT (http://compimg1.cis.rit.edu/data/metal/). The dataset contains 100 material samples of 10 main categories. The setup for image capture constitutes a dome of 25 clusters, with 6 LED's in each cluster. Each of the 25 sets comprises 15 sets of only non-ferrous metals and 10 sets of a combination of both non-ferrous and ferrous metals, which can be referred to as mixed metal sets. The non-ferrous metals are of three categories: four types of aluminum, brass, copper, and chromium. The mixed sets have additionally the following two ferrous metal categories: two types of steel and stainless steel. Table 1 shows the list of RIT sets used in the binary classification experiments.

TABLE 1

| RIT Metal Sets Considered |
| --- |
| Brass/Copper |
| AL2024/Brass |
| AL2024/Copper |
| AL7075/Brass |
| AL7075/Copper |
| AL5052/Brass |
| AL5052/Copper |
| AL6061/Brass |
| AL6061/Copper |
| AL2024/AL5052 |
| AL6061/AL7075 |
| Chromium/Brass |
| Chromium/Copper |
| AL7075/Chromium |
| AL6061/Chromium |
| Steel1/Steel2 |
| Steel1/Stainless steel |
| Steel2/Stainless steel |
| Brass/Stainless steel |
| Copper/Stainless steel |
| AL7075/Steel2 |
| Steel1/Chromium |
| AL7075/Stainless steel |
| Steel1/Copper |
| Steel1/Brass |

Table 1: The 25 two-class RIT metal sets used for evaluation. The first 15 sets comprise only non-ferrous metals, while the remainder 10 sets comprise both ferrous and non-ferrous metals.

For each material category, there are 4 samples. Therefore, there are 8 samples in total. Different combinations or folds of training and test data are chosen, such that for each fold, the test data contains one sample from each category. In total, 16 folds of training and testing data are considered, where 75% of the samples are used for training, and 25% are used for testing. Therefore for each fold, a training set would have 6 material samples, while a test set would have 2 samples. The classification accuracy computed is then taken to be the average over the accuracies computed for each of the test sets of the 16 folds. The classification accuracy is computed for each class and then averaged over the two classes, to obtain the average classification accuracy per set.

Two items need to be set when using an SVM: the kernel type and the C parameter. If the dataset contains only a small number of training samples, use of a linear kernel is sufficient. As for the parameter C, it can be set to, e.g., 10.

Classification accuracies compared using different feature vectors for 4 cases will now be described below.

Case 1

In the first case, the sorted vector described above (msHOR) is compared to a similar version of the vector in which no ordering of entries is performed. The latter case implies that that the feature vectors for each image slice as calculated in step 26505 above are simply concatenated to yield the overall feature vector, without sorting. This unsorted feature vector can be referred to as msHORv1. Table 2 shows results obtained for different numbers of clusters N, and for both types of feature vectors.

TABLE 2

| Feature vector type | Number of clusters | | | | |
|---|---|---|---|---|---|
| | N = 2 (%) | N = 3 (%) | N = 4 (%) | N = 5 (%) | N = 6 (%) |
| msHORv1 | 80 | 72 | 67 | 70 | 66 |
| msHOR | 80 | 81 | 75 | 75 | 75 |

Table 2: Classification accuracies obtained using an SVM with a linear kernel, over the RIT metal sets, for different numbers of clusters N=2, 3, 4, 5, and 6. Two types of feature vectors are considered: the first version of the Histogram Of Reflections (msHORv1), where the entries of the vectors are not ordered by descending order of cluster means; and the second version of the Histogram Of Reflections (msHOR), where the entries of the vectors are in decreasing order of cluster means.

Two observations can be made from the results shown. First, ordering the entries of the feature vector (msHOR) provides better classification performance than when the entries are not ordered (msHORv1). Second, the best classification accuracy is obtained for the msHOR feature vector and in the case N=3. This result supports the hypothesis that pixels of an image slice can generally be attributed to one of three types of reflections or clusters. The performance degrades significantly and plateaus when N increases for both the cases of msHOR and msHORv1.

Case 2

In the second case, the msHOR (when N=3) feature vector is compared to a mean feature vector. The mean feature vector is calculated by concatenating the means of the pixel intensity values over all image slices. The main drawback in using the mean feature vector is that an appropriate region, which is not full of non-reflective image regions for example, of each stack of image slices needs to be manually cropped to obtain the best image representation. The classification results are compared using the mean feature vector for three sets to the results obtained with using the msHOR features.

TABLE 3

| | Feature Vector Type | | |
|---|---|---|---|
| | Brass/Copper (%) | AL7075/Copper (%) | AL7075/Brass (%) |
| Mean | 91 | 78 | 75 |
| msHOR | 97 | 78 | 78 |

Table 3: Classification accuracies obtained when using an SVM with a linear kernel, for three binary sets of non-ferrous metals from the RIT database, as computed over 16 folds. Two types of feature vectors are considered: the mean where the feature vectors are computed as the concatenation of the means over cropped regions of the BRDF slice images; and the msHOR feature vector computed as the concatenation of the HOR feature vectors over all 150 slices.

Table 3 shows that the classification accuracies obtained when using the new feature vector are as at least the same or higher than when using the mean feature vector. In this regard, it can be noted the mean feature vector is 150 dimensions, while the msHOR feature vector is 450 dimensions (150 for each type of reflectance).

Case 3

In order to gain a better understanding of the performance of the msHOR in classifying the 25 sets of metals as shown in Table 1, another version of the mean feature vector can be calculated, referred to as Mean_v2. As mentioned earlier, the original mean feature vector requires manual cropping for each image slice after identifying the appropriate region for cropping. As this is tedious to perform in practice for all materials, the mean feature vector Mean_v2 can be calculated across the full image without cropping, and the means from all slices can be concatenated. Table 4 shows the average classification accuracy over the 25 sets in the case of using each feature vector. It should be noted the dimensional size of this Mean_v2 feature vector is 150 D, while that of msHOR is 450 D.

TABLE 4

| Feature Vector Type/Binary set | Overall (%) |
|---|---|
| Mean_v2 | 76 |
| msHOR, N = 3 | 81 |

Table 4: Classification accuracies obtained using an SVM with a linear kernel, over all 25 binary sets of metals from the RIT database, as computed over 16 folds. Two types of feature vectors are considered: the mean where the feature vectors are computed as the concatenation of the means over the BRDF slice image pixel intensity values; and the msHOR feature vector.

Thus, in this example case, the msHOR is more accurate than the Mean_v2 feature vector.

Case 4

Case 4 is directed to evaluation of a per-pixel feature vector representation. In particular, FIG. 27 depicts results when classifying brass and copper samples using feature vectors comprising the image pixels, and specifically using different numbers of pixels, starting 1 pixel per image to 22500 pixels.

Figure 27:
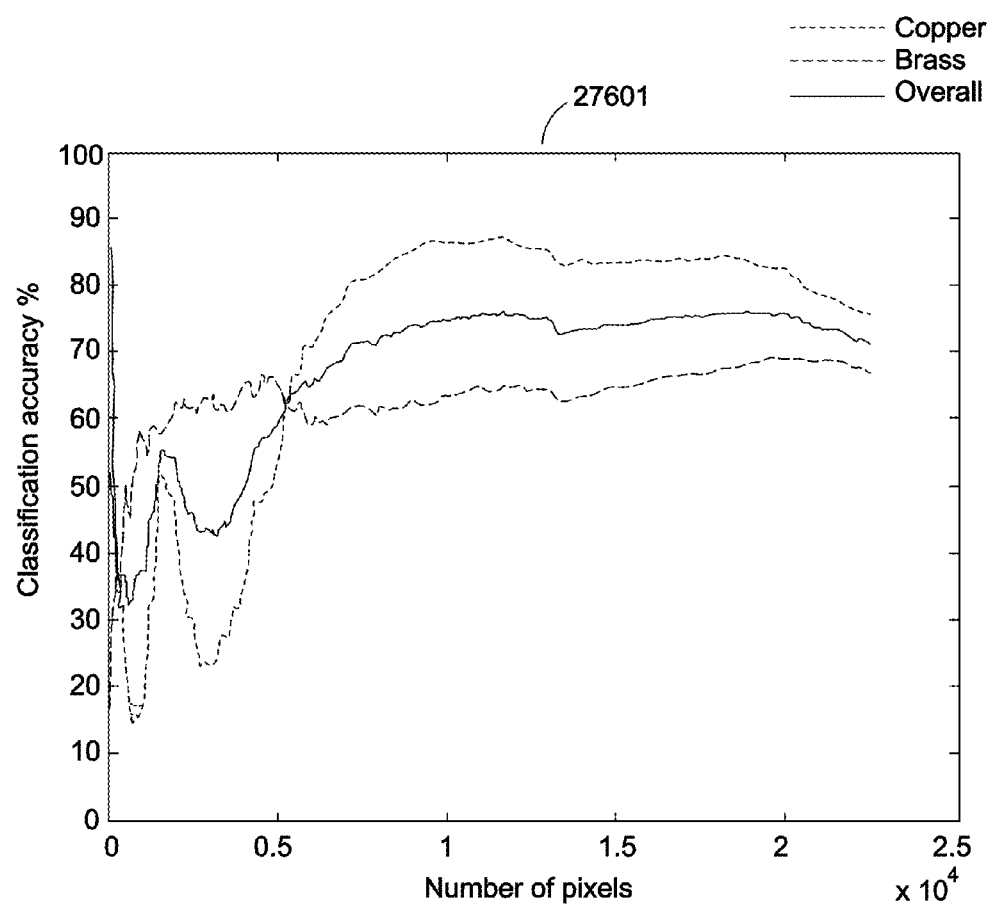
FIG. 27 is a view for explaining accuracy of a material classification according to an example embodiment.

In that regard, FIG. 27 depicts accuracies computed for classifying brass and copper samples which are comprised of different numbers of pixels. The reported accuracies are for the brass and copper categories as well as the mean accuracy for both, as a function of the number of pixels.

FIG. 27 shows how classification accuracy varies with the change in the number of pixels taken. The highest overall classification accuracy obtained was 76% when using 11,701 pixels. Thus, per-pixel feature vector representation does not necessarily provide as good of accuracy as the msHOR. Moreover, as described above, the space required to store the samples and the power and time required to process them scale with the number of materials, and can be impractical.

In contrast, by computing a feature vector representation for an image slice based on clustering of low-level features of the image slice, it is ordinarily possible to represent the BRDF based features of material while substantially reducing the size of the data. Moreover, the BRDF based feature described herein relates as much as possible to the physical meaning of BRDF. This feature vector is computed for one image as a whole, and therefore used to obtain one label per image. It therefore differs from the approaches in the literature which attempt at classifying each pixel of a material sample.

Meanwhile, it is also ordinarily possible to reduce the dimensionality of the training and testing data used in the classification algorithm. This would result in decreasing both the training and test time. Decreasing the training time would be useful in case of, for example, deployment of an online training material classifier. Decreasing the test time is important when a classifier is deployed in a factory setting for recycling.

In addition, a conventional alternative to classifying each image as a whole is taking a mean feature vector, for example, to represent the material. However, such methods require manual cropping of appropriate image regions. Additionally, the classification results are sensitive to the cropped regions. On the other hand, the algorithm for the proposed feature vector ordinarily does not require manual cropping of image regions.

Still another example embodiment for material classification will now be described with respect to FIGS. 28 and 29. In particular, FIGS. 28 and 29 illustrate an example embodiment for material classification in which the aforementioned techniques may be combined to customize a material classification, and which may further include classification which further uses a texture feature.

Figure 28:
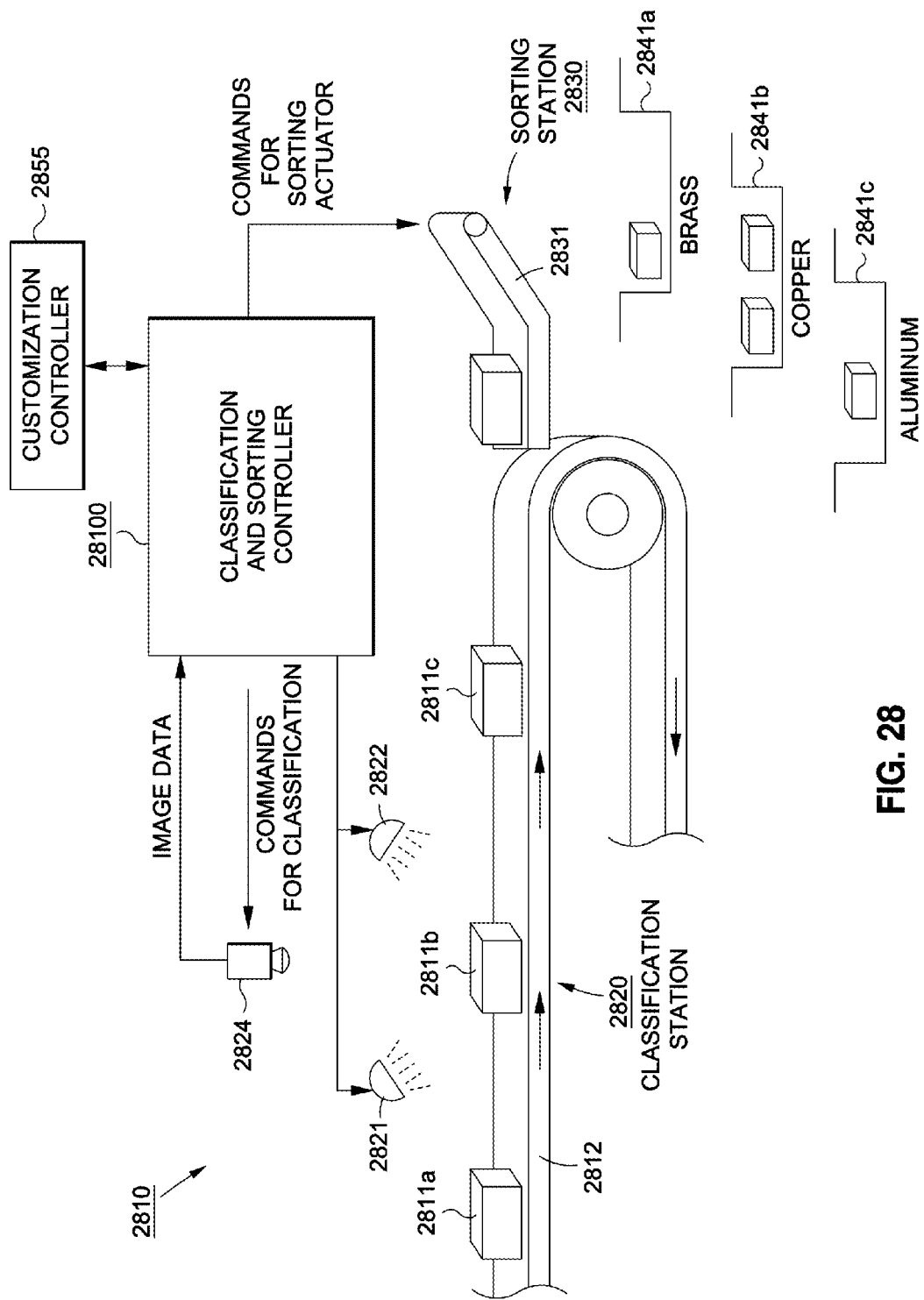
FIG. 28 is an example embodiment of another classification system according to the description herein, in the form of a recycling system in which objects to be recycled are classified according to the materials from which the objects are fabricated, and the classified objects are sorted for recycling according to their material classification.
Figure 29:
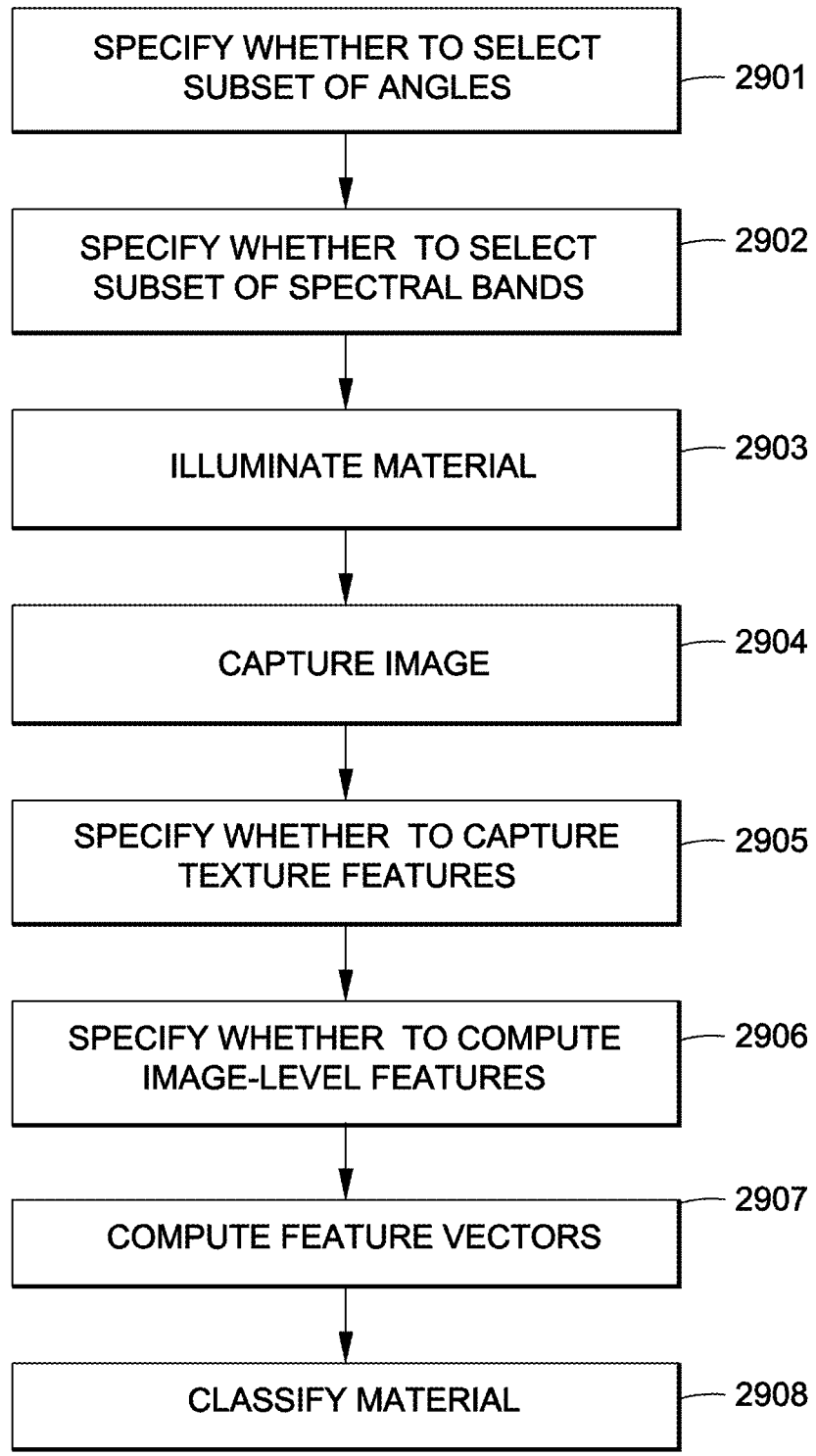
FIG. 29 is a flow diagram for explaining material classification according to an example embodiment.

FIG. 28 is an example embodiment of a classification system according to the description herein, in the form of a recycling system 2810 in which objects to be recycled are classified according to the materials from which the objects are fabricated, and the classified objects are sorted for recycling according to their material classification. As shown in FIG. 28, objects 2811a, 2811b, etc. are conveyed on a conveyor mechanism 2812 to a classification station 2820, where the objects are classified according to their material, and thence to a sorting station 2830, where the objects are sorted according to their material classification. Classification station 2820 includes plural light sources 2821 and 2822, together with a camera 2824 for capturing images of objects positioned at classification station 2820. The object at the classification station is illuminated individually by each of the plural light sources under control of classification and sorting controller 28100, and camera 2824 captures one or more images for each individual illumination. Under control of the classification and sorting controller 28100, a classification is made for the material from which the object is fabricated.

Conveyor mechanism 2812 continues to convey the object to sorting station 2830, where sorting actuator 2831 sorts the objects according to the material classification. Sorting is controlled by classification and sorting controller 28100, which commands actuator mechanism 2831 to sort the classified objects into multiple receptacles 2841a, 2841b and 2841c.

As shown in FIG. 28, classification and sorting controller 28100 also communicates with customization controller 2855. Customization controller 2855 is hardware and/or software for receiving a selection of parameters to customize material classification, and controlling classification and sorting controller 28100 to perform classification based on the parameters. For example, the parameters may include a selection to select a subset of angles for classification, a selection to select a subset of spectral bands for classification, a selection to capture texture features, and a selection to compute image-level features (e.g., a feature vector representation for an image slice based on clustering of low-level features of the image slice as described above). These parameters may be received from another system, input by a user, or otherwise selected.

By customizing material classification in this manner, it is ordinarily possible to provide better control over the processes performed in the classification environment. For example, selecting a smaller subset of illumination angles of the object might be more effective with certain types of materials than others, while in other situations image-level features may be useful to reduce processor and memory loads. Put another way, it is ordinarily possible to provide customized classification which is better suited to the current needs of a user or system.

In this example embodiment, material classification differentiates between different types of metals from which the objects are fabricated, such as brass, copper and aluminum. Naturally, it will be understood that this is a non-limiting example. In other embodiments, material classification could differentiate between metal, plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

FIG. 29 is a flow diagram illustrating customized material classification according to an example embodiment.

Briefly, as shown in FIG. 29, an object is classified. Parameters for classification are accessed. The parameters include a selection to select a subset of angles for classification, a selection to select a subset of spectral bands for classification, a selection to capture texture features, and a selection to compute image-level features. The object is illuminated, and a feature vector is computed based on the parameters. The material from which the object is fabricated is classified using the feature vector.

In more detail, in step 2901, there is a specification of whether to select a subset of illumination angles. For example, an operator might use a keyboard, mouse or other input device to select whether to reduce the number of illumination angles. Similarly, in step 2902, there is a specification of whether to select a subset of spectral band(s). In step 2903, there is a specification of whether or not to capture texture features, and in step 2904, there is a specification of whether to compute image-level features.

Thus, the selected light sources N are specified, and so are the selected spectral bands M (using, e.g., the approaches discussed above). As such, the dataset considered is the N×M subset of the original dataset. If no light sources are specified, one light source is taken, so N=1; if no spectral band is specified, one band is taken, so M=1. Moreover, the use of texture and the corresponding feature vector are specified. If texture is used, the dimensionality of the feature vector for each image slice can be denoted by T and T is dependent on the texture feature used. If texture is not used, a 3D clustering based feature vector (e.g., of dimension C=3) can be used for each slice corresponding to a spectral band (as discussed above).

Material classification is performed following the same paradigm as described above. Thus, in step 2905, the material is illuminated. In step 2906, the feature vectors are computed, and in step 2907, the material is classified.

Thus, different scenarios of availability of spectral, angular, and texture information are considered for material classification. Table 5 lists examples scenarios and corresponding labels (for simplicity).

TABLE 5

| Label | Angular | Spectral | Texture |
|---|---|---|---|
| 000 | No | No | No |
| 001 | No | No | Yes |
| 010 | No | Yes | No |
| 100 | Yes | No | No |
| 011 | No | Yes | Yes |
| 101 | Yes | No | Yes |
| 110 | Yes | Yes | No |
| 111 | Yes | Yes | Yes |

Table 5: In Table 5, the labels of the different cases consider a combination of incident illumination angle, spectral band, and texture dimensions in feature computation for material classification. The first column indicates the label of the case considered in the study. Each of the second, third, and fourth columns indicate whether the incident illumination angle, spectral band, and texture dimensions are considered, respectively.

In one example, the texture feature used is the local binary pattern (LBP) as it has proven to be very successful in texture classification, as described in, e.g., T. Ojala et al, "Multiresolution gray-scale and rotation invariant texture classification with local binary patterns", IEEE Transactions on Pattern Analysis and Machine Intelligence, 24(7):971-987, 2002.

Briefly, $LBP_{P,R}$ is the LBP value of a neighborhood of P equally spaced pixels in a circular neighborhood of radius R. $g_c$ is the grayscale value of the center pixel of the neighborhood, $g_p$ (p=0, . . . , P−1) corresponds to the gray value of the P equally spaced pixels of the neighborhood. For example, it is possible to consider circular neighborhoods of, e.g., 8 equally spaced pixels with radius of 1. Next a 256 D histogram is computed over these features for an image, thus allowing for grayscale invariance spatially (T=256). In that regard, the rotational invariant version of the LBP features does not provide better classification performance which is expected. The positions of the different light sources provide captured images in different orientations, and this orientation difference is needed to distinguish between different metals.

Examples of feature vectors which may be calculated from the above framework will now be described.

000: One image slice from the 150 image slices is considered and its corresponding CB feature vector is computed. Since angle 12 appears most frequently among the selected angles as described above, we take the slice corresponding to the white LED in cluster 12 (another angle could also be used). This feature vector is 3 D as is the case for the CB feature calculated on one image (N=1, M=1, C=3).

001: Only the variation in texture is considered. Therefore, the 256 D LBP feature is computed for the same image slice considered in the 000 case (N=1, M=1, T=256).

010: Only the variation in spectral band dimension is considered. Therefore the CB feature vector is computed for all image slices corresponding to all spectral bands for one angle of illumination. The angle chosen is that of cluster 12 as it is most commonly selected by the algorithm described above. The CB feature vector is computed for the image slices corresponding to all 6 LEDs of this cluster. Therefore, the dimensionality of this feature vector is 3 (CB)×6 (images)=18 D (N=1, M=6, C=3).

100: Only the variation in incident illumination angle is considered. Therefore one image slice corresponding to one spectral band is taken for each of the incident illumination angles. The same image slice as in the 000 case is taken for each of the 25 LED clusters. The feature vector computed is the CB one. The dimensionality of this feature vector is 3 (CB)×25 (images)=75 D (N=25, M=1, C=3).

011: Variation in both spectral band and texture are considered. Therefore the texture features are computed for the image slices of all spectral bands corresponding to only one incident angle of illumination. The image slices taken are the same as in the 010 case, and the LBP feature is computed. The image slices considered correspond to cluster 12. The dimensionality of this feature vector is 256 (LBP)×6 (images)=1536 D (N=1, M=6, T=256).

101: Variation in both the incident illumination angle and texture is considered. Therefore the LBP features are computed for the image slices considered in the case 100. The dimensionality of this feature vector is 256 (LBP)×25 (images)=6400 D (N=25, M=1, T=256).

110: Variation in both the incident illumination angle and spectral band are considered. Therefore the CB feature vectors are computed for all spectral band image slices corresponding to all incident illumination angles. There are 25×6=150 image slices corresponding to the 150 LEDs. The dimensionality of this feature vector is 3 (CB)×150 (images)=450 D (N=25, M=6, C=1).

111: Variation in all three dimensions, angular, spectral band, and texture are considered. Therefore the LBP texture features are computed for all spectral band image slices corresponding to all incident illumination angles. This case is similar to the 110 case except that the CB features are replaced with LBP features. There are 150 image slices corresponding to the 150 LEDs. The dimensionality of this feature vector is 256 (LBP)×150 (images)=38400 D (N=25, M=6, T=256).

111c: This is similar to the 111 case, except that the texture features and CB features for all image slices are concatenated. In the previous case, only texture features are taken. There are 150 image slices corresponding to the 150 LEDs. The dimensionality of this feature vector is (3 (CB)× 150 (images)) (N=25, M=6, C=3)+(256 (LBP)×150 (images)) (N=25, M=6, T=256)=38850 D.

For each of the cases described above, material classification is performed for each of the cases described above using the same paradigm described above. Table 6 shows example classification accuracies for each case. In that regard, in this embodiment, an additional "Mixed" dataset is considered, comprising 15 sets of non-metals and metals.

TABLE 6

| Set Type | 000 | 001 | 010 | 100 | 011 | 101 | 110 | 111 | 11c |
|---|---|---|---|---|---|---|---|---|---|
| Metal | 63.9 | 65.9 | 70.9 | 76.9 | 70.0 | 72.1 | 79.6 | 70.1 | 80.2 |
| Mixed | 52.5 | 58.5 | 59.6 | 48.5 | 48.9 | 55.4 | 52.7 | 52.9 | 57.3 |
| All | 59.6 | 63.1 | 66.6 | 66.2 | 62.3 | 65.8 | 69.5 | 63.7 | 71.6 |

Table 6: In particular, Table 6 depicts mean classification accuracies, over the 25 metal sets in the first row, the 15 mixed sets in the second row, and overall in the third row. Nine types of feature vectors which take into account different variations in incident illumination angle, spectral, and texture are considered. They are labeled as 000, 001, 010, 100, 011, 101, 110, 111, and 111c and described above.

The first general observation which can be made is that the results corresponding to the case 000 perform the worst or at most similar to the worst case for the majority of the sets. This is to be expected because no texture, BRDF, nor spectral information is considered in this case. The 110 case is the same case as classifying the materials using the CB features. Concatenating the texture based and BRDF based features does not improve performance for the metals, but does for the non-metals (100 and 101). This is to be expected since for metals, it is the angular variation which provides a difference in the results, as shown in the table. Light reflected from metals varies across a metal but does not vary as much across a non-metal. Concatenating all features (111c) results in the highest classification accuracy for both metals and non-metals.

In another example embodiment, learning the optimal incident illumination for providing the most discriminability among materials may be achieved by performing a joint selection of both incident angle and wavelength.

This learning may be performed jointly for both angle and wavelength in two steps: per-material clustering and selecting incident angles using spectral BRDF images and searching for the optimal angles and wavelengths which maximize material discriminability.

In more detail, first, the optimal incident illumination, both angle and wavelength, may be jointly learned using spectral BRDF image slices of raw materials. Second, orientation invariant image-level feature vectors may be extracted which represent specular, diffuse and dark components of these slices, as described above with respect to, for example, FIGS. 23 to 26. Third, these feature vectors may be used to cluster angles by spectral BRDF images, as shown above, for example, at FIG. 25. This clustering allows for reduction in the search space of optimal angle and wavelength.

In an example aspect, spectral BRDF image slices of different types of materials may be considered under differently colored light sources placed at different positions, as shown above, for example, in FIGS. 1 to 8. Every incident illumination may be represented by $(\theta, \Lambda)$. Accordingly, $\theta \in \{\theta_1, \ldots, \theta_N\}$ may be used to indicate the angle of the light source relative to the normal of the surface being imaged, and $\Lambda \in \{\Lambda_1, \ldots, \Lambda_M\}$ may be used to indicate the spectral band of the illuminating light source or LED.

Figure 30:
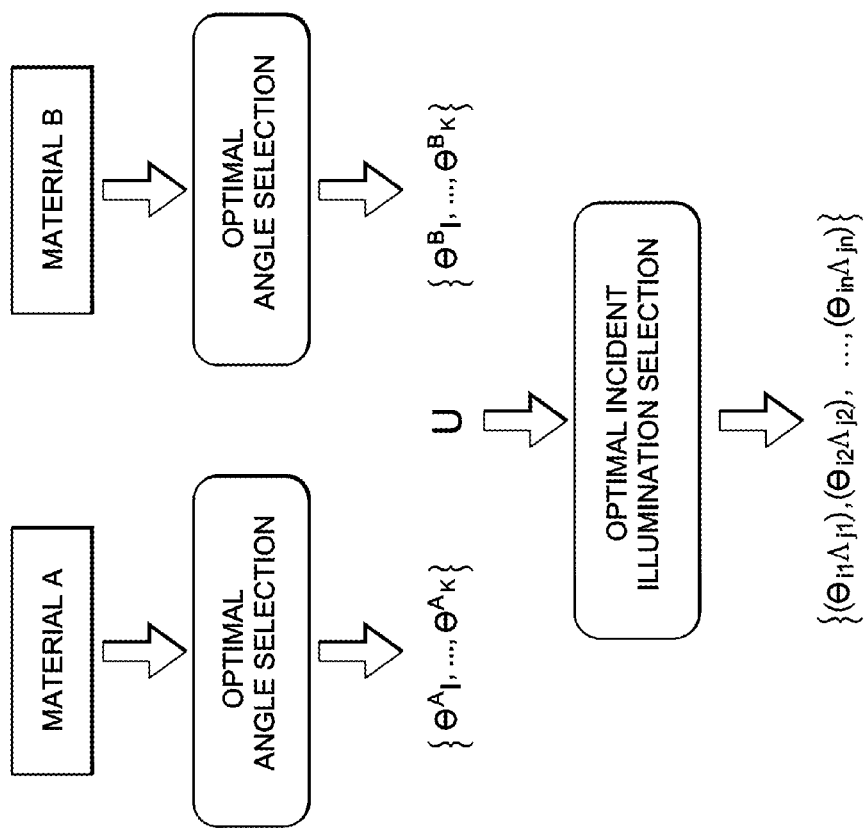
FIG. 30 is a flow diagram illustrating a two-step learning algorithm consisting of material-based angle selection and task-based optimal incident illumination selection according to an example embodiment.

The overall framework of the proposed approach is illustrated in FIG. 30. In FIG. 30, the algorithm flow is shown in two steps: material-based angle selection and task-based optimal incident illumination selection.

In another example aspect, an orientation invariant image-level feature vector representation for spectral BRDF image slices is provided, as described above with respect to, for example, FIGS. 23 to 26.

The image captured under a specific illumination $\theta$, $\Lambda$ may be denoted by $I_{\theta,\Lambda}$. One may therefore denote the corresponding regions of the image as $I^S$, $I^D$, and $I^R$. As mentioned above, since these image regions differ among different slices, it is possible to learn their means $\mu_S$, $\mu_D$, $\mu_R$ using K-means clustering, with the number of clusters set to three, as described above with respect to, for example, in FIG. 25. In the example embodiment three clusters are used, however it is possible to use a different number of clusters. Given the means, two types of feature vectors for each image slice may be computed, the mean feature and the histogram feature as described below:

Mean Feature (MF):

$$X_{\theta,\Lambda} = [\mu_S, \mu_D, \mu_R], \quad \text{(Equation 4-1)}$$

Histogram Feature (HF):

$$X_{\theta,\Lambda} = \left[ \frac{|I^S_{\theta,\Lambda}|}{P}, \frac{|I^D_{\theta,\Lambda}|}{P}, \frac{|I^R_{\theta,\Lambda}|}{P} \right], \quad \text{(Equation 4-2)}$$

In Equation 4-2, $|I|$ indicates the number of elements in set $I$ and $P$ is the total number of pixels in one image.

In a further example aspect, an algorithm may be used to learn incident illumination angles given the set of all possible illumination angles $\{\theta_1, \ldots, \theta_N\}$, as well as the BRDF image slices of one material.

Figure 31:
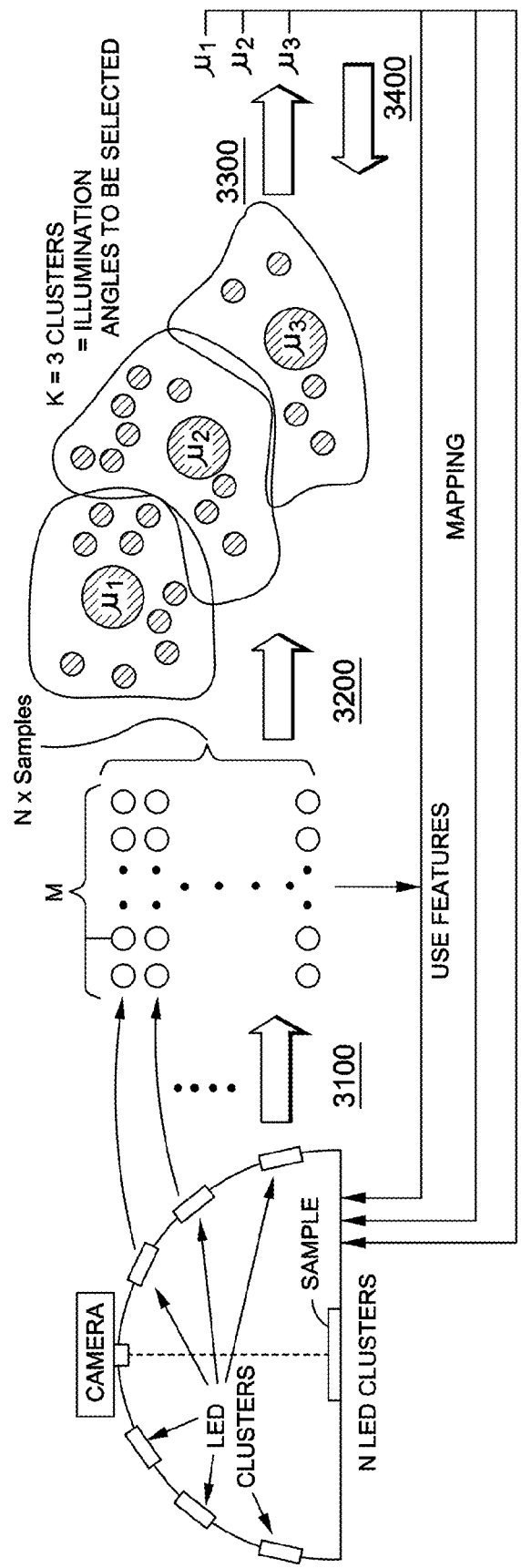
FIG. 31 is a diagram explaining the steps of a material-based angle selection algorithm according to an example embodiment.

FIG. 31 shows the steps of the material-based angle selection algorithm. First, in step 3100, M-dimensional feature vectors are extracted from the image samples corresponding to each of the angles as denoted with the unfilled circles. Each circle represents the feature of an image corresponding to one light source. N×# of samples is the number of feature vectors, where N is the total number of light sources. In step 3200, the feature vectors are then clustered to obtain K clusters which are equal to the number of angles to be selected. Each filled point in space corresponds to the M-dimensional feature vector of a material type. Next, in step 3300, the means $\mu_S$, $\mu_D$, $\mu_R$ are mapped to the initial feature vectors to select one closest feature vector to each using the Euclidean distance metric (other metrics can be used). Finally, in step 3400, each of the three selected feature vectors are mapped to a light source position given the correspondence between the feature vectors and the illumination angles used in capturing the corresponding image.

According to further example aspects, at each selected optimal angle, light sources of different bands can be placed. The goal being to select incident illumination $(\theta, \Lambda)$ with which to illuminate materials such that one can best discriminate among them, as described above with respect to, for example, FIGS. 1 to 8. Assuming the task is to classify two materials, indicated by A and B, their learned angles can be indicated by $(\theta_1^A, \theta_2^A, \ldots, \theta_K^A)$ and $(\theta_1^B, \theta_2^B, \ldots, \theta_K^B)$ respectively. The set of angles available for the task can thus be represented by Equation 4-3:

$$\Theta = \Theta^A \cup \Theta^B = \{\theta_1^A, \theta_2^A, \ldots, \theta_K^A\} \cup \{\theta_1^B, \theta_2^B, \ldots, \theta_K^B\} \quad \text{(Equation 4-3)}$$

In Equation 4-3, $|\Theta| \leq |\Theta^A| + |\Theta^B|$ because there might be common learned angles among A and B. Next, the Earth Mover's Distance $D_{EMD}$ between the image feature vectors of the samples of A and B corresponding to the $\Theta$ and all possible bands Λ may be maximized. In an example aspect, BRDF image slices captured using a white light source at an angle $\theta_i$ may be used where i is the position indicating the location of the angle (e.g. as in FIG. 23):

$$D_{EMD}^{AB}(\theta, \Lambda) = \frac{\sum_{s \in A} \sum_{t \in B} f_{st} \|X_{\theta,\Lambda}^A(s) - X_{\theta,\Lambda}^B(t)\|}{\sum_{s \in A} \sum_{t \in B} f_{st}} \quad \text{(Equation 4-4)}$$

In Equation 4-4, $f_{st}$ is the flow between $X_{\theta,\Lambda}^A(s)$ and $X_{\theta,\Lambda}^B(t)$; s and t represent the samples of A and B respectively; and θ∈Θ is the subset of angles defined in Equation 4-3. Finally, Λ represents all possible spectral bands. Accordingly, fst may be computed such that it minimizes the following cost, denoted by C:

$$C = \sum_{s \in A} \sum_{t \in B} f_{st} \|X_{\theta,\Lambda}^A(s) - X_{\theta,\Lambda}^B(t)\| \quad \text{(Equation 4-5)}$$

where Equation 4-5 is subject to the constraints:

$$f_{st} \geq 0 \quad s \in A, t \in B;$$
$$\sum_{s \in A} f_{st} \leq w_t^B \quad s \in A;$$
$$\sum_{t \in B} f_{st} \leq w_s^A \quad t \in B;$$
$$\sum_{s \in A} \sum_{t \in B} f_{st} = \min\left(\sum_{s \in A} w_s^A, \sum_{t \in B} w_t^B\right).$$

The weight vector $w_{X_{\theta,\Lambda}^A}$ is denoted by $w_s^A$ and the weight vector $w_{X_{\theta,\Lambda}^B}$ is denoted by $w_t^B$ for simplicity. The entries of these weights are assumed to be equal and to sum to one, so that they weigh all samples in a material set equally.

Finally, n incident illuminations (θ,Λ) may be chosen to give the maximum value of $D_{EMD}^{AB}$. The complexity of computing this distance is O(|A||B|) and therefore reducing the space of (Θ,Λ) over which to compute this distance helps to reduce computational complexity.

The reduction in search space does not compromise on classification accuracy. Additionally, it should be noted that material-based angle selection decreases the complexity of the system, since it allows for a reduction in the amount of times Equation 4-4 is computed.

Another example distance metric is provided below:

$$D^{AB}(\theta, \Lambda) = \min \sum_{s \in A} \sum_{t \in B} \|X_{\theta,\Lambda}^A(s) - X_{\theta,\Lambda}^B(t)\|P \quad \text{(Equation 4-6)}$$

In Equation 4-6, s and t represent the samples of material A and material B respectively; θ∈Θ is the subset of angles defined in Equation 4-3; and Λ represents all wavelengths.

Using Equation 4-6, n incident illuminations (θ,Λ)∈ $\{\theta_1, \ldots, \theta_N\} \times \{\Lambda_1, \ldots, \Lambda_M\}$ may be chosen to give the maximum values of $D^{AB}$.

It should be noted that material-based angle selection decreases the complexity of the system, since it allows a reduction in the amount of times in which Equation 4-6 is computed.

By way of these additional examples, a joint learning algorithm may be used to cluster angles by spectral BRDF images, providing means by which to reduce the search space of optimal angle and wavelength.

<Material Classification Experiments>

The performance of this joint learning approach was evaluated using the spectral BRDF image database provided by Gu in citation [2], which comprises ten material categories with four or more samples in each. In total, there were ten material classes, six metal ones and four non-metal ones. The metal ones were Alloy, Copper, Brass, Stainless steel, two types of steel, and four types of Aluminum; the non-metal ones were fabric, ceramic, plastic, and wood. Each material sample was imaged 150 times using each of the LEDs of the imaging dome, yielding 150 spectral BRDF image slices associated with it. The LEDs in the dome were grouped into 25 LED clusters, each placed at a different angle. Each cluster comprised six LEDs of the following colors: blue, green, yellow, red, white, and orange.

The experimental paradigm was as follows. Feature vectors (HF or MF) were extracted for the BRDF image slices. The Support Vector Machine (SVM) was used for classification using the linear kernel and setting the regularization parameter C to 10. A radial kernel was also tested in several cases; however no improvement in classification accuracy was found. Sets of two material types each were constructed from the total set of material categories to obtain 50 classification tasks: 23 sets comprised only metal materials (metal sets), while 27 sets comprised a mix of metal and non-metal materials (mixed sets). Different combinations or folds of training and testing data were chosen. In total, 16 folds of training and testing data were considered, where 75% of the samples were used for training, and 25% were used for testing. The classification accuracy computed was then taken to be the average over the accuracies computed for each of the test sets of the 16 folds.

<Incident Illumination Learning Performance>

Material classification was evaluated given sample images captured under illumination from the selected light sources as described above. Two types of features, the HF and MF, as described in Equations 4-1 and 4-2, were extracted for the images.

Table 7 shows the results of classification for two types of feature vectors and for different numbers of selected angle, band combinations, from 1 to 5. Additionally, the performance was compared when selecting the angle-bands as given by the algorithm described herein to those as given by material-based angle selection in Table 8. Material-based angle selection is in itself task independent; however, in order to evaluate, images were used corresponding to the selected angles for the 50 classification tasks described above. Also, the table shows a comparison to the case when all angle-bands were used for benchmarking.

TABLE 7

| Feature | % accuracy over Number of LEDs (n) | | | | | | | | | | | | | | |
|---|---|---|---|---|---|---|---|---|---|---|---|---|---|---|---|
| | 1 | | | 2 | | | 3 | | | 4 | | | 5 | | |
| MF | 76.8 | 80.1 | 83.1 | 81.2 | 81.8 | 83.2 | 82.5 | 79.8 | 84.4 | 83.8 | 78.1 | 83.3 | 85.2 | 77.6 | 84.1 |
| HF | 74.6 | 71.6 | 73.3 | 77.3 | 75.6 | 76.8 | 77.3 | 78.7 | 76.8 | 78.7 | 78.1 | 77.1 | 79.6 | 78.1 | 78.4 |

Table 7:

Mean classification accuracies for metal (left), non-metal (center) and mixed (right) sets over the different number of selected angle-band combinations n, ranging from 1 to 5. The accuracies are shown for two types of features: the MF in the second row, and the HF in the third row.

Figure 32A:
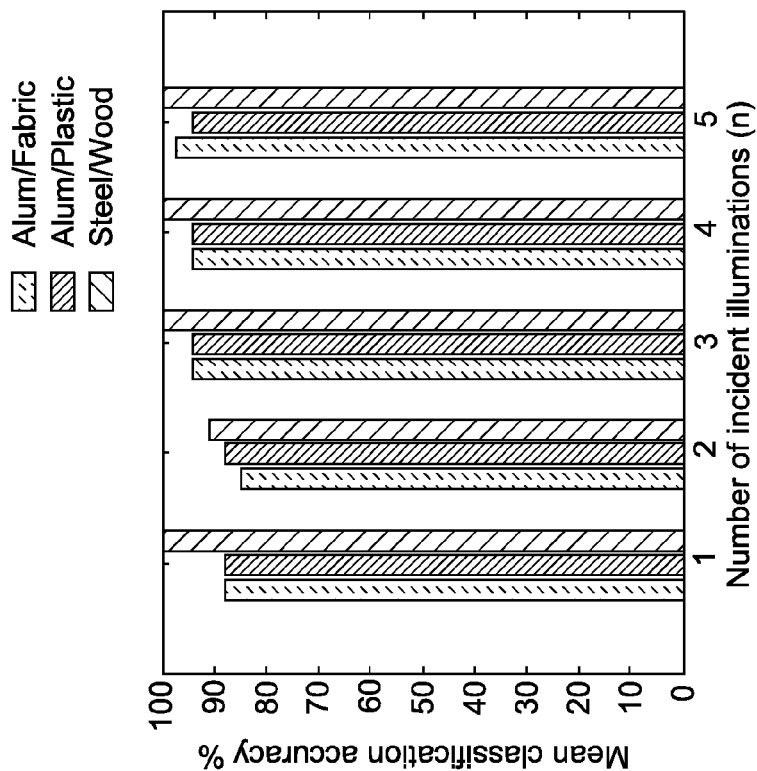
FIGS. 32(a) and 32(b) are charts illustrating the mean classification accuracies over 16 folds for 3 metal classification tasks and mixed classification tasks according to an example embodiment.
Figure 32B:
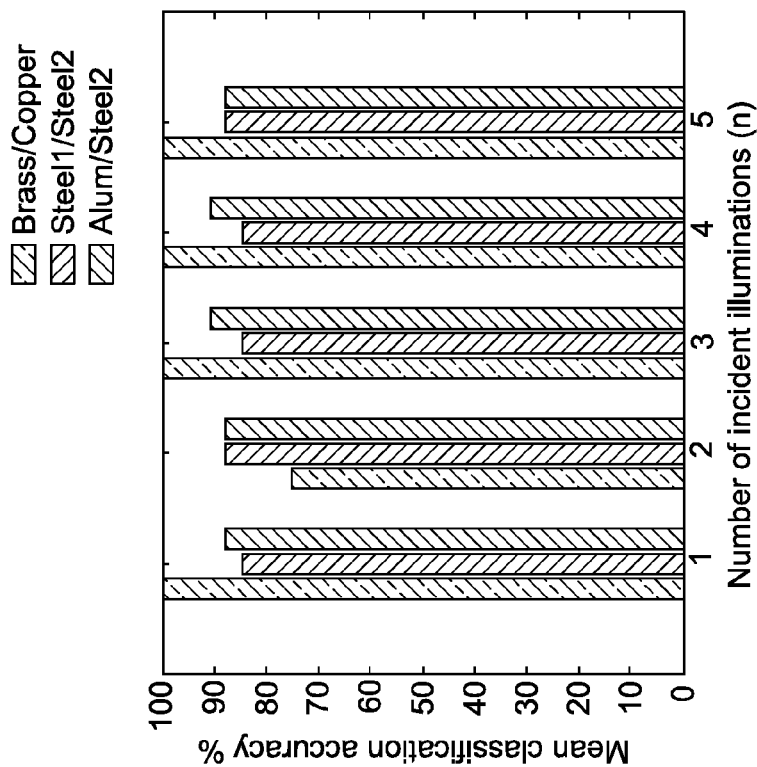

Note, in e.g. Table 7 and FIG. 32(a) and FIG. 32(b), "n" denotes the number of LEDs or incident illuminations, which is the result of the joint selection algorithm disclosed herein.

TABLE 8

| Feature | optimal illum. | | | % accuracy angle only | | | none | | |
|---|---|---|---|---|---|---|---|---|---|
| MF | 85.2 | 77.6 | 84.1 | 87.0 | 80.4 | 86.5 | 87.0 | 77.8 | 86.5 |
| HF | 79.6 | 78.1 | 78.4 | 81.8 | 80.1 | 85.3 | 81.8 | 84.9 | 85.5 |

Table 8:

Mean classification accuracies for different selection algorithm metal sets (left) and mixed sets (right) for n=5 selected angle-band combinations, the selected angles/bands given material-based angle selection, and all selected angles and bands. The accuracies are shown for two types of features: the MF in the second row and the HF in the third row.

Two general observations can be made. First, the MF provides better performance than the HF. This can be attributed to the fact that the pixels in the HF are assigned to incorrect bins as a result of noise, and the MF helps in reducing this problem. Second, material-based learning provides comparable results to when using all angles and bands. Such a result implies that a capture setup can be simplified for a particular task without compromising on classification accuracy. Additionally, to further simplify the setup, 1 or more LEDs can be used at one angle. Since the MF is the better performing feature, it was used in the remainder of the experimental results presented below.

FIG. 32(a) and FIG. 32(b) show the mean classification accuracies over 16 folds for 3 metal classification tasks and mixed classification tasks. The accuracies are plotted as a function of L, which is the number of bands or LEDs selected. N is taken to be 1, 2, 3, 4, and 5. Also shown on the plot are the accuracies as a function of the number of angles (A). In this case, 3 angles are selected from each material independently of the task. For a binary classification task, one or more angles selected for two materials might overlap. Therefore the number of LEDs generally ranges from 24 to 36.

In the case of Brass/Copper (FIG. 32(a)), it can be seen that the algorithm provides 99.9% accuracy when using 3 angles and also with 1, 3, 4, and 5 LEDs. In the case of 1 LED, the green LED at angle 13 is most commonly chosen among 16 folds. The other LED chosen is the orange one at angle 4. Since Brass and Copper have different colors, a green or an orange light source at a location allowing for diffuse reflections is sufficient to distinguish the materials. Using 2 LEDs results in a drop in performance. Both the orange and green LEDs are chosen in this case at angles 13 and 4 in all folds, which implies that the variation of both angle and band is not aiding in this classification. In the 3 LEDs case, however, the learned LEDs are among the red, orange, and green LEDs at both angles 13 and 6. In this case, the user would only need 1 or at most 3 LEDs to classify Brass and Copper. In the case of gray metals only, 1 selected LED at 1 angle is not sufficient as can be seen for classifying Aluminum/Steel and the two types of steel. For Aluminum/Steel, the classification accuracy is 87.5% when using 1 or 2 LEDs, as compared with 90.6% when using 5 LEDs or more in the case of 3 angles. In the case of 3 LEDs, 90.6% classification accuracy is achieved. In this case, the selected LEDs are at 2 different angles, which are 3 and 4, and the colors of the LEDs are green and orange as well. In the case of distinguishing two steel types, an accuracy of 87.5% is achieved when using 2 LEDs at 2 different angles (3 and 4). The performance is equivalent to that when using 5 LEDs or more. In short, illumination from more than one angle is needed to distinguish gray metals. However, in the case of colored metals, such as Brass/Copper, 1 LED is generally sufficient to obtain the best classification.

In the case of Aluminum/Fabric, FIG. 32(b), 5 LEDs are needed to provide classification accuracy (96.9%) as high as the 3 angles case. Among the selected LEDs are 2 white ones at 2 different angles (23, 47), which are needed to classify materials similar in color. For Aluminum/Plastic, 3 LEDs provide better performance than the 3 angles case. In the case of Aluminum/Plastic, 3 LEDs provide better performance (93.8%) than the 3 angles case (90.6%). In the case of Steel/Wood, 1 LED is sufficient to classify these materials (99.9%). The selected LED is an orange one at angle 4 among all folds, similar to the Brass/Copper case, as these materials differ in color. In short, the results demonstrate that the algorithm can be a useful tool to build a smaller capture setup while not compromising on classification accuracy.

<Benchmarking Performance>

The classification performance when five selected LEDs are used in capture was also compared to when using 5 LEDs selected at random corresponding to angles obtained by material-based angle learning. In particular, 20 combinations of LEDs were selected at random from the set $\binom{N}{5}$, where N is the number of LEDs corresponding to a particular task. Table 9 shows the mean classification accuracies for each of the metal and mixed sets corresponding to the method and the 20 combinations. Additionally, maximum classification accuracy over the 20 combinations is shown.

TABLE 9

| Set Type | Proposed (% acc.) | Random 5 (% acc.) |
|---|---|---|
| Metal | 85.2 | 73.2 |
| Mixed | 84.1 | 82.9 |

Table 9:

Mean classification accuracies when using illumination learned with the method as well as when using 20 sets of illumination selected at random. In each case the image slices corresponding to the illumination are used for classification.

Table 9 shows that the method outperforms the case when illumination is selected at random: by 12% in classification accuracy for the metal sets, but only 2% for the mixed sets. As shown in Table 8 the classification accuracy which can be achieved using all LEDs is only 86.4%. The reason behind these results might be that the features are not suitable for representing texture, as they are based on pixel intensities. It is expected that using texture features would significantly boost the performance. Additionally, it should be noted that in the random case the light sources are selected from learned angles, which explains a classification accuracy higher than 50%.

We performed two comparisons to prior work. The first one compared the performance of our method to that of Gu in citation [2] as shown in Table 10.

TABLE 10

| Task | Fisher Light [2] | SVM Light [2] | Proposed method |
| --- | --- | --- | --- |
| Aluminium vs Steel | 89.9 | 97.3 | 91.7 |
| Brass vs Copper | 98.5 | 99.0 | 99.9 |
| Ceramic vs Plastic | 94.4 | 95.5 | 75.0 |

Table 10:

Comparing mean classification accuracies (%) on raw materials given our method and Gu's approach in citation [2].

The performance of Gu's method is listed for three binary classification tasks: Brass/Copper, Aluminum/Steel, and Ceramic Plastic in two cases: when Gu uses the Fisher light and when Gu uses the SVM light to learn the weights on the LEDs. The accuracies depicted for Gu are for per-pixel classification, while the method described above calculates per-image accuracies. The performance of the method is similar to Gu's except for Ceramic/Plastic. As mentioned above, the method performs better on separating metals only as compared with a combination of non-metals. It is believed that texture information is needed to obtain better classification using the method.

Material classification performance when using the above-described approach was also compared to material classification when using random forest, which was used by Jehle et al. in citation [7] to learn illumination series. Table 11 shows the results in mean classification accuracies for both the metal sets and mixed sets.

TABLE 11

| Set Type | Random Forest [6] | Proposed method |
| --- | --- | --- |
| Metal | 77.1 | 85.2 |
| Non-metal | 69.8 | 77.6 |
| Mixed | 78.5 | 88.7 |

Table 11:

Comparing mean classification accuracies (%) on raw materials given our method and random forest as used by Jehle et al. for learning illumination series in citation [7].

Note that the accuracies depicted for [7] are for per-pixel classification, while the method described herein calculates per-image accuracies. The method described herein outperforms Jehle et al.'s method on metal sets by 11.2%. However, for mixed sets, the performance is 1% away from Jehle. Since Jehle et al.'s method performs per-pixel classification it can represent more spatial information in images. The above-described approach, however, uses an image-level feature representation which is suited for representing BRDF material properties. The performance of the method is similar to Gu's except for Ceramic/Plastic. As mentioned above, the method performs better on separating metals as compared with a combination of non-metals.

<Other Embodiments>

It should be understood that other embodiments according to the disclosure can combine features of the embodiments disclosed above, either in whole or in part.

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), microdrive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a non-volatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the claims directed to the inventive aspects described herein is not limited to the above-described embodiments and that various changes and modifications may be made without departing from the scope of such claims.

This disclosure has been presented for purposes of illustration and description but is not intended to be exhaustive or limiting. Many modifications and variations will be apparent to those of ordinary skill in the art who read and understand this disclosure, and this disclosure is intended to cover any and all adaptations or variations of various embodiments. The example embodiments were chosen and described in order to explain principles and practical application, and to enable others of ordinary skill in the art to understand the nature of the various embodiments. Various modifications as are suited to particular uses are contemplated. Suitable embodiments include all modifications and equivalents of the subject matter described herein, as well as any combination of features or elements of the above-described embodiments, unless otherwise indicated herein or otherwise contraindicated by context or technological compatibility or feasibility.

The invention claimed is:

1. A method for material classification of an object, comprising:
   accessing parameters for classification by a first controller, wherein the parameters include a selection to select a subset of angles for classification, a selection to select a subset of spectral bands for classification, a selection to capture texture features, and a selection to compute image-level features;
   illuminating the object by a light source;
   capturing an image of the illuminated object by an image capturing device;
   computing a feature vector of the captured image of the illuminated object by a second controller based on the parameters; and
   classifying the material from which the object is fabricated by the second controller using the feature vector.

2. The method according to claim 1, wherein responsive to a selection to select a subset of angles, an incident illumination angle of each light element cluster illuminating the object is selected based on a mathematical clustering analysis of labeled training data captured under a superset of a second number of light element clusters from different incident angles, so as to select a subset of incident illumination angles by a first number of light element clusters from the superset of the second number of light element clusters, the first number being smaller than the second number, wherein each light element cluster comprises a plurality of light elements.

3. The method according to claim 2, further comprising:
   calculating a feature vector representation for training data in a database of labeled training data captured under the superset of the second number of light element clusters from different incident angles;
   performing mathematical clustering on the feature vector representations so as to identify a subset of mathematically significant clusters of data for a corresponding first number of incident illumination angles; and
   selecting incident illumination angles for the light element clusters based on the mathematical clusters.

4. The method according to claim 3, wherein the training data is captured from a superset of a relatively large number of exitant angles, and wherein the method further comprises selecting a subset of a relatively small number of mathematically significant clusters of data for a corresponding small number of exitant angles by using mathematical clustering.

5. The method according to claim 3, wherein the number of mathematically significant clusters is selected automatically using a mathematical clustering algorithm which includes convex clustering.

6. The method according to claim 1, wherein responsive to a selection to select a subset of spectral bands, multiple spectral bands of light reflected from the illuminated object are measured,
   wherein with respect to the measured multiple spectral bands, wavelengths for the multiple spectral bands are selected by analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials in the database.

7. The method according to claim 6, wherein the multiple spectral bands are selected by steps which include:
   computing feature vector representations of the materials in the database;
   learning a set of weights representing the importance of the spectral bands on the features in each binary classification task;
   converting the weights from the binary classification tasks to a set of weights for the multi-class classification framework using a mapping function; and
   selecting spectral bands of highest weight as the selected spectral bands.

8. The method of claim 7, wherein learning a set of weights representing the importance of the spectral bands comprises application of an Adaboost algorithm.

9. The method according to claim 7, wherein the feature vector is computed from the measured spectral bands.

10. The method according to claim 1, wherein responsive to selection to capture texture features, a local binary pattern feature vector is calculated based on images of the illuminated object.

11. The method according to claim 1, wherein responsive to a selection to compute image-level features, BRDF image slices are captured for the object, low-level features of each image slice are clustered into at least two clusters, and an image-level feature vector representation is computed for each image slice with entries that are weighted means of the clusters.

12. The method according to claim 11, wherein the low-level features of each image slice are clustered into at least three clusters including a first cluster for specular reflections, a second cluster for diffuse reflections, and a third cluster for dark reflections.

13. The method according to claim 11, further comprising:
   computing feature vector representations of each slice by sorting all entries of the intermediate feature vector representations by the mean of the corresponding clusters.

14. The method according to claim 11, wherein clustering includes application of K-means clustering on the low-level features for each image slice.

15. An apparatus for selecting incident illumination angles for illumination of an object by respective light element clusters, comprising:
- a non-transitory memory for storing computer-executable process steps and for storing labeled training data; and
- one or more processors for executing the computer-executable process step stored in the non-transitory memory;
- wherein the computer-executable process steps include steps wherein the incident illumination angle of each light element cluster is selected based on a mathematical clustering analysis of labeled training data captured under a superset of a second number of light element clusters from different incident angles, so as to select a subset of incident illumination angles by a first number of light element clusters from the superset of the second number of light element clusters, the first number being smaller than the second number, wherein each light element cluster comprises a plurality of light elements.

16. An apparatus for material classification of the object, comprising:
- a first controller configured to access parameters for classification, wherein the parameters include a selection to select a subset of angles for classification, a selection to select a subset of spectral bands for classification, a selection to capture texture features, and a selection to compute image-level features;
- a light source configured to illuminate the object;
- an image capturing device configured to capture an image of the illuminated object; and
- a second controller configured to compute a feature vector of the captured image of the illuminated object based on the parameters and to classify the material from which the object is fabricated by using the feature vector.

* * * * *